(12) United States Patent
Clarke et al.

(10) Patent No.: US 7,723,112 B2
(45) Date of Patent: May 25, 2010

(54) COMPOSITIONS AND METHODS FOR TREATING AND DIAGNOSING CANCER

(75) Inventors: Michael F. Clarke, Palo Alto, CA (US); Tim Hoey, Hillsborough, CA (US); Xinhao Wang, Freemont, CA (US); Scott Dylla, Mountain View, CA (US); Austin Gurney, San Francisco, CA (US); Piero Dalerba, Palo Alto, CA (US); Mark Prince, Ann Arbor, MI (US); Grace Chen, Howell, MI (US)

(73) Assignees: The Regents of the University of Michigan, Ann Arbor, MI (US); OncoMed Pharmaceuticals, Inc., Redwood City, CA (US)

( * ) Notice: Subject to any disclaimer, the term of this patent is extended or adjusted under 35 U.S.C. 154(b) by 323 days.

(21) Appl. No.: 11/591,019

(22) Filed: Oct. 31, 2006

(65) Prior Publication Data

US 2008/0064049 A1    Mar. 13, 2008

Related U.S. Application Data

(60) Provisional application No. 60/731,469, filed on Oct. 31, 2005, provisional application No. 60/731,279, filed on Oct. 31, 2005, provisional application No. 60/731,465, filed on Oct. 31, 2005.

(51) Int. Cl.
G01N 33/53 (2006.01)
(52) U.S. Cl. .................. 435/971; 435/7.1; 435/325; 435/968
(58) Field of Classification Search ............... None
See application file for complete search history.

(56) References Cited

U.S. PATENT DOCUMENTS

| | | | |
|---|---|---|---|
| 4,109,496 A | 8/1978 | Allemann et al. |
| 4,323,546 A | 4/1982 | Crockford et al. |
| 4,411,990 A | 10/1983 | Salmon et al. |
| 4,612,282 A | 9/1986 | Schlom et al. |
| 4,670,393 A | 6/1987 | Seeburg |
| 4,873,191 A | 10/1989 | Wagner et al. |
| 4,968,103 A | 11/1990 | McNab et al. |
| 4,981,785 A | 1/1991 | Nayak |
| 5,019,497 A | 5/1991 | Olsson |
| 5,034,506 A | 7/1991 | Summerton et al. |
| 5,061,620 A | 10/1991 | Tsukamoto et al. |
| 5,087,570 A | 2/1992 | Weissman et al. |
| 5,223,409 A | 6/1993 | Ladner et al. |
| 5,225,539 A | 7/1993 | Winter |
| 5,283,317 A | 2/1994 | Saifer et al. |
| 5,358,691 A | 10/1994 | Clark et al. |
| 5,489,677 A | 2/1996 | Sanghvi et al. |
| 5,534,617 A | 7/1996 | Cunningham |
| 5,538,848 A | 7/1996 | Livak et al. |
| 5,539,082 A | 7/1996 | Nielsen et al. |
| 5,565,332 A | 10/1996 | Hoogenboom et al. |
| 5,585,089 A | 12/1996 | Queen et al. |
| 5,589,376 A | 12/1996 | Anderson et al. |
| 5,599,677 A | 2/1997 | Dowell et al. |
| 5,602,240 A | 2/1997 | De Mesmaeker et al. |
| 5,614,396 A | 3/1997 | Bradley et al. |
| 5,631,169 A | 5/1997 | Lakowicz et al. |
| 5,639,606 A | 6/1997 | Willey |
| 5,643,741 A | 7/1997 | Tsukamoto et al. |
| 5,643,765 A | 7/1997 | Willey |
| 5,648,464 A | 7/1997 | Artavanis-Tsakonas et al. |
| 5,650,317 A | 7/1997 | Chang et al. |
| 5,654,183 A | 8/1997 | Anderson et al. |
| 5,672,499 A | 9/1997 | Anderson et al. |
| 5,674,739 A | 10/1997 | Shyjan |
| 5,693,482 A | 12/1997 | Anderson et al. |
| 5,705,188 A | 1/1998 | Junichi et al. |
| 5,714,331 A | 2/1998 | Buchardt et al. |
| 5,719,262 A | 2/1998 | Buchardt et al. |
| 5,750,373 A | 5/1998 | Garrard |
| 5,750,376 A | 5/1998 | Weiss et al. |
| 5,753,229 A | 5/1998 | Mordoh et al. |
| 5,753,506 A | 5/1998 | Johe |
| 5,780,300 A | 7/1998 | Artavanis-Tsakonas et al. |
| 5,786,158 A | 7/1998 | Artavanis-Tsakonas et al. |
| 5,789,195 A | 8/1998 | Artavanis-Tsakonas et al. |
| 5,814,511 A | 9/1998 | Chang |
| 5,821,108 A | 10/1998 | Akashi et al. |

(Continued)

FOREIGN PATENT DOCUMENTS

| | | |
|---|---|---|
| WO | WO 9008832 | 8/1990 |
| WO | WO 92/19734 | 11/1992 |
| WO | WO 94/07474 | 4/1994 |

(Continued)

OTHER PUBLICATIONS

Bonnet et al. Nat Med 1997;3:730-7.*

(Continued)

*Primary Examiner*—Q. Janice Li
(74) *Attorney, Agent, or Firm*—Casimir Jones SC

(57) ABSTRACT

The present invention relates to compositions and methods for characterizing, treating and diagnosing cancer. In particular, the present invention provides a cancer stem cell profile, as well as novel stem cell cancer markers useful for the diagnosis, characterization, prognosis and treatment of cancer and in particular the targeting of solid tumor stem cells.

18 Claims, 16 Drawing Sheets

U.S. PATENT DOCUMENTS

Figure 1:
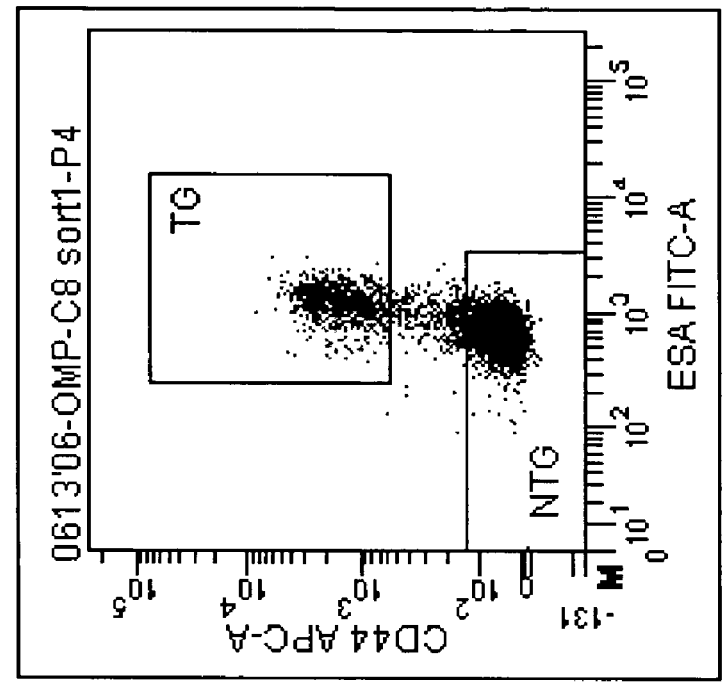
Figure 1:
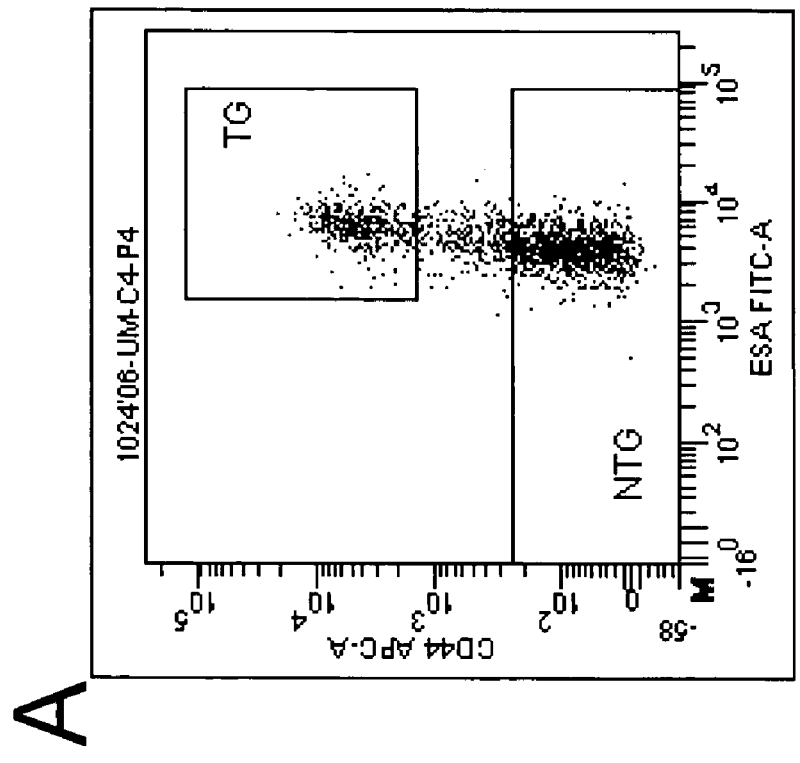

| | | | |
|---|---|---|---|
| 5,824,489 A | 10/1998 | Anderson et al. |
| 5,824,544 A | 10/1998 | Armentano et al. |
| 5,830,730 A | 11/1998 | German et al. |
| 5,834,598 A | 11/1998 | Lowman |
| 5,849,535 A | 12/1998 | Cunningham |
| 5,849,553 A | 12/1998 | Anderson et al. |
| 5,851,832 A | 12/1998 | Weiss et al. |
| 5,854,026 A | 12/1998 | Cunningham |
| 5,856,441 A | 1/1999 | Artavanis-Tsakonas et al. |
| 5,869,282 A | 2/1999 | Ish-Horowicz et al. |
| 5,872,154 A | 2/1999 | Wilson et al. |
| 5,876,978 A | 3/1999 | Willey et al. |
| 5,885,530 A | 3/1999 | Babson et al. |
| 5,885,808 A | 3/1999 | Spooner et al. |
| 5,894,869 A | 4/1999 | Mussack |
| 5,914,108 A | 6/1999 | Tsukamoto et al. |
| 5,935,792 A | 8/1999 | Rubin et al. |
| 5,942,225 A | 8/1999 | Bruder et al. |
| 5,981,225 A | 11/1999 | Kochanek et al. |
| 5,986,170 A | 11/1999 | Subjeck |
| 5,994,106 A | 11/1999 | Kovesdi et al. |
| 5,994,128 A | 11/1999 | Fallaux et al. |
| 5,994,132 A | 11/1999 | Chamberlain et al. |
| 5,994,617 A | 11/1999 | Dick et al. |
| 6,001,557 A | 12/1999 | Wilson et al. |
| 6,004,528 A | 12/1999 | Bergstein |
| 6,004,924 A | 12/1999 | Ish-Horowicz et al. |
| 6,019,978 A | 2/2000 | Ertl et al. |
| 6,022,711 A | 2/2000 | Cunningham |
| 6,033,908 A | 3/2000 | Bout et al. |
| 6,054,297 A | 4/2000 | Carter et al. |
| 6,080,912 A | 6/2000 | Bremel et al. |
| 6,083,904 A | 7/2000 | Artavanis-Tsakonas |
| 6,090,922 A | 7/2000 | Artavanis-Tsakonas et al. |
| 6,117,985 A | 9/2000 | Thomas et al. |
| 6,121,045 A | 9/2000 | McCarthy et al. |
| 6,136,563 A | 10/2000 | Cunningham |
| 6,136,952 A | 10/2000 | Li |
| 6,143,523 A | 11/2000 | Cunningham |
| 6,149,902 A | 11/2000 | Artavanis-Tsakonas et al. |
| 6,156,305 A | 12/2000 | Brauker |
| 6,159,750 A | 12/2000 | Edmonds |
| 6,180,370 B1 | 1/2001 | Queen et al. |
| 6,197,523 B1 | 3/2001 | Rimm et al. |
| 6,198,107 B1 | 3/2001 | Seville |
| 6,207,147 B1 | 3/2001 | Hiserodt |
| 6,218,166 B1 | 4/2001 | Ravindranath |
| 6,262,025 B1 | 7/2001 | Ish-Horowicz et al. |
| 6,353,150 B1 | 3/2002 | Dick et al. |
| 6,379,925 B1 | 4/2002 | Kitajewski et al. |
| 6,380,362 B1 | 4/2002 | Watson et al. |
| 6,429,186 B1 | 8/2002 | Fuh |
| 6,433,138 B1 | 8/2002 | Zimrin et al. |
| 6,448,229 B2 | 9/2002 | Teall et al. |
| 6,506,559 B1 | 1/2003 | Driver et al. |
| 6,537,775 B1 | 3/2003 | Tournier-Lasserve et al. |
| 6,582,904 B2 | 6/2003 | Dahm |
| 6,583,115 B1 | 6/2003 | Kopchick |
| 6,632,620 B1 | 10/2003 | Makarovskiy |
| 6,664,098 B1 | 12/2003 | Sakano et al. |
| 6,689,744 B2 | 2/2004 | Gao et al. |
| 6,703,489 B1 | 3/2004 | Ish-Horowicz et al. |
| 6,716,974 B1 | 4/2004 | Maciag et al. |
| 6,894,522 B2 | 5/2005 | Averill et al. |
| 6,936,440 B1 | 8/2005 | Cunningham |
| 6,984,522 B2 | 1/2006 | Clarke et al. |
| 7,115,360 B2 | 10/2006 | Clarke et al. |
| 7,118,890 B2 | 10/2006 | Ish-Horowicz et al. |
| 2002/0013315 A1 | 1/2002 | Teall et al. |
| 2002/0119565 A1 | 8/2002 | Clarke et al. |
| 2002/0151487 A1 | 10/2002 | Nickoloff et al. |
| 2003/0032184 A1 | 2/2003 | Lagasse et al. |
| 2003/0055005 A1 | 3/2003 | Castro Pineiro et al. |
| 2003/0064384 A1 | 4/2003 | Hung et al. |
| 2003/0086934 A1 | 5/2003 | Botstein et al. |
| 2003/0100512 A1 | 5/2003 | Nadin et al. |
| 2003/0114387 A1 | 6/2003 | Castro Pineiro et al. |
| 2003/0119029 A1 | 6/2003 | Glick et al. |
| 2003/0135044 A1 | 7/2003 | Asberom et al. |
| 2003/0139457 A1 | 7/2003 | Baxter et al. |
| 2003/0166543 A1 | 9/2003 | Williams et al. |
| 2003/0185829 A1 | 10/2003 | Koller et al. |
| 2003/0216380 A1 | 11/2003 | Josien et al. |
| 2003/0225528 A1 | 12/2003 | Baker et al. |
| 2004/0037815 A1 | 2/2004 | Clarke et al. |
| 2004/0038876 A1 | 2/2004 | Pepinsky et al. |
| 2004/0110663 A1 | 6/2004 | Dudek et al. |
| 2004/0127474 A1 | 7/2004 | Dudek et al. |
| 2004/0209290 A1 | 10/2004 | Cobleigh et al. |
| 2004/0253602 A1 | 12/2004 | Maciag et al. |
| 2005/0003406 A1 | 1/2005 | Coignet |
| 2005/0026831 A1 | 2/2005 | Bodmer et al. |
| 2005/0054568 A1 | 3/2005 | Ling et al. |
| 2005/0070578 A1 | 3/2005 | Baxter et al. |
| 2005/0085519 A1 | 4/2005 | Rubin et al. |
| 2005/0089518 A1 | 4/2005 | Clarke et al. |
| 2005/0089896 A1 | 4/2005 | Roy et al. |
| 2005/0112121 A1 | 5/2005 | Artavanis-Tsakonas et al. |
| 2005/0112125 A1 | 5/2005 | Burkly et al. |
| 2005/0187179 A1 | 8/2005 | Miele et al. |
| 2005/0221476 A1 | 10/2005 | Sen et al. |
| 2005/0222087 A1 | 10/2005 | Beachy et al. |
| 2005/0232927 A1 | 10/2005 | Clarke et al. |
| 2005/0244388 A1 | 11/2005 | Petersen et al. |
| 2006/0019256 A1 | 1/2006 | Clarke et al. |
| 2006/0083682 A1 | 4/2006 | Bergstein |
| 2006/0122373 A1 | 6/2006 | McCarthy et al. |
| 2006/0134121 A1 | 6/2006 | Thurston et al. |
| 2006/0263774 A1 | 11/2006 | Clark et al. |
| 2007/0041984 A1 | 2/2007 | Bergstein et al. |
| 2007/0190647 A1 | 8/2007 | Clarke et al. |

FOREIGN PATENT DOCUMENTS

| | | |
|---|---|---|
| WO | WO 9410300 | 5/1994 |
| WO | WO 97/01571 | 1/1997 |
| WO | WO 9730731 | 8/1997 |
| WO | WO 97/37004 | 10/1997 |
| WO | WO 98/45434 | 10/1998 |
| WO | WO98/57621 | 12/1998 |
| WO | WO 9902685 | 1/1999 |
| WO | WO 0009675 | 2/2000 |
| WO | WO 0012738 | 3/2000 |
| WO | WO 00/52143 | 9/2000 |
| WO | WO 01/52143 | 9/2000 |
| WO | WO 0198537 | 12/2001 |
| WO | WO 00/20575 | 1/2002 |
| WO | WO 02/00576 | 1/2002 |
| WO | WO 00/06726 | 2/2002 |
| WO | WO 01/40466 | 2/2002 |
| WO | WO 02/12447 | 2/2002 |
| WO | WO 0218544 | 3/2002 |
| WO | WO 02078703 | 10/2002 |
| WO | WO 02088081 | 11/2002 |
| WO | WO 02092635 | 11/2002 |
| WO | WO 02/102978 | 12/2002 |
| WO | WO 03/042246 | 5/2003 |
| WO | PCT/US02/39191 | 6/2003 |
| WO | WO 03/047316 | 6/2003 |
| WO | WO 03/050502 | 6/2003 |
| WO | WO 03/062273 | 7/2003 |
| WO | WO 03088964 | 10/2003 |
| WO | WO 2004/001004 | 12/2003 |
| WO | WO 2004/065545 A | 8/2004 |

| WO | WO 2004/091383 | 10/2004 |
| --- | --- | --- |
| WO | PCT/US2004/018266 | 1/2005 |
| WO | WO 2005/005601 | 1/2005 |
| WO | WO 2005/026334 | 3/2005 |
| WO | WO 2006/027693 | 3/2006 |
| WO | PCT/US2007/004687 | 6/2008 |

OTHER PUBLICATIONS

De Both et al. Int J Cancer 1997;72:1137-41.*
Takeuchi et al. Jpn J Cancer Res 1995;86:292-7.*
Rudy et al. Cancer Res 1993;53:1262-8.*
Balzer et al. J Mol Med 1999;77:699-712.*
Fillmore et al. Breast Cancer Res 2008;10R25:1-13.*
Abraham et al. Clin Cancer Res 2005;11:1154-9.*
Fillmore et al. Breast Cancer Res 2007;9/303:1-3.*
Yamada et al, Jpn J Cancer Res 1999;90/303:987-92.*
Liu, Cancer Res 2000;60:3429-3434.*
Clarke et al, Cancer Res 2006;66:9339-44.*
Zoller, J Mol Med 1995;73:425-38.*
Weitz et al., 2005, Lancet 365,153-65.
Beachy et al., 2004, Nature 432:324.
Lapidot et al., 1994, Nature 17:645-8.
Al-Hajj et a.,l 2003, PNAS 100:3983-8.
Reya & Clevers, 2005, Nature 434:843.
Nusse & Varmus, 1982, Cell 31:99-109.
Van Ooyen & Nusse, 1984, Cell 39:233-40.
Cabrera et al., 1987 Cell 50:659-63.
Rijewijk et al., 1987, Cell 50:649-57.
Miller et al., 1999, Oncogene 18:7860-72.
Reya et al, 2003, Nature 423:409-14.
Willert et al., 2003, Nature 423:448-52.
Murdoch et al., 2003, PNAS 100:3422-7.
Schonhoff et al. 2004, Endocrinol. 145:2639-44.
Van Es et al., 2005, Nature, 435:959.
Lunter et al. Activated leukocyte adhision molecule (CDI86), a novel actor in invasive growth, controls matrix metalloproteinase activity. Cancer Res. 2005, vol. 65, pp. 8801-8808.
Martin et al. Immunomagnetic enrichment of disserninated epithelial tumor cells from peripheral blood by MACS. Exp Hematol 1998:26:252-64.
Sakakura et al. Differential gene expression profiles of gastric cancer cells established from primary tumor and malignant ascites. Bri J Cancer 2002;vol. 87, pp. 1153-1161.
Harashima et al. Human bone marrow stroma-dependent myeloma sister cell lines MOLP-6 and MOLP-7 dericed from a patient with multiple myeloma. Hum Cell 2000, vol. 13, pp. 43-54.
Heppner, "Tumor Heterogeneity," Cancer Research vol. 44, pp. 2259-2265 (1984).
Fialkow, "Human Tumors Studied with Genetic Markers," Birth Defects, vol. 12, pp. 123-132 (1976).
Van't Veer et al, "Gene expression profiling predicts clinical outcome of breat cancer " nature, vol. 415, pp. 530-536 (2002).
Wang, et al., "Gene-expression profiles to predict distant metastasis of lymphnode negative primary breast cancer," Lancet vol. 365, pp. 671-679 (2005).
Van De Vijver et al, "A gene-expression signature as a predictor of survival in breast cancer" N Eng. J Med vol. 347, pp. 1999-2009 (2002).
Glinsky et al, "Classification of Human Breast Cancer Using Gene Expression Profiling as a Component of the Survival Predictor Algorithm," Clinical Cancer Research, vol. 10, pp. 2272-2283 (2004).
Zhang X. et al "Estrogen receptro positivity in mammary tumors on Wnt-1 transgenic mice is influenced by collaborating oncogenic mutations" Oncogene, 24: 4220-31 (2005).
Salmon et al., Quantitation Of Deferential Sensitivity of Human-Tumor Stem Cells To Anticancer Drugs,' New Engl J Med 1978, 298: 1321-7.
Janeway, Jr et al., The Immune System in Health and Disease, Immunobiology 1999, Fourth Edition.
Hartman et al., "MUC1 Isoform Specific Monoclonal Antibody 6E6/2 Detects Preferential Expression of the Novel Mucin Protein in Breast and Ovarian Cancer," Int J Cancer 1999; 82: 256-67.

Nierodzik et al, Protease-Activated Receptor I (PAR-I) Is Required and Rate-Limiting for Thrombin-Enhanced Experimental Pulmonary Metastasis,' Blood 1998; 92: 3694-3700.
Bromberg et al., "Tissue factor promotes melanoma metastasis by a pathway independent of blood coagulation," PNAS 1995; 92: 8205-9.
Jeffries et al., Neoplastic Transformation by Notch Requires Nuclear Localization, Mol Cell Bio 2000 Jun.; 20: 3928-41.
Goupille et al., Increase of rat colon carcinoma cells tumorigenicity by a(I-2) fucosyltransferase gene transfection, Glycobiol 1997; 7: 221-9.
Servignani et al., Tumorigenic Conversion of p53-deficient Colon Epithelial Cells by an Activated . . . J Clin Invest. Apr. 15, 1998;101(8).1572-80.
Miele et al, Arbiter of Differentiation and Death . . . J Cell Physiol. Dec. 1999;181(3):393-409.
Bergsagel and Park, "The Improvement of the Animal Tumor Model," Cancer Research, 29:2334-2338 1969.
Kristiansen et al. "Tumour Biological aspects of CD24, a mucin-Like adhesion molecule," J Mol Histol V., 2004, 35:(255-262).
Hiraki et al., "Tumor Cell Assay for Detecting Metastases Of Human Lung Cancer," Acta Med. Okayama, 37 (2), pp. 141-146 (1983).
Baran et al., "Detection of cancer cells in the blood by FACS sorting of CD45-cells," International J. Molecular Medicne, vol. 1, pp. 573-578 (1998).
Callahan et al., "Notch Signalling in Mammary Gland Tumorigenesis" Journal of Mammary Gland Biology and Neoplasia 6:1 pp. 23-26 (Jan. 2001).
Seki et al., Inhibition of liver metastasis formation by anti-CD44 variant exon 9 monoclonal antibody,' Int. J Oncol 1997; 11: 1257-61.
Choi, CD44S Expression in Human Colon Carcinomas Influences Growth of Liver Metastases, Int J Cancer 2000; 85: 523-6.
Givehchian, No Evidence for Cancer-related CD44 Splice Variants in Primary and Metastatic Colorectal Cancer, Eur J Cancer 1998; 34: 1099-1104.
Masson, Soluble CD44: quantification and molecular repartition in plasma of patients with colorectal cancer, Brit J Cancer 1999; 1995-2000.
Kondo, Cellular localization of CD44 correlates with cell proliferation and liver metastasis in colon cancer, 1999, Int J Clin Oncol 4: 78-83.
Beniers et al., Establishment and Characterization of Five New Human Renal Tumor Xenografts, Am J Pathol 1992; 140: 482-95.
Gong et al,. "Role of a5B1 Integrin in Determining Malignant Properties of Colon Carcinoma Cells," Cell Growth Different 1997; 8: 83-90.
Allenspach et al., "Notch Signaling in Cancer" Cancer Bial Ther 1(5): 466-476, 2002.
Fre et al., "Notch signals control the fate of immature progenitor cells in the intestine" Nature 435: 964-968, 2005.
Tannock and Hill, "the Basic Science of Oncology." 1998, New York: McGraw-Hill, pp. 357-358.
Carver and Schnitzer "Caveolae: Mining Little Caves For New Cancer Targets," Nature Review, 3: 571-81 (2003).
Collins, "Prospective Identification of Tumorigenic Prostate Cancer Stem Cells," Cancer Research 2005, 65.
Singh D et al, "Gene Expression Correlates of Clinical Prostate Cancer Behavior" Cancer Cells, 1: 203-9 (2002).
Singh, "Identification of human brain tumour initiating cells," 2004Nature Publishing Group vol. 432.
Lai et al., "Mouse Cell Surface Antigens: Nomenclature and Imnrunophenotyping," 1998., p. 87.
Hill, Identifying cancer stem cells in solid tumors: case not proven. Cancer Research, 2006 vol. 66. pp. 1891-1896.
Yasui et al. Combination of tumor necrosis factor-alpha with sulindac augments its apoptotic potential and suppresses tumor growth of human carcinoma cells in nude mice. Cancer, Mar. 2003; 97: 1412-20.
Kadowaki et al. Reg protein is overexpressed in gastrrc cancer cells, where it activates a signal transduction pathway that converges on ERK1/2 to stimulate growth. FEBS Letters, 2002, 530: 59-64.
Ji et al., Comprehensive analysis of the gene expression profiles in human gastric cancer cell lines. Oncogene, 2002, 21: 6549-6556.

Sinicrope et al. Sulindac sulfide-induced apoptosis is enhanced by a small-molecule Bcl-2 inhibitor and by Trail in human colon cancer cells overexpressing Bcl-2. Mol Cancer Ther, 2005, 4: 1475-1483.

Takahashi et al. J of Biological Chemistry, 2003, 287: 18864-18670.

Karlstrom et al., "A sensitive and quantitive assay for measuring leavage of presenilin subtrates," J. Biol Chem 277(9) pp. 6763-6766, 2002.

Austin et al., "Gip-1 is required in the germ line for regulation of the decision between mitosis and meiosis in C. elegans," Cell vol. 51 pp. 589-599 (1987).

Gallahan et al., "A new common integration region (int-3) for mouse mammary tumor virus on mouse chromosome 17," J Virol 61 (1) pp. 218-220 (1987).

Gallahan, et al. "The mouse mammary tumor associated gene INT3 is a unique member of the NOTCH gene family (NOTCH4)", Oncogene. 14(16) pp. 1883-1890 (1997).

Henrique, et al, "Maintenance of neuroepithelial progenitor cells by Delta-Notch signalling in the embryonic chick retina" Curr Biol. 7(9) pp. 661-670 (1997).

Jehn, et al. "Cutting edge: protective effects of notch-1 on TCR-induced apoptosis" J Immunol., 162(2):635-8 (1999).

Defios, et al. "Correlating notch signaling with thymocyte maturation" Immunity. vol. 9(6):777-86 (1998).

Chinnaiyan, et al, "FADD, a novel death domain-containing protein, interacts it the death domain of Fas and initiates apoptosis" Cell, 81(4):505-12 (1995).

Van Der Lely, "The future growth hormone antagonists," Current Opinion in Pharmacology, 2002, vol. 2, pp. 730-733.

Kaulsay. et al., "The effects of autocrine human growth hormone (hGh) on human mammary carcinoma cell behavior are mediated via the hGH recptor." Endocrinology, 2001, vol. 142, pp. 767-777.

Badolato, et al., "Differential expression of surface membrane growth hormone receptor on human peripheral blood 4 lymphocytes detected by dual fluorochrome flow cytometry," J. Clinical Endocrinology and Metabolism, 1994, vol. 0 79:984-990.

Yakar, et al., "The role of growth hormone/insulin-like growth factor axis in tumor growth and progression: Lessons from animal models,"Cytokine & Growth Factor Reveiw. 2005, vol. 16, pp. 407-420.

Christoori et al, "the role of the Cell-adhesion molecule E-cadherin as a Tumor-suppressor gene" Trends in biochemical sciences, Elsevier Haywards, GB vol. 24, No. 2, (Feb. 1, 1990) pp. 73-76.

Weerararna A R et la., "Wnt5a signaling directly affects cells motility and invasion of metastatic melanoma," Cancer Cell, Cell Press, US vol. 1, No. 3, Apr. 1, 2002, pp. 279-288.

Saitoh et al., "Up-regulation of WNT8B mRNA in human gastric cancer." Int J Oncology vol. 20, pp. 343-348 (2002).

Saitoh et al. , "Frequent up-regulation of WNT5A mRNA in primary gastric cancer," Intl J Mol Med vol. 9, pp. 515-519 (2002).

Hering H et al., "Direct interaction of Frizzled–1, –2, –4 and –7 with PDZ domains of PSD-95" FEBS Letters, Elsevier, Amsterdam, NL, vol. 521, No. 1-3, Jun. 19, 2002, pp. 185-189.

Braun S. et al. "The ERBB2 Oncogene identifies breat cancer stem cells: Prognotic and therapeutic implications" Breast Cancer Research and Treatment, 1999, p. 121, vol. 67, No. 1. Nijhoff, Boston, US.

Coopman P J P el al., "the Syk tyrosine kinase suppresses malignant growth of human breast cancer cells" Nature, Aug. 17, 2000, pp. 742-747, vol. 406 Nature Publishing Group, London GB.

Janke J et al: "Suppression of Tumorigenicity in Breast Cancer Cells by the Microfilament Protein Profilin 1" Journal of Experimental Medicine, May 15, 2000, pp. 1675-1685, vol. 191, No. 10, Tokyo, JP.

Welm Bryan E et al: "Sca-1pos cells in 1-21 the mouse mammary gland represent an enriched progenitor cell population" Developmental Biology, May 1, 2002, pp. 42-56, vol. 245, No. 1.

Ascoli Valeria et al: "Utility of Cytokeratin 20 in Identifying the Origin of Metastatic Carcinomas in Effusions" Diagnostic Cytopathology, 1995, pp. 303-308, vol. 12, No. 4.

Database Genbank [Online] "Homo sapiens S100 calcium-binding protein A8 (calgranul in A) (S100AB) mRNA" Mar. 19, 1999, XP00247053, Database accession No. NM 002964.

Taipal, J & Beachy, P.A. "The Hedgehog and Wnt Signalling Pathways in Cancer," nature 411, 349-54 (2001).

Van Den Berg, "The Hedgehog and Wnt signaling pathways in cancer" Nature, vol. 411, pp. 3189-3202 (1998).

Gat, et al, "De Novo Hair Foliicle Morphogenesis and Hair Tumors in Mice Esxpression a Truncated Catenin in Skin" Cell vol. 95, pp, 605-614 (1998).

Hedgepath et al, "regulation of Glycolgen Synthase Kinase 3 and Downstream Wnt Signaling by Axin," Molecular and Cellular Bio, vol. 19, pp. 7147-7157 (1997).

Van Lohuizen, M. et al. "Sequence Similarity Between the Mammalian bmi-1 Ptoto-Oncogene and the Drosophila regulatory Genes Psc and Su (z)2." Nature 353-355 (1991).

Van Der Lugt, N. M. et al, "Prosterior transformation, neurological abnormalities, and severe hematopoietic Defects in Mice with a Targeted Deletion of the bmi-1 Proto-Oncogene." Genes and Development 8, 757-769 (1994).

Cadigan, K. M. et al, Wnt signaling: a common theme in animal development. Genes &Development 11. 3286-305 (1997).

Leethanakul, et ai , "District pattern of expression of differentiation and growth-related genes in aquamous cell carcinomas of the head and neck revealed by the used of laser capture microdissection and cDNA arrays," Oncogene vol. 19, pp. 3220-3224 (2000).

Reya et al, "Wnt Signaling Regulates B Lymphocyte Proliferation through a LEF-1 Dependent Mechanism," Immunity vol. 13, pp. 15-24 (2000).

Wu, et al., "RGS proteins inhibit Xwnt-8 signaling in Xenopus embryonic development" Development vol. 127, pp. 2773-2784 (2000).

Austin, T. W. et al. A role for the Wnt gerie family in hematopoiesis: expansion of multilineage progenitor cells. Blood 89, 3624-35 (1997).

Chan et al, "A common human skin tumour is caused by activating mutations in catenin," Nature Genetics; vol. 21, pp. 410-413 (1999).

Spink K. E. et al. Structurai basis of the Axinadenomatous polyposis coil interaction Enbo J 19, 2270-9 (2000).

Tsukamoto, A. S. et al. Expression of the int-1 gene in transgenic mice Is associated with mammary gland hyperplasia and adenocarcinomas In male and female mice. Ce1155. 619-25 (1988).

Nusse, R. et al. A new nomenclature for int-1 and related genes: the Wnt gene family. Cell 64, 231 (1991).

Korinek, V et al. Depletion of epithelial stem-cell compartments in the small intestine of mice lacking Tcf-4. Nat Genet 19, 379-83 (1998).

Zhu, et al., "Catenin signaling modulatesproliferative potential of human epidermal keratinocytes independently of intracellular adhesion," Development vol. 126, pp. 2285-2298 (1999).

Nusse, R. The Wnt gene family in tumorigenesis and in normal development Journal of Steroid Biochemistry &Molecular Biology 43,9-12 (1992).

Kirikoshi et al, "Expression of WNT10A in human cancer," Int J Oncology vol. 19, pp. 997-1001 (2001).

Van De Wetering,.M et al. The beta-catenintTCF-4 complex imposes a crypt progenitor phenotype on colorectal cancer cells. Cell 111, 241-50 (2002).

Clarke et al, "At the root of brain cancer" Nature 432: 281-2 (2004).

Wong, S. C. et al. Expression of frizzled-related protein and Wnt-signalling molecules in invasive human breast tumours. J Pathol196, 145-53 (2002).

Bienz. "Catenin A Pivot between Cell Adhesion and Wnt-signalling," Current Biology vol. 15, pp. R64-R67 (2005).

Kobielak et al, "Catenin: at the junction of intercelullar adhesion and actin dynamics" nat Rev Mol Cell Biol. vol. 5, pp. 614-625 (2004).

Hazan et al., "Cadherin Switch in Tumor Progression," Annals NY Acad Science bol 1014, pp. 155-163 (2004).

Ilyas. "Wnt signalling and the mechanistic basic of tumor development" J Pathology, vol. 205, pp. 130-144 (2005).

Nie, et al, "LNX functions as a Ring type E3 ubiquitin ligase that targets the cell fate determinate Numb for ubiquitin-dependent degradation," EMBO J. vol. 21, pp. 93-102 2002.

Nie et al, "A Novel PTB-PDZ Domain Interaction Mediates Isoform-specific Ubiquitylation of Mammalian Numb" J Biol. Chem. vol. 279, pp. 20807-20815 (2004).

Kurochkin et al. "Alex1, a Novel Human Armadillo Repeat Protein That Is Expressed Differentially in Normal Tissues and Carcinomas" Biochem Biophys Res Commun, vol. 280, pp. 340-347 (2001).

Mitchell et al, "A Novel Melanoma Gene (MG5O) Encoding the Interleukin 1 Receptor Antagonist and Six Epitopes Recognized by Human Cytolytic T Lymphocytes," Cancer Reearch vol. 60, pp. 6448-6456 (2000).

Medina et al, "Glutamine Metabolism: Nutritional and Clinical Significance," American Soc. For Nutritional Sciences, J. of Nutrition vol. 131, pp, 2539S-2542S (2001).

Yamasaki et al, "Cell cycle, protelysis and cancer" Curr Opin Cell Biol., vol. 16, pp. 623-628 (2004).

Loeppen et al, "Overexpression of Glutamine Synthetase is Associated with Catenin Mutations in Mouse Liver Tumors During Promotion of Hepatocarcinogenesis by Phenobartbital" Cancer Research vol. 62, pp. 5685-5688 (2002).

Herbert et al. "Molecular physiology of cation-coupled Cl-cotransport: the SLC12 family" Pglugers Arch. European J Physiology vol. 447, pp. 580-593 (2004).

Rafi et al, "A large deletion together with a point mutation in the GALC gene is a common mutant allele in patients with infantile Krabbe disease" Hum Mol Genet, vol. 4, pp. 1285-1289 (1995).

Boggs et al, "A glycosynapse in myelin?" Glycoconjugate J. vol. 21, pp. 97-110 (2004).

Zerangue et al, "ASCT-1 Is a Neutral Amino Acid Exchanger with Chloride Channel Activity" J Biol. Chem vol. 271, pp. 27991-27994 (1996).

Shridhar et al, "Loss of Expression of a New Member of the DNAJ Protein Family Confers Resistance to Chemotherapeutic Agents Used in the Treatment of Ovarian Cancer" Cancer Research vol. 61, pp. 4258-4265 (2001).

Mills et al., "the emerging rold of lysophosphatidic acid in cancer" Nat Rev Cancer, vol. 84, pp. 582-591 (2003).

Cohen et al, "Role of Cabeolae and Cabeolins in Health and Disease" Physiol., Rev vol. 84, pp. 1341-1319 (2004).

Kobuke et al, ESDN a Novel Neuropilin-like Membrane Protein Clonsed from Vascular Cells with the Longest Secretory Signal Sequence among Eukaryotes . . . J Biol Chem Bol. 276, pp. 34105-13414 (2001).

Koshikawa et al, "Significant up-regulation of novel gene, CLCP1, in a highly metastatic lung cancer subline as well as in lung cancers in vivo" Oncogene, vol. 21, pp. 2822-2828 (2002).

Vestry et al, "Immunohistochemical expression of insulin-like growth factor binding protein 3 in invasive breast cancers and ductal carcinoma in situ. implications for clincopathology and patient outcome" Breast Cancer Res., vol. 7, pp. R119-R129 (2005).

Diederichs, et al, "S100 Family Members and Trypsinogens Are Predictors of Distant metastiasis and Survival in Early-Stage Non-Small Cell Lung Cancer" Cancer Res. vol. 64, pp. 5564-5569 (2004).

Pold et al, "Cyclooxygenase 2-Dependent Expression of Angionenic CXC Chemokins ENA-78/CXC Ligand (CXCL) 5 and Interleukin-8/CXCL8 in Human Non-Small Lung Cancer" Cancer Res vol. 64, pp. 1853-1860 (2004).

Ma et al, "Functional Expression and Mutations of c-Met and Its Therapeutic Inhibition with SU11274 and Small Interfering RNA in Non-Small Cell Lung Cancer" Cancer Research vol. 65, pp. 1479-1488 (2005).

Cao et al, "Identification of Novel Highly Expressed Genes in Pancreatic Ductal Adenocarcinomas through a Bioinformatics Analy . . . " Cancer Biol Ther. Nov. 2004;3(11):1081-9; discussion 1090-1. Epub Nov. 12, 2004.

Kim et al, "Methylation and expression of p16INK4 tumor supressor gene in primary colorectal Carcnimoas" Int J. Oncol. vol. 26, pp. 1217-1226 (2005).

Santamaria et al, "Cathepsin L2 a Novel Human Cysteine Proteinase Produced by Breast and Colorectal Carcinomas" Cancer Res. vol. 58, pp. 1624-1630 (1998).

Chen et al, "Development of the Th1-type immune responses requires the type I Cytokine receptor TCCR" Nature vol. 407: pp. 916-920 (2000).

Robinson et al, "Furhter Check points in Th1 Development" Immunity vol. 16, pp. 755-758 (2005).

Natarajan et al, "Sturcture and Function of Natural Killer Cell Receptors" Annu Rev. Immunol. vol. 20, pp. 853-885 (2002).

Lahn et al, "Protein Kinas C Alpha Expression in Breast and Ovarian Cancer" Oncology vol. 67, pp. 1-10 (2004).

Sahin et al, "RPL38, FOSL1 and UPP1 Are Predominantly Expressed in the Pancreatic Ductal Epithelium" Pancreas, vol. 30, pp. 158-167 (2005).

Closs et al, "Identification of a Low Affinity, High Capacity Transporter of Cathionic Amino Acids in Mouse Liver" J Biol. Chem. vol. 268, pp. 7538-7544 (1993).

Yeh et al, "Antisense overexpression of BMAL2 enhances cell proliferation" Oncogene vol. 22, pp. 5306-5314 (2003).

Howes et al, "Cationic Trypsingen Mutations and Pancreatitis" Clin Lab Med, vol. 25, pp. 39-59 (2005).

Berruyer et al, "Vanin-1-/- Mice Exhibit a Glutathione-Mediated Tissue Resistance to Oxidative Stress" Mol Cell Biol vol. 24, pp, 7214-7224 (2004).

Osanai et al, "Expression and characterization of Rab38, a new member of the Rab small G protein family," Biol Chem vol. 386, pp. 143-153 (2005).

Mahajan et al, "NRC-interacting Factor 1 is a Novel Cotransducer That Interacts with and Regulated the Activity of the Nuclear Hormone Receptor Coactivator NRC" Molecular and Cellular Biology vol. 22, pp. 6883-6894 (2002).

Frank "MAL a proteolipid in glycosphingolipid enriched domains: functional implications in myelin and beyond" Progress in Neuroliology, vol. 60, pp. 531-544 (2000).

Yantiss et al, "KOC (K Homology Domain Containing Protein Overexpression in Cancer)" Am J Durg Pathol vol. 29, pp. 188-198 (2005).

Jette et al, "the Tumor Supressor Adenomatous Polyposis Coli and Caudal Related Homeodomain Protein Regulate Expression of Retinol Gehydrohenase L" J. Biol Chem vol. 279, pp. 34397-34405 (2004).

Mott et al, "Regulation of matrix biology by matrix metalloproteinases" Current Opinion Cell Biology vol. 15, pp. 558-564 (2004).

Gellhaus, et al, "Connexin43 Interacts with NOV" J Biol Chem, vol. 279, pp. 3691-3642 (2004).

Ameyar et al, "A role for AP-1 in apoptosis: the case for and against" Biochimie vol. 85, pp. 747-752 (2003).

Pantschenko et al, "The interleukin-1 family of cytokines and receptors in human breast cancer: Implications for tumor progression" Int. J Oncology, vol. 23, pp. 269-284 (2003).

Uhren et al, "Secreted Frizzled related Protein 1 Binds Directly to Wingless and Is a Biphasic Modulator of Wnt Signalling" J Biol Chem, vol. 275, pp. 4374-4382 (2000).

Takahashi et al, "Cloning and Characterization of Multiple Human Genes and cDNAs Encoding Highly Related Type II Keratin 6 Isoforms" J. Biol Chem vol. 270. pp. 18581-18592 (1995).

Cristillo etal, "Cyclosporin A Inhibits Early mRNA Expression of G0S2} in Cultured Human Blood Mononuclear Cells" DNA and Cell Biology, vol. 16, pp. 1449-1458 (1997)

Rosenkilde at at. "The chemikine system—a major regulator of angiogenesis in health and disease" APMIS, vol. 112, pp. 481-495 (2004).

Togayachi et al, "Molecular Cloning and Characterization of UDO-GlcNac: Lactosylceramide 1.3 N-Acetylglucosaminyl transferase . . . " J Biol Chem vol. 26, pp. 22032-22040 (2001).

Yukimasa et al "Enhanced expression of p46 Shc in the nucleus and p52 Shc in the cytoplasm of human gastric cancer" Intl J Oncology, vol. 26, pp, 905-911 (2005).

Wagner et al, "The insulin-like groeth factor-1 pathway mediator genes: SHC1 Med300Val shows a protective effect in breast cancer" Carcinogenesis, vol. 25, pp. 2473-2478 (2004).

Schenck et al, "A highly conserved protein family interacting with the fragile X mental retardation protein (FMRO) and displaying selective interactions . . . " PNAS, vol. 98, pp. 8844-8849 (2001).

Townsend at al "The transporters asscoiates with antigen presentation" eminars in Cell Biology, vol. 4, pp, 53-61 (1993).

Zhou of al, "Expression Cloning of 2-5A-Dependent RNAaseL A uniquely Regulated Mediator of Interferon Action" Cell, vol. 72, pp. 753-765 (1993).

Silverman "Implications for Tnase L in Prostate Cancer Biology" Biochemistry, vol. 42, pp. 1805-1812 (2003).
Candidus, S. et al. No evidence for mutations in the alpha- and beta-catenin genes in human gastric and breast carcinomas. Cancer Res 56, 49-52 (1996).
Sorlie, T. et al. Truncating somatic mutation In exon 15 of the APC gene Is a rare event in human breast carcinomas. Mutations in brief No. 179. Online, Hum Mutat12, 215 (1998).
Jonsson, M., et al. Involvement of adenomatous polyposis coli (APC)/beta-catenin signalling in human br-ast cancer. Eur J Cancer 36, 242-8 (2000).
Schlosshauer, P. W. et al. APC truncation and increased beta-catenin levels in a human breast cancer cell line. Carcinogenesis 21, 1453-6 (2000).
Bafico A et al. "An autocrine mechanism for constitutive Wnt pathway activation in human cancer cells" Cancer Cell, 6: 497-506, 2004.
Bhattacharjee A et al, "Classification of human lung carcinomas by mRNA expression profiling revewals distinct adenocarcinorna subclasses" Proc. Natl Acad. USA 98: 13790-5 (2001).
Ethier, S. P. et al. Differential Isolation of normal luminal mammary epithelial cells and breast cancer cells from primary and metastatic sites using selective media. 'Cancer Res 53. 627-35 (1993).
Lam. Nature vol. 254, 1991, pp. 82-84 "A new type of synthetic peptide library for indentigying ligand-binding activity.".
Fodor. Nature vol. 364, 1993, pp. 555-556 "Multiplexed biochemical assays with biological chips.".
Cull et al., Proc Nad Acad Sci USA vol. 89, 1992, p. 1865-1869 "Screening for receptor ligands using large libraries of peptides linked to the C terminus of the lac repressor".
Scott; Smith Science vol. 249, 1990, pp. 386-390 "Searching for peptide ligands with an epitope library.".
Devlin Science vol. 249, 1990, pp. 404-406 "Random peptide libraries: a source of specific protein binding molecules.".
Cwirla et al. Proc. Natl. Acad. Sci. vol. 87, 1990, pp. 6378-8382 "Peptides on phage: a vast library of peptides for identifying ligands.".
Felici J. Mol. Biol. vol. 222, 1991, p. 301 "Selection of antibody ligands from a large library of oligopeptides expressed on a multivalent exposition vector.".
McConnell et al. Science vol. 257, 1992, pp. 1906-1912 "The cytosensor microphysiometer: biological applications of silicon technology.".
Sjolander; Urbaniczky Anal. Chem. vol. 63. 1991, pp. 2338-2345 "Integrated fluid handling system for biomolecular interaction analysis.".
Szabo et al. Curr. Opin. Struct, Biol. vol. 5, 1995, pp. 699-705 "Surface plasmon resonance and its use in biomolecular interaction analysis (BIA).".
Rivas; Minton Trends Biochem Sci vol. 18, 1993, pp. 284-287 "New developments in the study of biomolecular associations via sedimentation equililbrium.".
J. Wiley. "Current Protocols in Molecular Biology", 1999.
Heegaard J. Mol. Recognit vol. 11, 1998, pp. 141-148 "Capillary electrophoresis for the study of affinity interactions."
Hageand Tweed J. Chromatogr Biomed. Sci. Appl vol. 699, 1997, pp. 499-525 "Recent advances in chromatographic and electrophoretic methods for the study of drug-protein interactions.".
Zervos et al. "Mxi1, a protein that specifically interacts with Max to bind Myc-Max recognition sites," Cell vol. 72, 1993, pp. 223-232.
Madura et al. J. Biol.. Chem. vol. 268, 1993, pp. 12046-12054 "N-recognin/Ubc2 interactions in the N-end rule pathway."
Bartel et al. Biotechniques vol. 14, 1993 pp. 920-924 "Elimination of false positives that arise in using the two-hybrid system."
Iwabuchi et al. Oncogene vol. 8, 1993, pp. 1693-1696 "Use of the two-hybrid system to identify the domain of p53 involved in oligomerization".
Nielsen et al. Science vol. 254, 1991, p. 1497 "Sequence-selective recognition of DNA by strand displacement with a thymine-substituted polyamide."
Martin et al. Ein neuer Zugang zu 2'-O-Alkylribonucleosiden and Eigenschaften deren Oligonucleotide Helv. Chim. Acta vol. 78, 1995, p. 486.
Ghose et al. Methods Enzymol. vol. 93, 1983, p. 280 "Preparation of antibody-linked cytotoxic agents."
Thorpe et al. Cancer Res. vol. 48, 1998, p. 6396 "Improved antitumor effects of immunotoxins prepared with deglycosylated ricin A-chain and hindered disulfide linkages.".
Tuschl; Borkhardt Molecular Intervent. vol. 2, No. 3, 2002, pp. 158-167.
Caplen et al. Proc Natl Acad Sci U.S.A. vol. 98, 2001, pp. 9742-9747 "Specific inhibition of gene expression by small double-stranded RNAs in invertebrate and vertebrate systems.".
Martinez et al, "Single-Stranded Antisense si-RNAs Guide Target RNA Cleavage un RNAi" Cell, vol. 110, pp. 563-574 (2002).
Paul et al, "Effective expression of small interfering RNA in human cells" nature Biotech, vol. 29, pp. 505-508 (2002).
Elbashir et al. Nature vol. 411, 2001 pp. 494-498 "Duplexes of 21-nucleotide RNAs mediate RNA interference in cultured mammalian cells."
Elbashir et al. Genes Dev vol. 15, 2001, pp. 188-200 "RNA interference is mediated by 21- and 22- nucleotide RNAs."
Elbashir et al. EMBO J. vol. 20, 2001, pp. 6877-6888 "Functional anatomy of siRNAs for mediating efficient RNAi in Drosophila melanogaster embryo lysate.".
Brummelkamp et al. Science vol. 296, 2002, pp. 550-553 "A system for stable expression of short interfering RNAs in mammalian cells.".
Holen et al Nucleic Acids Res, vol. 30, 2002, pp. 1757-1766 "Positional effects of short interfering RNAs targeting the human coagulation trigger Tissue Factor.".
Brinster et al, Proc. Natl. Acad. Sci. USA vol. 62, 1985, pp. 4438-4442 "Factors affecting the efficiency of introducing foreign DNA into mice by microinjecting eggs.".
Janenich Proc. Natl. Acad. Sci. USA vol. 73, 1976, p. 1260 "Germ line integration and Mendelian transmission of the exogenous Moloney leukemia virus.".
Hogan et al.: 'Manipulating the Mouse Embryo', 1986, Cold Spring Harbor Laboratory Press.
Jahner et al. Proc. Natl. Acad Sci. USA vol. 82, 1985, p. 6927 "Insertion of the bacterial gpt gene into the germ line of mice by retroviral infection.".
Stewart et al. EMBO J. vol. 6, 1987; p. 383 "Expressor of retroviral vectors in transgenic mice obtained by embryo infection."
Jahner et al. Nature vol. 298, 1982, p. 623 "De novo methylation and expression of retroviral genomes during mouse embryogenesis."
Haskell; Bowen Mol. Reprod. Dev. vol. 40, 1995, p. 386 "Efficient production of transgenic cattle by retroviral infection of early embryos,".
Evans et al, Nature vol. 292, 1981, p. 154 "Establishment in culure of pluripotential cells from mouse embryos."
Bradley et al. Nature vol. 309, 1984, p. 255 "Formation or germ-line chimaeras from embryo-derived teratocarcinoma cell lines."
Gossler et al. Proc. Acad. Sci. USA vol. 83, 1986, p. 9065 "Transgenesis by means of blastocyst-derived embryonic stem cell lines."
Robertson at al. "T-cell receptor: gamma gene procure surfaces". Nature 322: 1986, p. 445-448.
Jaenisch Science vol. 240, 1988, p. 1468 "Transgenic animals."
Akashi, K.; Weissman, I. L.: 'Developmental Biology of Hematopoiesis', 2001, Oxford Univ. Press.
Baum, C. M. et al 'Isolation of a candidate human hematopoietic stem-cell population' Proc Natl Acad Sci USA vol. 89, 1992, pp. 2804-2808.
Morrison, S. et al.: 'The Purification and Characterization of Fetal Liver Hematopoietic Stem Cells' Proc. Natl. Acad. Sci. USA vol. 92, 1995, pp. 10302-10306.
Morrison, S. et al.: 'Telomerase acMorrison, S. J. et al.: 'Identification of a lineage of multipotent hematopoietic progenitors'Development vol. 124, 1997, pp. 1929-1939tivity in hematopoietic cells is associated with self-renewal potential' Immunity vol. 5, 1996, pp 207-216.
Ramalho-Santos, et al. "Sternness': Transcriptional Profiling of Embyonic and Adult Stem Cells," Science vol, 298, pp. 597-600 (2002).

Brown, "NCI's Anticancer Drug Screening Program May Not Be Selecting for Clinically Active Comounds" Oncology Research, vol. 9, pp. 213-215 (1997).

Packeisen et al, "Detection of Surface Antigen 17-1A in breast and Colorectal Cancer" Hybridoma, vol. 18, pp. 37-40 (1999).

Tax F.E., Yeargers J.J , Thomas J.H. Sequence of C elegans lag-2 reveals a cell-signalling domain shared with Delta and Serrate of Drosophila. Nature 1994;368:150-4.

Van Es, J.H., and Clevers, H., "Notch and Wnt inhibitors as potential new drugs for intestinal neoplastic disease," Trends Mol. Med. 11:496-502, Elsevier Inc., Amsterdam, The Netherlands (2005).

Van Limpt, V., et al., "Sage Analysis of Neuroblastoma Reveals a High Expression of the Human Homologue of the Drosophila Delta Gene," Med. Pediatr, Oncol. 35:554-558, Wiley-Liss, Inc., Massachusetts, U.S.A (2000).

Wang J.C.Y ., Doedens M., Dick J.E. Primitive human hernatopoeitic cells are enriched in cord blood compared with adult bone marrow or mobilized peripheral blood as measured by the quantitative in vivo SCID-repopulating cell assay. Blood 1997:89:3919-24.

Bonnet, D. and Dick, J.E., "Human acute myeloid leukemia is organized as a hierarachy that originates from a primitive hematopotetic cell," Nat. Med. 3:730, Nature Publishing Group, New York, NY, U.S.A. (1997).

Weijzen S., et al., "Activation of Notch-1 signaling maintains the neoplastic phenotype in human Ras-transformed cells,"Nat. Med. 8:979-986, Nature Publishing Group New York, NY, U.S.A. (2002).

Hainaud, P., et al., "The Role of the Vascular Endothelial Growth Factor-Delta-like 4 ligand/Notch4-Ephrin B2 Cascade in Tumor Vessel Remodeling and Endothelial Cell Functions," Cancer Res. 66:8501-8510 (Sep. 2006).

Lauret, E. et al., "Membrance-bound Delta-4 Notch Ligand reduces the prolifeeratice activity of primitive human hematopoietic CD34+C38low cells while maintaining their LTC-IC potential." Leukemia 18:788-797 (Feb. 2004).

Purow, B.W., et al., "Expression of Notch-1 and Its Ligands, Delta-Like-1 and Jagged-1, Is Critical for Clioma Cell Survival and Proliferation, "Cancer Res. 65.2353-2363, BioMed Central Ltd. London, UK (2005).

Uyttendaele, H., et al., "Notch4 and Wnt-1 Proteins Function to Regulate Branching Morphogeneses of Mammary Epithelial Cells in an Opposing Fashion, "Dev. Biol. 196-204-217, Elsevier Inc., Amsterdam, The Netherlands (1998).

Jaattela, et al. "Bcl-x and Bcl-2 inhibit TNF and Fas-induced apoptosis and activation of phospholipase A2 in breast carcinoma cells" Oncogene 10(12) pp. 2297-2305 (1995).

Bruckner, et al. "Glycosyltransferase activity of Fringe modulates Notch-Delta interactions" Nature 406, pp. 411-415 (2000).

Jones, P., et al. (1998) "Stromal Expression of Jagged 1 promotes colony formation by fetal hematopoietic progenitor cells" Blood, 92, pp. 1505-1511 (1998).

Shimizu, K. et al. "Manic fringe and lunatic fringe modify different sites of the Notch2 extracellular region, resulting in different signaling modulation" J Biol.Chem. 276, 25753.25758 (200.1).

Hicks, et al. "Fringe differentially modulates Jagged1 and Delta1 signalling through Notch1 and Notch2" N-at Cell Biol. (8) pp, 515-520 (2000).

May, W., et al. "EWS/FLI1-induced manic fringe renders NIH 3T3 cells tumorigenic" Nat Genet. 17(4) pp. 495-497 (1997).

Akashi et al. Transcriptional accessibility for genes of multiple tissues and hematopoietic lineages is hierarchically controlled during early hematopoiesis Blood, 101(2) pp. 383-389 (2003).

Hanahan, D. & Weinberg, R.A. "The hallmarks of cancer" Cell 100, 57-70 (2000).

Dontu, et al. "Role of Notch signaling in cell-fate determination of human mammary stem/progenitor cells" Breast Cancer Res. vol. 6, pp. R605-R615 (2004).

Dontu et al, In vitro propagation and transcriptional profiling of human mammary stem/progenitor cells. Gene and Development, 17: 1253-1270, 2003.

Leung et al, "Bmi1 is essential for cerebellar development and is overexpressed Xin human medulloblastomas," 2004, Nature, 428: 337-341.

Lewis and Veltmaat, "Next stop, the Twlilight Zone: Hedgehog Network Regulation of Mammary Gland Development," Journal of Mammary Gland Biology and Neoplasia, Apr. 2004. vol. 9, p. 165.

Edwards et al., "A Newly Defined Property of Somatotropin: Priming of Macrophages for Production of Superoxide Anion," Science, 239: 769 (1988).

Fuh, et al., "Rational design of potent antagonists to the human growth hormone receptor," Science, 1992; 256: 1677-1680.

Herman-Bonert et al., Growth hormone receptor antagonist therapy in acromegalic patients resistant to somatostatin anaologs, J Clin. Endocrinol Metab. 2000, 85.2958-2961.

Hughes and Friesen, "The Nature and Regulation of the Receptors for the Pituitary Growth Horman," Annu. Rev. Physiol. 47: 469 (1985).

Isaksson et al., "Mode of Action of Pituitary Growth Hormone on Target Cells," Annu. Rev. Physiol. 47: 483 (1985).

Webb, Journal of the National Cancer Institute, 95 (11): 774-775 Work on Breast Cancer Stem Cells Raises Questions About Treatment Strategies, Jun. 4, 2003, printed online, pp. 1-5.

Hallahan, et al. The SmoA1 Mouse Model Reveals That Notch Signaling Is Critical for the Growth and Survival of Sonic Hedgehog-Induced Medullablastomas' Cancer Research, vol. 64, pp. 7794-7800 (2004).

Oin. J.-Z., et al: p53-independent NOXA induction overcomes apoptotic resistance of malignant melanomas Molecular Cancer Therapeutics. vol. 3. pp. 895-902 (2004).

Maillard, et at "Mastermind critically regulates Notch-mediated lymphoid cell fate decisions" Blood, vol. 104, pp. 1696-1702 (2004).

Politi, et al. "Notch in mammary gland development and breast cancer" Seminars in Cancer Biology, vol. 14, pp. 341-341 (2004).

Axelson, H. "Notch Signaling and cancer: emerging complexity" Seminars in Cancer Biology vol. 14, pp. 317-319 (2004).

Hopfer, et al. "The Notch pathway in ovarian carcinomas and adenomas" British Journal of Cancer, vol. 93, pp. 709-718 (2005).

Curry, et al. "Gamma secretase inhibitor blocks Notch activation and induces apoptosis in Kaposi's sarcoma tumor cells" Oncogene, vol. 24, pp. 6333-6344 (2005).

Harper, et al "Notch signaling in development and disease" Clinical Genetics, vol. 84, pp. 461-472 (2003).

Berry et al, Germ-line tumor formation caused by activation of glp-1, a Caenorhabditis elegans member of the Notch family of receptors-, Development, vol. 124, pp. 925-936 (1997).

Shawber et al., Notch signaling in primary endotheliai cells. Ann NY Acad Sci., May 2003, 995: 162-170.

Rocha Lima et al. Seminars in Oncology, 2001 Suppl. 10 vol. 28, pp. 34-43.

Riechmann et al Reshaping human antibodies for therapy. Nature, vol. 332: 323-327 1988.

Park, I. K. et al., "Bmi-1 is required for maintenance of adult self-renewing haematopoietic stem cells," Nature 423, 302-5 (2003).

Berg et al., Bispecific antibodies that mediate killing of cells infected with human immunodeficiency virus of any strain. PNAS, vol. 88, 1991, pp. 4723-4727.

Chamow et al. A humanized, bispecific immunoadhesin-antibody that retargets CD3+ effectors to kill HIV-1-infected cells. J Immunol vol. 153, 1994, p. 4268.

Sambrook et al, "Molecular Cloning: A Iaboratory Manual," 1989, Cold Spring Harbor Press pp. 9.31-9.58.

Griffin et al., Initial clinical study of indium-111-labeled clone 110 anticarcinoembryonic antigen antibody in patients with colorectal cancer. J Clin One vol. 9, 1991, pp. 631-640.

Laufeer. Magnetic Resonance in Medicine vol. 22, 1991, pp. 339-342.

Khaw et al., Myocardial infarct imaging of antibodies to canine cardiac myosin with indium-111-diethylenetriamine pentaacetic acid. Science vol. 209, 1980, p. 295.

Hnatowich et al., The preparation and labeling of DTPA-coupled albumin, Int. J Appl. Radiat. lot. vol. 33, 1982, p. 327.

Kohler & Milstein Continuous cultures of fused cells secreting antibody of predefined specificity, Nature vol. 256, 1975, p. 495.

Zuckennann et al., J Med Chem vol. 37, 1994, p. 2678-2685 "Discovery of nanomolar ligands for 7-transmembrane G-protein-coupled receptors from a diverse N-(substituted)glycine peptoid library.".

Lam "Application of combinatorial library methods in cancer research and drug discovery," Anticancer Drug Des vol. 12, 1997, p. 145.

Dewitt et al. Proc natl Acad Sci., vol. 90, pp. 6909, 1993 "Diversomers": an approach to nonpeptide, nonoligomeric chemical diversity.

Erb et al., "Recursive deconvolution of combinatorial chemical libraries," Proc Nad Acad Sci vol. 91 1994, p. 11422.

Cho et al., An unnatural biopolymer, Science, vol. 261, 1993, p. 1303.

Carell et al. 1994. A novel procedure for the synthesis of libraries containing small organic molecules. Angew. Chem. Ed. Engl. 33:2059-2061.

Gallop et al., "Applications of combinatorial technologies to drug discovery. 1. Background and peptide combinatorial libraries." J Med Chem vol. 37, 1994, p. 1233.

Houghten Biotechniques col. 13, 1992, pp. 412-421"The use of synthetic peptide combinatorial libraries for the identification of bioactive peptides.".

Porter et al, "The Effiecient Design of Transplantable Tumor Assays" Br. J Cancer vol. 17, pp. 583-595 (1964).

Ahrens et al., "Soluble CD44 inhibits melanoma tumor groth by blocking cell surface CD44 binding to hyaluronic acid," Oncogene vol. 20, pp. 3399-3408 (2001).

Kufe et al., "Biological Behavior of Human Breast Carcinorna-associated Antigens Expresses during Cellular Proliferation," Cancer Research, vol. 43, pp. 851-857 (1983).

Spangrude, G. J.; Heimfeld, S.; Weissman, I. L.: 'Purification and characterization of mouse hematopoietic stem cells' Science vol. 241, 1988, pp. 58-62.

Uchida, N. et al.: 'Direct isolation of human central nervous system stern cells' Proceedings of the National Academy of Sciences vol. 97, 2000, pp. 14720-14725.

Baum, C. et al.: 'Bone Marrow Transplantation', 1994, Blackwell Scientific Publications.

Negrin, R. S. et al.: 'Transplantation of highly purified CD34+Thy-l+ hematopoietic stem cells in patients with metastatic breast cancer' Biol Blood Marrow Transplant vol. 6, 2000, pp. 262-271.

Voena, C. et al.: 'Qualitative and quantitative polymerase chain reaction detection of the residual myelorna cell contamination after positive selection of CD34+ cells with small- and large-scale Miltenyi cell sorting system' Br J Haematol vol. 117, 2002, pp. 642-645.

Michallet. M. et al.: 'Transplantation with selected autologous peripheral blood CD34+Thyl+ hematopoietic stern cells (HSCs) in multiple myeloma: impact of HSC dose on engraftment, safety, and immune reconstitution' Exp Hematol vol. 28, 2000, pp. 858-870.

Tricot, G. et al.: 'Collection, tumor contamination, and engraftment kinetics of highly purified hematopoietic progenitor cells to support high dose therapy in multiple myeloma' Blood vol. 91, 1998, pp. 4489-4495.

Barbui, A. et al.: 'Negative selection of peripheral blood stem cells to support a tandem autologous transplantation programme in multiple myeloma' British Journal of Haematology. vol. 116, 2002, pp. 202-210.

Al-Hajj, M. et al.: 'Prospective identification and isolation of breast cancer tumorigenic cells' Proc Natl Acad Sci USA 2002.

Park, C. H.: Bergsagel, D. E.; McCulloch, E. A.: 'Mouse myeloma tumor stem cells: a primary cell culture assay' J Natl Cancer Inst vol. 46, 1971, pp. 411-422.

Bruce, W. R.; Gaag, H.: 'A quantitative assay for the number of murine lymphoma cells capable of proliferation in vivo' Nature vol. 199, 1963, pp. 79-80.

Wodinsky, I.; Swiniarski, J.; Kensler, C. J.: 'Spleen colony studies of leukemia L1210.I. Growth kinetics of lymphocytic L1210 cells in vivo as determined by spleen assay' Cancer Chemother. Rep. vol. 51, 1967, pp. 415-421.

Southam, C.; Brunschwig, A.: 'Quantitative studies of autotransplantation of human cancer' Cancer vol. 14, 1961, pp. 971-978.

Lagasse, E; Weissman, I. L.: 'bcl-2 inhibits apoptosis of neutrophils but not their engulfment by macrophages' J Exp Med vol. 179, 1994, pp. 1047-1052.

Morrison et al Prospective identification, isolation by flow cytometry and in viv self-renewal of multipotent mammalian neural crest stem cells: Cell, 96 (5) 737-749 (1999).

Christensen, J. L.; Weissman, I. L.: 'Flk-2 is a marker in hematopoietic stem cell differentiation: a simple method to isolate long-term stem cells' Proc Natl Acad Sci USA vol. 98, 2001, pp. 14541-14546.

Weissman, I. L.: 'Translating stem and progenitor cell biology to the clinic: barriers and opportunities' Science vol. 287, 2000, pp. 1442-1446.

Osawa, M. et al.: 'Long-term lymphohematopoietic reconstitution by a single CD34-low/negative hematopoietic stem cell' Science vol. 273, 1996, pp. 242-245.

Domen, J.; Weissman, I. L.: 'Hematopoietic stem cells need two signals to prevent apoptosis; BCL-2 can provide one of these, Kitl/c-Kit signaling the other' J Exp Med vol. 192, 2000, pp. 1707-1718.

Miller, C. L.; Eaves, C. J.: 'Expansion in vitro of adult murine hematopoietic stem cells with transplantable lympho-myeloid reconstituting ability' Proc Natl. Acad Sci USA vol. 94, 1997, pp. 13648-13653.

Hanahan, D.; Weinberg, R. A.: 'The hallmarks of cancer' Cell vol. 100, 2000, pp. 57-70.

Phillips, R. L.; Reinhart, A. J.; Van Zant, G.: 'Genetic control of murine hematopoietic stem cell pool sizes and cycling kinetics' Proc Natl Acad Sci U SA vol. 89, 1992, pp. 11607-11611.

Muller-Sieburg, C. E. et al.: 'Genetic control of hematopoietic stern cell frequency in mice is mostly cell autonomous' Blood vol. 95, 2000, pp. 2446-2448.

Domen, J.; Cheshier, S. H.; Weissman, I. L.: 'The Role of Apoptosis in the Regulation of Hernatopoietic Stem Cells: Overexpression of BCL-2 Increases Both Their Number and Repopulation Potential' 1. Exp. Med. vol. 191, 2000, pp. 253-264.

Varnum-Finney, B. et al. Pluripotent, cytokine-dependent, hematopoietic stem cells are immortalized by constitutive Notch1 signaling. Nat Med 6, 1278-1281 (2000).

Allman, D., Aster, J. C. & Pear, W. S. Notch signaling in hematopoiesis and early lymphocyte development Immunol Rev 187, 75-86 (2002).

Christensen, S., Kodoyianni, V., Bosenberg, M., Friedman, L. & Kimble, J. lag-1, a gene required for lin-12 and glp-1 signaling in Caenorhabditis elegans, is homologous to human CBF1 and Drosophila Su(H). Development 122, 1373-1383 (1996).

Weizen, K. Brown, Activation of Notch-1 signaling maintains the neoplastic phenotype in human Ras-transformed cells, Nature Medicine, 8, 979-986 2002.

Brennan, K. & Brown, A. M. Is there a role for Notch signalling in human breast cancer? Breast Cancer Res 5, 69-75 (2003).

Imatani, A. & Callahan, R. Identification of a novel Notch-4/Int-3 RNA species encoding an activated gene product in certain human tumor cell lines. Oncogene 19, 223-231 (2000).

Nam, Y., Weng, A. P., Aster, J. C. & Blacklow, S. C. Structural requirements for assembly of the CSL intracellular Notch1.Mastermind-like 1 transcriptional activation complex. J Biol Chem 278, 21232-21239 (2003).

Petcherski, A. G. & Kimble, J. Mastermind is a putative activator for Notch. Curr Bioi 10, R471-3 (2000).

Wu, L., Sun, T., Kobayashi, K., Gao, P. & Griffin, J. D. Identification of a family of mastermind-like transcriptional coactivators for mammalian notch receptors. Mol Cell Bioi 22, 7688-700 (2002).

Lessard, J. & Sauvageau, G. Bmi-1 Determines the Proliferative Activity of Normal and Leukemic Stem Cells. Nature 255-261 (2003).

Korinek, V. et al. Two members of the Tcf family implicated in WnUbeta-catenin signaling during embryogenesis in the mouse, Mol Cell Bioi 18, 1248-56 (1998).

Livak, K. J. & Schmittgen, T. D. Analysis of relative gene expression data using real-time quantitative PCR and the 2(-Delta Delta C(T)) Method. Methods 25, 402-8 (2001).

Weng, A. P. et al. Growth suppression of pre-T acute lymphoblastic leukemia cells by inhibition of notch signaling. Molecular and Cellular Biology, American Society for Microbiology, Washington, US, vol. 23, No. 2, Jan. 1, 2003 pp. 655-664.

Suling Lil et al, "Interaction of hedgehog and notch pathways, and Bmi-1 in the regulation of human breast stem cell self-renewal" Proc Amer Associ Cancer Res, vol. 46, Apr. 2005.

Kubo Makoto et al, "Hedgehog signaling pathway is a new therapeutic target for patients with breast cancer" Cancer Research, vol. 64, No. 17 Sep. 2004, pp. 6071-6074.

Katano-M "Hedgehog signaling pathway as a therapeutic target in breast cancer," Cancer Letters, New York, NY, US vol. 227, Sep. 28, 2005, pp. 99-104.

King Randall W "Roughing up Smoothened: chemical modulators for hedgehog signaling" Journal of Biology Nov. 6, 2002, vol. 1, p. 8.

Hu Zhilan et al: "Evidence for lack of enhanced hedgehog target gene exprtession in common extracutaneous tumors" Cancer Research, Mar. 1, 2003, vol. 63, pp. 923-928.

Weng A.P., Ferrando A.A., Lee W., Morris J.P., Silverman L.B., Sanchez-Irizarry, C., et al. Activating mutations in Notch1 in T cell acute lymphoblastic leukemia. Science 2004;306:269-71.

Williams, C.K., et al., "Up-regulation of the Notch ligand Delta-like 4 inhibits VEGF-induced endothelial cell function," Blood 107:931-939 (Feb. 2006).

Wilson, A. and Radtke, F., "MUltiple functions of Notch signaling in self-renewing organs d cancer," FEBS Lett, 580:2860-2868, Elsevier, Inc. (2006).

Yan, X.-Q., et al., "A novel Notch ligand, D1I4, induces T-celileukemiallymphoma when overexpressed in mice by retroviral-mediated gene transfer," Blood 98:3793-3799, the American Society of Hematology, Washington, DC, U.S.A. (2001).

Zagouras P., et al., "Alterations in Notch signaling in neoplastic lesions of the human cervix," PNAS 92:6414-6418, the National Academy of Sciences, Washington, DC, U.S.A. (1995).

Morrison et al, "Transient Notch Activation Initiates an Irrev rsible Switch from Neurogenesis to Gliogensis by Neural Crest Stem Cells," Cell (May 26, 2000) 101(5): 499-510.

Mueller & Reisfeld, "Potential of the scid mouse as a host for human tumors," Cancer Metastasis Rev. (1991) 10: 193-200.

Ogawa M et al., "Differential Effects of Melphalan on Mouse Myelorna (Adj. PC-5) and Hemopoietic Stem Cells," Cancer Research (Dec. 1971) 31(12). 2116-2119.

Ogawa M et al, "Studies of Nitrogen Mustard Transport by Mouse Myeloma and Hemopoietic Precursor Cells," Cancer Research (Dec. 1973) (33)12: 3172-3175.

Patel el al., "Generation of Intedeukin-2-Secrcting Melanoma Cell Populationsfrom Resected Metastatic Tumors," Human Gene Therapy (1994) 5: 577-584.

Salmon et al., AACR Abstracts 19: 231, Abstract No. 922 (Mar. 1978).

Salmon SE & Hamburger AW, "Bloassay of Human Tumor Stem Cells," Science 197: 461-463 (1977).

Salmon Se, Recent Results in Cancer Research 94: 8 (1984).

Schlag P & Flentje D, "Chemosensitivity testing of human neoplasm using the soft agar colony assay," Cancer Treatment Reveiws 11 Suppl A: (1984) 131-7.

Shen L et al., "Genome-wide Search for Loss of Heterozygosity Using Laser Capture Microdissected Tissue of Breast Carcinoma: An implication for Mutator Phenotype and Breast Cancer Pathogenesis," Cancer Res.(Jul. 15, 2000) 60: 3884.

Slack, "Stem Cells in Epithelial Tissues," Science (Feb. 25, 2000) 287: 1431.

Terskikh Av et al., From hematopoiesis to neuropoiesis: Evidence of overlapping genetic programs, Proc Natl Acad Sci USA (Jul. 3, 2001) 98 (14): 7934-7939.

Visonneau S et al, "Cell Therapy of a Highly Invasive Human Breast Carcinoma Implanted in Immunodeficient (SCID) Mice," Clinical Cancer Research (Sep. 1997) 3: 1491-1500.

Von Hoff D.D. et al, "A Southwest Oncology Group Study on the Use of a Human Tumor Cloning Assay for Predicting Response in Patients With Ovarian Cancer," Cancer(Jan. 1, 1991) 67(1): 20-7.

Woodruff, "Cellular heterogeneity in tumours," BR J. Cancer 1983, 47, 589-594.

Sell, S. et al. Maturation arrest of stem cell differentiation is a common Pathway or the Cellular Origin of Teratocarcinomas And Epithelial Cancers, 1994, Lab Invest, 70, 6-22.

Bergsagel Valeriote, "Growth Characterisitics of a Mouse Plasma Cell Tumor," Cancer Research vol. 28, pp. 2187-2196 (1968).

Reya et al., "Stem cells, cancer, and cancer stem cells," Nature 2001, 414, 105-111.

Ramaswamy S. et al, "A molecular signautre of metastasis in primary solid tumors" Nat. Genet 33: 49-54 (2003).

Wolf et al., "Neural antigens in oligodendrogliomas and dysembryoplastic neuroepithelial tumors," Acta Neuropathol. 1997, 94, 436-443.

Wharton et al., "Expression of neuronal markers in oligodendroglimas: am immunohistochemical study," 1998 Neropathol App. Nerobiol 24, 302-308.

Katsetos et al., "localization of the Neuronal Class III B-Tubulin in Oligodendrogliomas: Comparison with . . . " J Neuropathol Exp Neurol. Apr. 2002;61(4):307-20.

Kondo et al., "Persistence of a small subpopulation of cancer stem-like cells in the (6 glioma cell line," PNAS 2004, 101 (3), 781-786.

Deschaseaux et al., "Direct selection of human bone marrow mesenchymal stem cells using an anti-CD49a antibody reveals their CD4Smed.low phenotype," Brit J. Haematology 2003, 122, 506-517.

Al-Hajj et al. "Self-renewal and solid tumor stem cells" Oncogene 2004, 23: 7274.

Zencak et al, "Bmi1 Loss Produces an Increase in Astroglial Cells and a Decrease in Neural Stem Cell Population and Proliferation," The Journal of Neuroscience. Jun. 15, 2005, 25 (24): 5774-5783.

Bracken et al, "EZH2 is downstream for the pRB-EzF pathways, essential for proliferation and amplifteration canal," The EMBO Journal, 2003, vol. 22, no. pp. 5323-5335.

Molofsky et al, "Bmi-1 Dependence distinguishes neural stem cell self-reneal from progenitor proliferation," Nature, 2003, 425 (6961) 9620967.

Frank-Kamenetsky et al, "Small molecule modulators of Hedgehog signaling: identification and characterization of Smoothened agonsits and atagonists," J Biol Nov. 6, 2002: 1(2) 10.

Chari Ravi V.J. "Targeted elivery of Chemotherapeutics: tumor-activated prodrug therapy," Advanced Drug Delievery Rev 31: 89-104 (1998).

Chawla, "Structural Variants of Human Growth Hormone: Biochemical, Genetic, and Clinical Aspects," Annu. Rev. Med., 34: 519 (1983).

Clarke et al., "Epigenetic Regulation of Normal and Cancer Stem Cells," Ann Ny Acad. Sci. 1044:90,2005.

Paladini et al, "Modulation of Hair Growth with Small Molecule Agonists of the Hedgehog Signalling Pathway," J Invest Dermatol. Oct. 2005, 125 (4) 638-46.

Lippman, M. E., "High-Dose Chemotherapy Plus Autologous Bone Marrow Transplantation for Metastatic Breast Cancer," N. Engl J Med 342,1119-20 (2000).

Park Y.P. et al, "Attempts: a heparin/protamine-based delivery system for enzyme drugs," J. Contolled Release 78:67-79 (2002).

Putnam, D. and Kopecek, J., "Polymer Conjugates with Anticancer Activity," Adv. Polymer Sci. 122:55-12 (1995).

Syrigos, K.N. and Epenetos, A.A., "Antibody Directed Enzyme Prodrug Therapy (ADEPT): A Review of the Experimental and Clinical Considerations," Anticancer Res., 19:606-614 (1999).

Thorner and Vance, "Growth Hormone," J. Clin. Invest., 82: 745 (1988).

Trainer et al., Treatment of acromegaly with the growth hormone-receptor antagonist pegvisomant, N. Engl. J. Med. 2000; 342:1171-1177.

Hathorn et al., "Invitro Modulation of the Invasive Metastatic Potentials of Human Renal Cell Carcinoma by Interleukin-2 and/or Interferon—Alpha Gene Transfer," Cancer 1994, 74: 1904-11.

Piselli et al., "Different Expression of CD44, ICAM-I, and HSP60 on Primary Tumor and Metastases of a Human Pancreatic Carcinoma Growing in Scid Mice," Anticancer Res 2000, 20: 825-32.

Thampoe et al., "Biochemical analysis of a human epithelial surface antigen: differential cell expression and processing," Arch Biochem Biophys 1988, 267: 342-52.

CD44: Mash term database, PubMed, 2004.

Taber's Cyclopedic Medical Dictionary (1985, F.A. Davis Company, Philadelphia, p. 274).

Kaiser, First pass at cancer genome reveals complex landscape. Science, 2006, 313: 1370.

Busken, C. et al. (Digestive Disease Week Abstracts and Itinerary Planner, 2003,l abstarct No. 850).

Tockman et al. Considerations in bringing a cancer biomarker to clinical application, Cancer Res. 1992, 52: 2711s-2718s.

Sarcoma: Stedman's Dictionary, 2004.

Larochelle et al. "Identification of primitive human hematopoietic cells capable of repopulating NOD/SCID mouse bone marrow: Implications for gene therapy," Nature Medicine vol. 2, pp. 1329-3137 (1996).

Weisenthal & Lippman "Clonogenic and Nonclonogenic In Vitro Chemosensitivity Assays," Cancer Treatment Reports, vol. 69, pp. 615-648 (1985).

Li, J.-L. and Harris, A.L., "Notch signaling from tumor cells: A new mechanism of angiogenesis," Cancer Cell 8:1-3, Cell Press (2005).

Shawber, C.J., et al., "Notch Signaling in Primary Endothelial Cells," Ann. NY. Acad. Sci. 995: 162-170, New York Academy of Sciences (2003).

Bray, S.J., "Notch signalling: a simple pathway becomes complex," Nature 7:678-689 Nature PUblishing Group (2006).

Dorsch, M., et el., "Ectopic expression of Delta4 impairs hematopoietic development and leads to lymphoproliferative disease," Blood 100:2046-2055, American Society of Hematology (2002).

Gale, NW., et al., "Haploinsufficiency of delta-like 4 ligand results in embryonic lethality due to major defects in arterial and vascular development," PNAS 101:15949-15954, National Academy of Sciences (2004).

Liu, Z.-J., et al., "Regulation of Notch1 and DlI4 by Vascular Endothelial Growth Factor in Arterial Endothelial Cells: Implications for Modulating Arteriogenesis and Angiogenesis," Molecular and Cellular Biology 23:14-25, American Society for Microbiology (2003).

Dontu, G., et al., "Role of Notch signaling in cell-fate determination of human mammary stem/progenitor cells," Breast Cancer Res. 6:R605-R615, BioMed Central Ltd. (2004).

Miele, L. and Osborne, B., "Arbiter of Differentiation and Death: Notch Signaling Meets Apoptosis," Journal of Cellular Physiology 181:393-409, Wiley-Liss, Inc. (1999).

Dontu, A., et al., Dosage-sensitive requirement for mouse DII4 in artery development, Genes & Dev. 18:2474-2478, Cold Spring Harbor Laboratory Press (2006).

Miele, L., "Notch Signaling," Clin. Cancer Res. 12:1074-1077, American Association for Cancer Research (2006).

Weng, A. P. et al. "Growth suppression of pre-T acute lymphoblastic leukemia cells by inhibition of notch signaling." Molecular and Cellular Biology, vol. 23, No. 2 (2003).

Curry et al. Gamma secretase inhibitor blocks Notch activation and induces apoptosis in Kapo's sarcoma tumor cells Oncogene, 2005 vol. 24 pp. 6333-6344.

Harper et al. "Notch signaling in development and disease." Clin Genet. 2003 vol. 64, pp. 461-472.

Axelson, H. "Notch signaling and cancer: emerging complexity." Seminars in Cancer Biology, 2004, 14:317-319.

Millard et al. "Mastermind critically regulates Notch-mediated lymphoid cell fate decisions." Blood, 2004, vol. 104, pp. 1696-1702.

Qin et al. "p53-independent NOXA induction overcomes apoptoic resistance of malignant melanomas." Mol. Cancer Ther. 2004, Vo. 3 pp. 895-902.

Hallahan at el. "The SmoA1 mouse model reveals that Notch signaling is critical for the growth and survival of sonic hedgehog-induced medulloblastomas." Cancer Research, 2004, vol. 64, pp. 7794-7800.

Allenspach et al. "Notch signaling in cancer." Cancer Biology & Therapy. Sep./Oct. 2002, vol. 1, pp. 466-476.

Bellavia, D., et al., "Constitutive activation of NF-KBand T-cell leukemia/lymphoma in Notch3 transgenic mice," EM BO J. 19:3337-3348, Oxford University Press, New York, NY U.S.A. (2000).

Brennan, K. and Brown, A.M.C., "Is there a role for Notch signalling in human breast cancer?" Breast Cancer Res. 5-69-75, BioMed Central Ltd, London, Uk (2003).

Clarke M.F., Dick J.E., Dirks P.B., Eaves C.J., Jamieson C.H., Jones D.L, M. Cancer stem cells-perspectives on current status and future directions: AACR Workshop on cancer stem cells. Cancer Res 2006;66:9339-44.

Dando, J. et al., "Notch/Delta4 Interaction in Human Embryonic Liver CD34+CD38- Cells: Positive Influence on BGU-E Production in LTC-IC Potential Maintenance," Stem Cells 23:550-560 (2005).

Dorsch, M., et al., "Ectopic expression of Delta4 impairs hematopoietic development and leads to lymphoproliferative disease," Blood 100:2046-2055 (2002).

Duarte, A., et al., "Dosage-sensitive requirement for mouse DII4 in artety development," Genes Dev. 18:2474-2478, Cold Spring Harbor, NY U.S.A. (2004).

Ellisen, L.W., et al., "TAN-1, the Human Homolog of the Drosophila Notch Gene, Is Broken by Chromosomal Translocations in T Lymphoblastic Neoplasms," Cell 66,649-661, Elsevier Inc., Amsterdam, The Netherlands (1991).

Fleming; R.J. et al., "The Notch receptor and its ligands," Trends in Cell Bioi. 7:437-441 (1997).

Hope, K.J., et al., "Acute myeloid leukemia originates from a hierarchy of leukemic stem cell classes that differ in self-renewal capacity," Nat. Immunol, 5:738-43, Nature Publishing Group, New York, NY, U.S.A. (2004).

Ishiko, E., et at, "Notch Signals Inhibit the Development of Erythroid/Megakaryocytic Cells by Suppressing GATA-1 Activity through Induction of HES1," J. Biol. Chem. 280:4929-4939, The American Society for Biochemistry and Molecular Biology, Inc. (2005).

Iso, T., et al., "Notch Signaling in Vascular Development," Arterioscler. Thromb. Vasco Biol. 23:543-553, Lippincolt Williams & Wilkins, Philadephia, PA, U.S.A. (2003).

Jarriault, S., et al., "Signalling downstream of activated mammalian Notch," Nature 377:355-356, Nature Publishing Group (1995).

Jhappan, C., et al., "Expression of an activated Notch-related int-3 transgene interferes with cell diferentiation and induces neoplastic and salviary glands," Genes & Dev. 6:345-355, Cold Spring Harbor Laboratory Press, Woodbury NY, U.S.A. (1992).

Sugimoto, A. et al., "Delta-4 Notch ligand promotes erythroid differentiation of human umbilical cord blood CD34+ cells," Exp. Hematol. 34:424-432 (Apr. 2006).

Suzuki, T., et al., "Imbalanced expression of TAN-1 and human Notch4 in endometrial cancers," Int. J. Oncol. 17:1131-1139, Spandidos Publications Ltd., Athens, Greece (2000).

Kopper, L. and Hajdu, M., "Tumor Stem Cells," Pathol. Oncol. Res 10:69-73, Aranyl Lajos Foundation, Budapest, Hungary (2004).

Krebs, L.T., et al., "Haploinsufficient lethality and formation of arteriovenous malformations in Notch pathway mutants," Genes Dev. 18:2469-2473, Cold Spring Harbor Laboratory Press (2004).

Krebs, L.T., et al., "Notch signaling is essential for vascular morphogenesis in mice," Genes & Dev. 14:1343-1352, Cold Spring Harbor Laboratory Press, Woodbury NY, U.S.A. (2000).

Leethanakul, C., et al., "Distinct pattern of expression of differentiation and growth-related genes in squamous cell carcinomas of the head and neck revealed by the use of laser capture microdissection and cDNA arrays," Oncogene 19:3220-3224, Nature Publishing Group, New York, NY, U.S.A. (2000).

Mailhos, C., et al., "Delta4, an endothelial specific Notch ligand expressed at sites of physiological and tumor angiogenesis," Differentiation 69:135-144, Blackwell Wissenschafts-Verlag (2001).

Milano J., Mckay J., Dagenais C., Foster-Brown L., Pognan F., Gadient R., et al. Modulation of Notch processing by D-secretase inhibitors causes intestinal goblet cell metaplasia and induction of genes known to specify gut secretory lineage differentiation. Toxicol Sci 2004;82:341-58.

Noguera-Troise, I., et al., "Blockade of DII4 inhibits tumour growth by promoting non-productive angiogenesis," Nature 444:1032-1037, Nature Publishing Group, New York, NY. U.S.A. (2006).

Parks, A.L., et al., "Structure-Function Analysis of Delta Trafficking, Receptor Binding and Signaling in Drosophila," Genetics 174:1947-1961, The Genetics Society of America (2006).

Parr, C., et al., "The possible correlation of Notch-1 and Notch-2 with clinical outcome and tumour clinicopathological parameters in human breast cancer," Int. J. Mol. Med. 14:779-786 Spandidos Publications Ltd., Athens, Greece (2004).

Patel, N.S., et al., "Up-regulation of Delta-like 4 Ligand in Human Tumor Vasculature and the Role of Basal Expression in Endothelial Cell Function," Cancer Res. 65:8690-8697, The American Association for Cancer Research (2005).

Pear, W.S. and Aster, J.C., "Tcell acute lymphoblastic leukemia/lymphoma: a human cancer commonly associated with aberrant Notch1 signaling," Curro Opin. Hematol. 11:426-433, Lippincott Williams & Wilkins, Philadelphia, PA, U.S.A. (2004).

Politi, K., et al., "Notch in mammary gland development and breast cancer," Semin. Cancer Biol. 14:341-347, Elsevier Inc., Amsterdam, The Netherlands (2004).

Rae, F.K., et al., "Novel Association of a Diverse Range of Genes with Renal Cell Carcinoma as Identified by Differential Display," Int. J. Cancer 88:726-732, Wiley-Liss, Inc., Massachusetts, U.S.A (2000).

Reya T., Morrison S.J., Clarke M.F., Weissman I.L. Stern cells, cancer, and cancer stem cells, Nature 2001.414.105-11.

Ridgeway., J., et al., "Inhibition of 0114 signaling inhibits tu,our growth by deregulating angiogenesis," Nature 444:1083-1087, Nature Publishing Group, New York, NY, U.S.A. (2006).

Robey, E., et al., "An Activated Form of Notch Influences the Choice between CD4 and CD8 T Cell Lineages," Cell 87:483-492, Elsevier Inc., Amsterdam, The Netherlands (1996).

Shutter, Jr., et al., "D114, a novel Notch ligand expressed in arterial endothelium," Genes & Dev. 14:1313-1318, Cold Spring Harbor Laboratory Press, Woodbury NY, U.S.A. (2000).

Dalerba, et al. "Phenotypic characterization of human colorectal cancer stem cells" 2007 PNAS, vol. 104, No. 24. pp. 10158-10163.

Dick. "Breast cancer stem cells revealed." 2003 PNAS, vol. 100, No. 7, pp. 3547-3549.

Krasna, L. et al. Large expansion of morphologically heterogeneous mammary epithelial cells, inclLiding the luminal phenotyp,e, from human breast tumours. Breast Cancer Res Treat 71.219-35 (2002).

Nusse R et al, "Mode of proviral activation of a putative mammary oncogene (int-1) on mouse chromosome 15" Nature, 307: 131-6 (1984).

Nusse, R. Insertional mutagenesis in mouse mammary tumorigenesis. Current Topics in Microbiology & Immunology 171,43-65 (1991).

Sazani, et al, "Nuclear antisense effects of neutral, anionic and cationic oligonucleotide analogs" Nucleic Acids Research, vol. 29, pp. 3965-3974 (2001).

Liu, A. et al. Cell-cell interaction in prostate generegulatioh and cytodifferentiation, Proc.NatI.Acad.ScLU.S.A 94, 10705-10710 (1997).

Marambaud et al, "A presenilin-1/secretase cleavage releases the E-cadherin intracellular domain and regulates disassemble of adhrens junctions" EMBO 21: 1948 (2002).

Brabletz et al, "Variable catenin expression in colorectal cancers indicates tumor progression driven by the tumor environment" PNAS, vol. 98, pp. 10356-10361 (2001).

Bea, S., et al., Increased Number of Chromosomal Imbalances and High-Level DNA Amplifications in Mantle Cell Lymphoma Are Associated With Blastoid Variants•, Blood. vol. 93, pp. 4365-4374 (1999).

Bea, S., et al., BMI-1 Gene Amplification and Overexpression in Hematological Malignancie Occur Mainly in Mantle Cell Lymphomas, Cancer Research, vol. 61 , pp. 2409-2412 (2001).

Raaphorst, F., et al., •Coexpression of BMI-1 and EZH2 Polycomb Group Genes in Reed-Stemberg Cells of Hodgkin's Disease, Am. J. Pathology, vol. 157, pp. 709-15 (2000).

Leong, Pitfalls in diagnostic immunohistology. Adv. Anat Pathol. 11 (2): 86-93, 2004; Abstract Only.

Wielenga et al.., Expression of CD44 in Apc and Tcf mutant mice implies regulation by the WNT pathway.Am J Pathol 154(2): 515-523, 1999.

Li, S. Y. et al. S Y et al. Beta-eatenin, a novel prognostic marker for breast eancer: its roles in cyclin D1 expression and cancer progression. Proc Nail Acad Sci USA 97, 4262-6 (2000).

Gebre-Medhin et al, Growth hormone receptor is expressed in human breast cancer. Americna Journal of Pathology, 2001: 158: 1217-1222.

Wolff et al, Early Operable Breast Cancer. Current Treatment Options in Oncology. 2000, 1: 210-220.

Blyszczuk P. et al. "Embryonic stem cells differentiate into insulin-producing cells without selection of nestin-expressing cells." Int. J. Dev. Biol., 48:1095-104 (2004).

Gudjonsson et al. "Isolation, immortalization, and characterization of a human breast epithelial cell line with stem cell properties." Genes Dev., 16:693-706 (2002).

Chang et al., "Robustness, scalability, and integration of a wound-response gene expression signature in predicting breast cancer survival," PNAS, vol. 102, pp. 3738-3742 (2005).

Li L et al., Cloning, Characterization, and the Complete 56.8-Kilobase DNA Genomics. Jul. 1, 1998; 1;51(1):45-58.

Morrison & Weissman, "The long-Term Repopulating Subset of Hematopoietic Stem Cells Is Detenninistic and Isolatable by Phenotype," Immunity (Nov. 1994) 1(8): 661-73.

Gunthert U et al. A new variant of glycoprotein CD44 confers metastatic potential to rat carcinoma cells. Cell. Apr. 5, 1991;65(1):13-24.

Morrison et al, "The Biology of Hematopoietic Stem Cells," Annu Rev. Cell Dev Biol (1995) 11:35-71.

Hennighausen L, Mouse Models for Breast Cancer, Breast Cancer Res 2: 2-7 (Dec. 17 1999).

Sugaya K et al., "Gene organization of human NOTCH4 and (CTG)I polymorphism in this human counterpart gene of mouse proto-oncogene Int3" Gene 189: 235-244 (1997).

Kummermehr J & Trott K-R, "The Proliferative Structure of Malignant Tumours," Stem Cells (Academic Press, London 1997) pp. 363-399.

Lee J-S et al, "Intracistemal Type A Particle-Mediated Activation of the Notch41int3 Gene in a Mouse Mammary Tumor: Generation of Truncated Notch41int3 mRNAs qy Retroviral Splicing Events," J Virol (Jun. 1999) 73(6) 5166-5171.

Soriano JV et at.,Expression of an activated Notch4(int-3) oncoprotein disrupts morphogenesis and induces an invasive phenotype in mammary epithelial cells in vitro. Int J Cancer. Jun. 1, 2000;86(5):652-9.

Carney DN et al., Demonstration of the stem cell nature of clonogenic tumor cells from lung cancer patients. Stem Cells. 1982;1(3):149-64.

Thelu J et al., "Notch signaling is linked to epidermal cell differentiation level in basal cell carcinoma psoriasis & wound healing," BMC Dermatol (Apr. 29, 2002) 2(1): 7.

Vormoor J et al., Establishment of an in vivo model for pediatric Ewing tumors by transplantation into NOD/scid mice. Pediatr Res. Mar. 2001;49(3):332-41.

Artavanis-Tsakonas et al, Science 284: 770 (Apr. 30, 1999).

Aubele M & Werner M, Analyt. "Heterogeneity in breast cancer and the problem of relevance of findings," Cell Path. (1999) 19: 53.

Beerman H et al., "Flow Cytometric Analysis of DNA Stemline Heterogeneity in Primary and Metastatic Breast Cancer," Cytometry (1991) 12(2): 147-54.

Bonsing et al., "High Levels of DNA Index Het rog neity in Advanced Breast Carcinomas," Cancer 1993 71: 382-391.

Bonsing et al, Allelotype analysis of flow-sorted breast cancer cells demonstrates genetically related diploid and aneuploid subpopulations in primary tumors and lymph node metastases. Genes Chromosomes Cancer. Jun. 2000;28 (2):173-83.

Morrison et al., "Regulatory Mechanisms in Stem Cell Biology," Cell (Feb. 7, 1997) 88(3): 287-98.

Morrison et al., "Regulatory Mechanisms in Stem Cell Biology," Cell (Feb. 7, 1997) 88(3): 287-98.

Clarke et al., "A recombinant bcl-x's adenovirus selectively induces apoptosis in cancer cells but not in normal bone marrow cells," Proc Natl Acad Sci USA (Nov. 1995) 92: 10024-11028.

Federico M et al, "In Vitro Drug Testing of Ovarian Cancer Using the Human Tumor Colony-Forming Assay: Comparison of in Vitro Response and Clinical Outcome1," Gynecologic Oncology (1994) 55(3 Pt 2): S156-63.

Hamburger AW & Salmon SE, "Primary Bioassay of Human Tumor Stem Cells," Science (Jul. 229, 1977) 197 (4302): 461-3.

Han et al, "Asoluble fonn of human Delta-like-I inhibits differentiation of hematopoietic progenitor cells," Blood, (Mar. 1, 2000) 95(5) 161625.

Jones et al, Development of a Bioassay for Putative Human . . . Blood. Feb. 1979;53(2):294-303.

Morrison et al., "Hematopoietic stem cells: challenges to expectations," Curr Opinion Immunol (1997) 9(2): 216.

Kordon & Smith, "An entire functional mammary gland may comprise th progeny from a single cell," Development (Apr. 22, 1998) 125: 1921-1930.

Kuukasjarvi et al., "Genetic Heterogeneity and Clonal Evolution Underlying Development of Asynchronous Metastasis in Human Breast Cancer," Cancer Res. (Apr. 15,1997) 57: 1597-1604.

Jamieson C. H. et al "Granulocyte-macrophase progenitors as candidate leukemic stem cells in blast crisis CML" N Engl J Med 357-67 (2004).

Williams, et al, "Small moleculae inhibitor of the hedgehog signaling pathway: Effects on basal cell carcinoma-like lesions," J Biol 2002, 4616-4621.

Chen et al, "Small molecule modulation of Smoothened activity," Proc Nat Acad. Sci 2002, 99: 22, 14071-14076.

Taipale et al, "Patched acts catalytically to suppress the activity of Smoothened," Nature 2002, 418, 892-897.

Taipale et al, "Effects of oncogenic mutations iin Smoothened and patched can be reversed by cyclopamine," Nature 2000, 406, 1005-1009.

US 5,686,666, 11/1997, Bass (withdrawn)

US 5,962,233, 10/1999, Livak (withdrawn)

* cited by examiner

COMPOSITIONS AND METHODS FOR TREATING AND DIAGNOSING CANCER

This application claims benefit of U.S. Appl. No. 60/731,469, filed Oct. 31, 2005, U.S. Appl. No. 60/731,465, filed Oct. 31, 2005, and U.S. Appl. No. 60/731,279, filed Oct. 31, 2005, each of which is incorporated herein by reference in its entirety.

This invention was made with government support under Grant No. 5P01CA07513606 awarded by the National Institutes of Health. The Government has certain rights in the invention.

FIELD OF THE INVENTION

The present invention relates to the field of oncology and provides novel compositions and methods for diagnosing and treating cancer. In particular, the present invention provides novel cancer stem cell markers, including, for example, the Notch signaling pathway target Hes6; CEACAM6, a member of the glycophosphatidylinositol (GPI) anchored immunoglobulin superfamily that mediates intercellular interactions; and intracellular aldehyde dehydrogenases (ALDH) useful for the study, diagnosis, and treatment of solid tumors.

BACKGROUND

Cancer is one of the leading causes of death in the developed world, resulting in over 500,000 deaths per year in the United States alone. Over one million people are diagnosed with cancer in the U.S. each year, and overall it is estimated that more than 1 in 3 people will develop some form of cancer during their lifetime. Though there are more than 200 different types of cancer, four of them—breast, lung, colorectal, and prostate—account for over half of all new cases (Jemal et al., 2003, Cancer J. Clin. 53:5-26).

Breast cancer is the most common cancer in woman, with an estimate 12% of women at risk of developing the disease during their lifetime. Although mortality rates have decreased due to earlier detection and improved treatments, breast cancer remains a leading cause of death in middle-aged women. Furthermore, metastatic breast cancer is still an incurable disease. On presentation, most patients with metastatic breast cancer have only one or two organ systems affected, but as the disease progresses, multiple sites usually become involved. The most common sites of metastatic involvement are locoregional recurrences in the skin and soft tissues of the chest wall, as well as in axilla and supraclavicular areas. The most common site for distant metastasis is the bone (30-40% of distant metastasis), followed by the lungs and liver. And although only approximately 1-5% of women with newly diagnosed breast cancer have distant metastasis at the time of diagnosis, approximately 50% of patients with local disease eventually relapse with metastasis within five years. At present the median survival from the manifestation of distant metastases is about three years.

Current methods of diagnosing and staging breast cancer include the tumor-node-metastasis (TNM) system that relies on tumor size, tumor presence in lymph nodes, and the presence of distant metastases as described in the American Joint Committee on Cancer: AJCC Cancer Staging Manual. Philadelphia, Pa.: Lippincott-Raven Publishers, 5th ed., 1997, pp 171-180, and in Harris, J R: "Staging of breast carcinoma" in Harris, J. R., Hellman, S., Henderson, I. C., Kinne D. W. (eds.): Breast Diseases. Philadelphia, Lippincott, 1991. These parameters are used to provide a prognosis and select an appropriate therapy. The morphologic appearance of the tumor may also be assessed but because tumors with similar histopathologic appearance can exhibit significant clinical variability, this approach has serious limitations. Finally assays for cell surface markers can be used to divide certain tumors types into subclasses. For example, one factor considered in the prognosis and treatment of breast cancer is the presence of the estrogen receptor (ER) as ER-positive breast cancers typically respond more readily to hormonal therapies such as tamoxifen or aromatase inhibitors than ER-negative tumors. Yet these analyses, though useful, are only partially predictive of the clinical behavior of breast tumors, and there is much phenotypic diversity present in breast cancers that current diagnostic tools fail to detect and current therapies fail to treat.

Prostate cancer is the most common cancer in men in the developed world, representing an estimated 33% of all new cancer cases in the U.S., and is the second most frequent cause of death (Jemal et al., 2003, CA Cancer J. Clin. 53:5-26). Since the introduction of the prostate specific antigen (PSA) blood test, early detection of prostate cancer has dramatically improved survival rates, and the five year survival rate for patients with local and regional stage prostate cancers at the time of diagnosis is nearing 100%. Yet more than 50% of patients will eventually develop locally advanced or metastatic disease (Muthuramalingam et al., 2004, Clin. Oncol. 16:505-16).

Currently radical prostatectomy and radiation therapy provide curative treatment for the majority of localized prostate tumors. However, therapeutic options are very limited for advanced cases. For metastatic disease, androgen ablation with luteinising hormone-releasing hormone (LHRH) agonist alone or in combination with anti-androgens is the standard treatment. Yet despite maximal androgen blockage, the disease nearly always progresses with the majority developing androgen-independent disease. At present there is no uniformly accepted treatment for hormone refractory prostate cancer, and chemotherapeutic regimes are commonly used (Muthuramalingam et al., 2004, Clin. Oncol. 16:505-16; Trojan et al., 2005, Anticancer Res. 25:551-61).

Lung cancer is the most common cancer worldwide, the third most commonly diagnosed cancer in the United States, and by far the most frequent cause of cancer deaths (Spiro et al., 2002, Am. J. Respir. Crit. Care Med. 166:1166-96; Jemal et al., 2003, CA Cancer J. Clin. 53:5-26). Cigarette smoking is believed responsible for an estimated 87% of all lung cancers making it the most deadly preventable disease. Lung cancer is divided into two major types that account for over 90% of all lung cancers: small cell lung cancer (SCLC) and non-small cell lung cancer (NSCLC). SCLC accounts for 15-20% of cases and is characterized by its origin in large central airways and histological composition of sheets of small cells with little cytoplasm. SCLC is more aggressive than NSCLC, growing rapidly and metastasizing early and often. NSCLC accounts for 80-85% of all cases and is further divided into three major subtypes based on histology: adenocarcinoma, squamous cell carcinoma (epidermoid carcinoma), and large cell undifferentiated carcinoma.

Lung cancer typically presents late in its course, and thus has a median survival of only 6-12 months after diagnosis and an overall 5 year survival rate of only 5-10%. Although surgery offers the best chance of a cure, only a small fraction of lung cancer patients are eligible with the majority relying on chemotherapy and radiotherapy. Despite attempts to manipulate the timing and dose intensity of these therapies, survival rates have increased little over the last 15 years (Spiro et al., 2002, Am. J. Respir. Crit. Care Med. 166:1166-96).

Colorectal cancer is the third most common cancer and the fourth most frequent cause of cancer deaths worldwide (Weitz et al., 2005, Lancet 365:153-65). Approximately 5-10% of all colorectal cancers are hereditary with one of the main forms being familial adenomatous polyposis (FAP), an autosomal dominant disease in which about 80% of affected individuals contain a germline mutation in the adenomatous polyposis coli (APC) gene. Colorectal carcinoma has a tendency to invade locally by circumferential growth and elsewhere by lymphatic, hematogenous, transperitoneal, and perineural spread. The most common site of extralymphatic involvement is the liver, with the lungs the most frequently affected extra-abdominal organ. Other sites of hematogenous spread include the bones, kidneys, adrenal glands, and brain.

The current staging system for colorectal cancer is based on the degree of tumor penetration through the bowel wall and the presence or absence of nodal involvement. This staging system is defined by three major Duke's classifications: Duke's A disease is confined to submucosa layers of colon or rectum; Duke's B disease has tumors that invade through muscularis propria and can penetrate the wall of the colon or rectum; and Duke's C disease includes any degree of bowel wall invasion with regional lymph node metastasis. While surgical resection is highly effective for early stage colorectal cancers, providing cure rates of 95% in Duke's A patients, the rate is reduced to 75% in Duke's B patients and the presence of positive lymph node in Duke's C disease predicts a 60% likelihood of recurrence within five years. Treatment of Duke's C patients with a post surgical course of chemotherapy reduces the recurrence rate to 40%-50%, and is now the standard of care for these patients.

Epithelial carcinomas of the head and neck arise from the mucosal surfaces in the head and neck area and are typically squamous cell in origin. This category includes tumors of the paranasal sinuses, the oral cavity, and the nasopharynx, oropharynx, hypopharynx, and larynx.

The annual number of new cases of head and neck cancers in the United States is approximately 40,000 per year, accounting for about 5 percent of adult malignancies. Head and neck cancers are more common in some other countries, and the worldwide incidence probably exceeds half a million cases annually. In North American and Europe, the tumors usually arise from the oral cavity, oropharynx, or larynx, whereas nasopharyneal cancer is more common in the Mediterranean countries and in the Far East.

Traditional modes of therapy (radiation therapy, chemotherapy, and hormonal therapy), while useful, have been limited by the emergence of treatment-resistant cancer cells. Clearly, new approaches are needed to identify targets for treating head and neck cancer and cancer generally.

Cancer arises from dysregulation of the mechanisms that control normal tissue development and maintenance, and increasingly stem cells are thought to play a central role (Beachy et al., 2004, Nature 432:324). During normal animal development, cells of most or all tissues are derived from normal precursors, called stem cells (Morrison et al., 1997, Cell 88:287-98; Morrison et al., 1997, Curr. Opin. Immunol. 9:216-21; Morrison et al., 1995, Annu. Rev. Cell. Dev. Biol. 11:35-71). Stem cells are cells that: (1) have extensive proliferative capacity; 2) are capable of asymmetric cell division to generate one or more kinds of progeny with reduced proliferative and/or developmental potential; and (3) are capable of symmetric cell divisions for self-renewal or self-maintenance. The best-known example of adult cell renewal by the differentiation of stem cells is the hematopoietic system where developmentally immature precursors (hematopoietic stem and progenitor cells) respond to molecular signals to form the varied blood and lymphoid cell types. Other cells, including cells of the gut, breast ductal system, and skin are constantly replenished from a small population of stem cells in each tissue, and recent studies suggest that most other adult tissues also harbor stem cells, including the brain.

Solid tumors are composed of heterogeneous cell populations. For example, breast cancers are a mixture of cancer cells and normal cells, including mesenchymal (stromal) cells, inflammatory cells, and endothelial cells. Classic models of cancer hold that phenotypically distinct cancer cell populations all have the capacity to proliferate and give rise to a new tumor. In the classical model, tumor cell heterogeneity results from environmental factors as well as ongoing mutations within cancer cells resulting in a diverse population of tumorigenic cells. This model rests on the idea that all populations of tumor cells would have some degree of tumorigenic potential. (Pandis et al., 1998, Genes, Chromosomes & Cancer 12:122-129; Kuukasjrvi et al., 1997, Cancer Res. 57:1597-1604; Bonsing et al., 1993, Cancer 71:382-391; Bonsing et al., 2000, Genes Chromosomes & Cancer 82: 173-183; Beerman H et al., 1991, Cytometry. 12:147-54; Aubele M & Werner M, 1999, Analyt. Cell. Path. 19:53; Shen L et al., 2000, Cancer Res. 60:3884).

An alternative model for the observed solid tumor cell heterogeneity is that solid tumors result from a "solid tumor stem cell" (or "cancer stem cell" from a solid tumor) that subsequently undergoes chaotic development through both symmetric and asymmetric rounds of cell division. In this stem cell model, solid tumors contain a distinct and limited (possibly even rare) subset of cells that share properties with normal "stem cells" in that they extensively proliferate and efficiently give rise both to additional solid tumor stem cells (self-renewal) and to the majority of within a solid tumor that lack tumorigenic potential. Indeed, mutations within a long-lived stem cell population can initiate the formation of cancer stem cells that underlie the growth and maintenance of tumors and whose presence contributes to the failure of current therapeutic approaches.

The stem cell nature of cancer was first revealed in the blood cancer, acute myeloid leukemia (AML) (Lapidot et al., 1994, Nature 17:645-8). More recently it has been demonstrated that malignant human breast tumors similarly harbor a small, distinct population of cancer stem cells enriched for the ability to form tumors in immunodeficient mice. An ESA+, CD44+, CD24−/low, Lin− cell population was found to be 50-fold enriched for tumorigenic cells compared to unfractionated tumor cells (Al-Hajj et al., 2003, PNAS 100:3983-8). Furthermore, a similar population is also present in colon cancers. The ability to prospectively isolate the tumorigenic cancer cells has permitted precise investigation of critical biological pathways that underlie tumorigenicity in these cells, and thus promises the development of better diagnostic assays and therapeutics for cancer patients. It is toward this purpose that this invention is directed.

BRIEF SUMMARY OF THE INVENTION

The present invention relates to compositions and methods in the field of oncology. In particular, the present invention provides a gene expression profile associated with solid tumor stem cells each gene of which provides a novel stem cell cancer marker. In certain embodiments a cancer stem cell gene expression profile comprises genes differentially expressed in cancer stem cells compared to unfractionated tumor cells. In other certain embodiments a cancer stem cell gene expression profile comprises genes differentially expressed in cancer stem cells compared to non-tumorigenic tumor cells, which comprise the majority of the tumor. The cancer stem cell markers identified by the present invention are useful for the characterization, diagnosis, prognosis, and treatment of cancer and in particular, targeting solid tumor stem cells within a particular cancer.

The present invention provides an isolated population of cancer stem cells, for example colon or head and neck, obtained from the respective tumor of epithelial origin, wherein the population comprises at least 75% cancer stem cells, colon or head and neck, and less than 25% tumor cells, wherein the colon or head and neck cancer stem cells: are tumorigenic; and are CD44+ compared to non-tumorigenic tumor cells.

The present invention provides an enriched population of cancer stem cells, for example colon or head and neck obtained from the respective tumor of epithelial origin, wherein the population comprises colon or head and neck cancer stem cells and colon or head and neck tumor cells, wherein the cancer stem cells: are enriched at least two-fold compared to unfractionated tumor cells; are tumorigenic; and are CD44+ compared to non-tumorigenic colon tumor cells.

The present invention provides an isolated population of cancer stem cells, for example colon or head and neck, obtained from the respective tumor of epithelial origin, wherein the population comprises at least 75% colon or head and neck cancer stem cells and less than 25% colon or head and neck tumor cells, wherein the colon or head and neck cancer stem cells: are tumorigenic; and express elevated levels of CD166 compared to non-tumorigenic colon tumor cells.

The present invention provides an enriched population of cancer stem cells, for example colon or head and neck obtained from the respective tumor of epithelial origin, wherein the population comprises colon or head and neck cancer stem cells and colon or head and neck tumor cells, wherein the cancer stem cells: are enriched at least two-fold compared to unfractionated tumor cells; are tumorigenic; and are CD166 compared to non-tumorigenic colon tumor cells.

The present invention provides an isolated population of cancer stem cells, for example colon or head and neck, obtained from the respective tumor of epithelial origin, wherein the population comprises at least 75% colon or head and neck cancer stem cells and less than 25% colon or head and neck tumor cells, wherein the colon or head and neck cancer stem cells: are tumorigenic; and express elevated levels of CD49f compared to non-tumorigenic colon tumor cells.

The present invention provides an enriched population of cancer stem cells, for example colon or head and neck obtained from the respective tumor of epithelial origin, wherein the population comprises colon or head and neck cancer stem cells and colon or head and neck tumor cells, wherein the cancer stem cells: are enriched at least two-fold compared to unfractionated tumor cells; are tumorigenic; and are CD49f compared to non-tumorigenic colon tumor cells.

The present invention provides an isolated population of cancer stem cells, for example colon or head and neck, obtained from the respective tumor of epithelial origin, wherein the population comprises at least 75% colon or head and neck cancer stem cells and less than 25% colon or head and neck tumor cells, wherein the colon or head and neck cancer stem cells: are tumorigenic; and express elevated levels of CD59 compared to non-tumorigenic colon tumor cells.

The present invention provides an enriched population of cancer stem cells, for example colon or head and neck obtained from the respective tumor of epithelial origin, wherein the population comprises colon or head and neck cancer stem cells and colon or head and neck tumor cells, wherein the cancer stem cells: are enriched at least two-fold compared to unfractionated tumor cells; are tumorigenic; and are CD59 compared to non-tumorigenic colon tumor cells.

The present invention provides an isolated population of cancer stem cells, for example colon or head and neck obtained from the respective tumor of epithelial origin, wherein the population comprises at least 75% colon or head and neck cancer stem cells and less than 25% colon or head and neck tumor cells, wherein the colon or head and neck cancer stem cells: are tumorigenic; are CD44+, and express elevated levels of CD166 compared to non-tumorigenic colon tumor cells. In certain embodiments, the isolated colon cancer stem cells further express ESA.

The present invention provides an isolated population of cancer stem cells, for example colon or head and neck obtained from the respective tumor of epithelial origin, wherein the population comprises at least 95% colon or head and neck cancer stem cells and less than 5% non-tumorigenic colon or head and neck tumor cells, wherein the colon or head and neck cancer stem cells are both tumorigenic and express elevated levels of CD166 compared to non-tumorigenic colon tumor cells.

The present invention provides an isolated population of colon cancer stem cells obtained from a colon tumor of epithelial origin, wherein the population comprises at least 75% colon cancer stem cells and less than 25% colon tumor cells, wherein the colon cancer stem cells: are tumorigenic; and express elevated levels of one or more of PTGFRN, CD166, CD164, CD82, TGFBR1, MET, EFNB2, ITGA6, TDGF1, HBEGF, ABCC4, ABCD3, TDE2, ITGB1, TNFRSF21, CD81, CD9, KIAA1324, CEACAM6, FZD6, FZD7, BMPR1A, JAG1, ITGAV, NOTCH2, SOX4, The present invention provides an isolated population of cancer stem cells obtained from a tumor of epithelial origin, wherein the population comprises at least 75% cancer stem cells and less than 25% tumor cells, wherein the cancer stem cells: are tumorigenic; are CD44+; and express elevated levels of one or more of PTGFRN, CD166, CD164, CD82, TGFBR1, MET, EFNB2, ITGA6, TDGF1, HBEGF, ABCC4, ABCD3, TDE2, ITGB1, TNFRSF21, CD81, CD9, KIAA1324, CEACAM6, FZD6, FZD7, BMPR1A, JAG1, ITGAV, NOTCH2, SOX4, HES1, HES6, ATOH1, CDH1, EPHB2, MYB, MYC, SOX9 or STRAP, or lower levels of one or more of TCF4 or VIM, compared to non-tumorigenic tumor cells. In certain embodiments, the isolated cancer stem cells further express ESA. In certain embodiments, the isolated cancer stem cells are colon cancer stem cells. In certain embodiments, the isolated cancer stem cells are head and neck cancer stem cells.

The present invention provides an isolated population of cancer stem cells obtained from a tumor of epithelial origin, wherein the population comprises at least 95% cancer stem cells and less than 5% non-tumorigenic tumor cells, wherein the cancer stem cells: are tumorigenic, are CD44+, and express elevated levels of one or more of PTGFRN, CD166, CD164, CD82, TGFBR1, MET, EFNB2, ITGA6, TDGF1, HBEGF, ABCC4, ABCD3, TDE2, ITGB1, TNFRSF21, CD81, CD9, KIAA1324, CEACAM6, FZD6, FZD7, BMPR1A, JAG1, ITGAV, NOTCH2, SOX4, HES1, HES6, ATOH1, CDH1, EPHB2, MYB, MYC, SOX9 or STRAP, or lower levels of one or more of TCF4 or VIM, compared to non-tumorigenic tumor cells. In certain embodiments, the isolated cancer stem cells further express ESA. In certain embodiments, the isolated cancer stem cells are colon cancer stem cells. In certain embodiments, the isolated cancer stem cells are head and neck cancer stem cells.

The present invention provides an enriched population of cancer stem cells obtained from a tumor of epithelial origin, wherein the population comprises cancer stem cells and tumor cells, wherein the cancer stem cells: are enriched at least two-fold compared to unfractionated tumor cells; are tumorigenic; are CD44+; and express elevated levels of one or more of PTGFRN, CD166, CD164, CD82, TGFBR1, MET, EFNB2, ITGA6, TDGF1, HBEGF, ABCC4, ABCD3, TDE2, ITGB1, TNFRSF21, CD81, CD9, KIAA1324, CEACAM6, FZD6, FZD7, BMPR1A, JAG1, ITGAV, NOTCH2, SOX4, HES1, HES6, ATOH1, CDH1, EPHB2, MYB, MYC, SOX9 or STRAP, or lower levels of either or both of TCF4 or VIM, compared to non-tumorigenic tumor cells. In certain embodiments, the enriched cancer stem cells further express ESA. In certain embodiments, the isolated cancer stem cells are colon cancer stem cells. In certain embodiments, the isolated cancer stem cells are head and neck cancer stem cells.

The present invention provides an enriched population of cancer stem cells obtained from a tumor of epithelial origin, wherein the population comprises cancer stem cells and tumor cells, wherein the cancer stem cells: are enriched at least five-fold compared to unfractionated tumor cells; are tumorigenic; are CD44+, and express elevated levels of one or more of PTGFRN, CD166, CD164, CD82, TGFBR1, MET, EFNB2, ITGA6, TDGF1, HBEGF, ABCC4, ABCD3, TDE2, ITGB1, TNFRSF21, CD81, CD9, KIAA1324, CEACAM6, FZD6, FZD7, BMPR1A, JAG1, ITGAV, NOTCH2, SOX4, HES1, HES6, ATOH1, CDH1, EPHB2, MYB, MYC, SOX9 or STRAP, or lower levels of either or both of TCF4 or VIM, compared to non-tumorigenic tumor cells. In certain embodiments, the isolated cancer stem cells are colon cancer stem cells. In certain embodiments, the isolated cancer stem cells are head and neck cancer stem cells.

The present invention provides methods for obtaining from a tumor a cellular composition comprising cancer stem cells and non-tumorigenic tumor cells, wherein at least 75% are tumorigenic stem cells and 25% or less are non-tumorigenic tumor cells, said method comprising: (a) obtaining a dissociated mixture of tumor cells from a tumor of epithelial origin; (b) separating the mixture of tumor cells into a first fraction comprising at least 75% cancer stem cells and 25% or less non-tumorigenic tumor cells and a second fraction of tumor cells depleted of cancer stem cells wherein the separating is by contacting the mixture with one or more reagents, including for example CD44 and ESA; and (c) demonstrating the first fraction to be tumorigenic by serial injection into a host animal and the second fraction to be non-tumorigenic by serial injection into the host animal. In certain embodiments the separating is performed by flow cytometry, fluorescence activated cell sorting (FACS), panning, affinity chromatography or magnetic selection. In certain embodiments the separating is performed by fluorescence activated cell sorters (FACS) analysis.

The present invention provides methods for obtaining from a tumor a cellular composition comprising cancer stem cells and non-tumorigenic tumor cells, wherein at least 75% are tumorigenic stem cells and 25% or less are non-tumorigenic tumor cells, said method comprising: (a) obtaining a dissociated mixture of tumor cells from a tumor of epithelial origin; (b) separating the mixture of tumor cells into a first fraction comprising at least 75% cancer stem cells and 25% or less non-tumorigenic tumor cells and a second fraction of tumor cells depleted of cancer stem cells wherein the separating is by contacting the mixture with reagents against CD44 and ESA; and (c) demonstrating the first fraction to be tumorigenic by serial injection into a host animal and the second fraction to be non-tumorigenic by serial injection into the host animal. In certain embodiments the separating is performed by flow cytometry, fluorescence activated cell sorting (FACS), panning, affinity chromatography or magnetic selection. In certain embodiments the separating is performed by fluorescence activated cell sorters (FACS) analysis.

The present invention provides methods for enriching a population of cancer stem cells from a tumor of epithelial origin wherein the enriched population comprises 75% cancer stem cells and 25% or less non-tumorigenic tumor cells, said method comprising: (a) obtaining a dissociated mixture of tumor cells from a tumor of epithelial origin; (b) contacting the mixture of tumor cells with one or more reagents, including for example CD44 and ESA; (c) selecting a first fraction of cancer stem cells by their binding to the reagents and a second fraction of tumor cells depleted of cancer stem cells; and (d) demonstrating the first fraction to be tumorigenic by serial injection of the tumor stem cells into a host animal and the second fraction to be non-tumorigenic by serial injection into the host animal. In certain embodiments the selecting is performed by flow cytometry, fluorescence activated cell sorting (FACS), panning, affinity chromatography or magnetic selection. In certain embodiments the selecting is performed by fluorescence activated cell sorters (FACS) analysis.

The present invention provides the means and methods for enriching a population of cancer stem cells from a colon tumor of epithelial origin wherein the enriched population comprises 75% cancer stem cells and 25% or less non-tumorigenic tumor cells, said method comprising: (a) obtaining a dissociated mixture of tumor cells from a tumor of epithelial origin; (b) contacting the mixture of tumor cells with reagents against CD44 and ESA; (c) selecting a first fraction of cancer stem cells by their binding to the reagents and a second fraction of tumor cells depleted of cancer stem cells; and (d) demonstrating the first fraction to be tumorigenic by serial injection of the tumor stem cells into a host animal and the second fraction to be non-tumorigenic by serial injection into the host animal. In certain embodiments the selecting is performed by flow cytometry, fluorescence activated cell sorting (FACS), panning, affinity chromatography or magnetic selection. In certain embodiments the selecting is performed by fluorescence activated cell sorters (FACS) analysis.

The present invention provides an isolated population of cancer stem cells obtained from a tumor of epithelial origin, wherein the population comprises at least 75% cancer stem cells and less than 25% tumor cells, wherein the cancer stem cells: are tumorigenic; are CD44+, and display elevated levels of ALDH activity compared to non-tumorigenic tumor cells. In certain embodiments, the isolated cancer stem cells further express ESA. In certain embodiments, the isolated cancer stem cells are colon cancer stem cells. In certain embodiments, the isolated cancer stem cells are head and neck cancer stem cells.

The present invention provides an enriched population of cancer stem cells obtained from a tumor of epithelial origin, wherein the population comprises cancer stem cells and tumor cells, wherein the cancer stem cells: are enriched at least two-fold compared to unfractionated tumor cells; are tumorigenic; are CD44+; and display elevated levels of ALDH activity compared to non-tumorigenic tumor cells. In certain embodiments, the enriched cancer stem cells further express ESA. In certain embodiments, the isolated cancer stem cells are colon cancer stem cells. In certain embodiments, the isolated cancer stem cells are head and neck cancer stem cells.

The present invention provides a method of identifying the presence of cancer stem cells in a subject suspected of having cancer, wherein the method comprises: (a) obtaining a biological sample from the subject; (b) dissociating cells of the sample; (c) contacting the dissociated cells with a first reagent that binds CD44 and a second reagent that binds CD166; and (d) detecting cancer stem cells that bind to the first and second reagent. In certain embodiments, the first or second reagent is an antibody. In certain embodiments, the detection step is performed by flow cytometry, fluorescence activated cell sorting, panning, affinity column separation, or magnetic selection. In certain embodiments, the cancer stem cells are colon cancer stem cells. In certain embodiments, the cancer stem cells are head and neck cancer stem cells.

The present invention provides a method of identifying the presence of cancer stem cells in a subject suspected of having cancer, wherein the method comprises: (a) obtaining a biological sample from the subject; (b) dissociating cells of the sample; (c) contacting the dissociated cells with a first reagent that binds CD44 and a second reagent that detects ALDH activity; and (d) detecting cancer stem cells that bind to the first reagent and that show increased ALDH activity. In certain embodiments, the first reagent is an antibody. In certain embodiments, the detection step is performed by flow cytometry, fluorescence activated cell sorting, panning, affinity column separation, or magnetic selection. In certain embodiments, the cancer stem cells are colon cancer stem cells. In certain embodiments, the cancer stem cells are head and neck cancer stem cells.

BRIEF DESCRIPTION OF THE DRAWINGS/FIGURES

FIG. 1: FACS Sorting of a Population of Tumor Cells Containing Tumor Stem Cell Activity. (A, B) Subpopulations of tumor cells from a human colorectal cancer were passaged through immunodeficient mice, depleted of mouse-derived cells using anti-mouse $H2K^d$ and CD45 antibodies, and isolated based on expression of ESA and CD44. Cells positive for both cell surface markers (TG; top gate; red) are tumorigenic (see FIG. 2 & Table 2) and were compared by microarray analysis to non-tumorigenic cells (NTG; blue).

Figure 2:
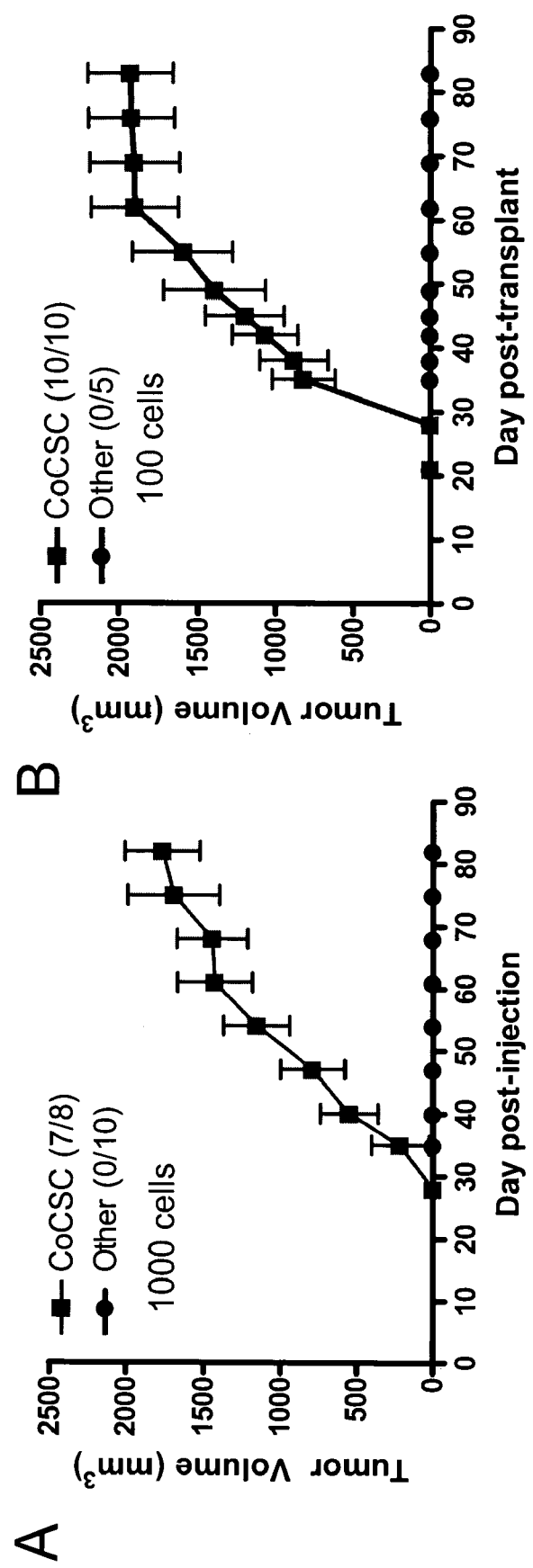

FIG. 2: ESA+44+ Colon Tumor Cells are Tumorigenic. ESA+44+ colon cancer stem cells (CoCSC) versus non-ESA+44+ colon tumor cells (Other) were isolated by FACS and injected subcutaneously into immunodeficient mice at cell doses of approximately A) 1000 or B) 100 cells per animal. Mean±SEM tumor volume for each dose is plotted. After 80+ days, tumor volume continued to increase in mice injected with CoCSC but tumors never developed in mice injected with non-ESA+44+ colon tumor cells (Other).

Figure 3:
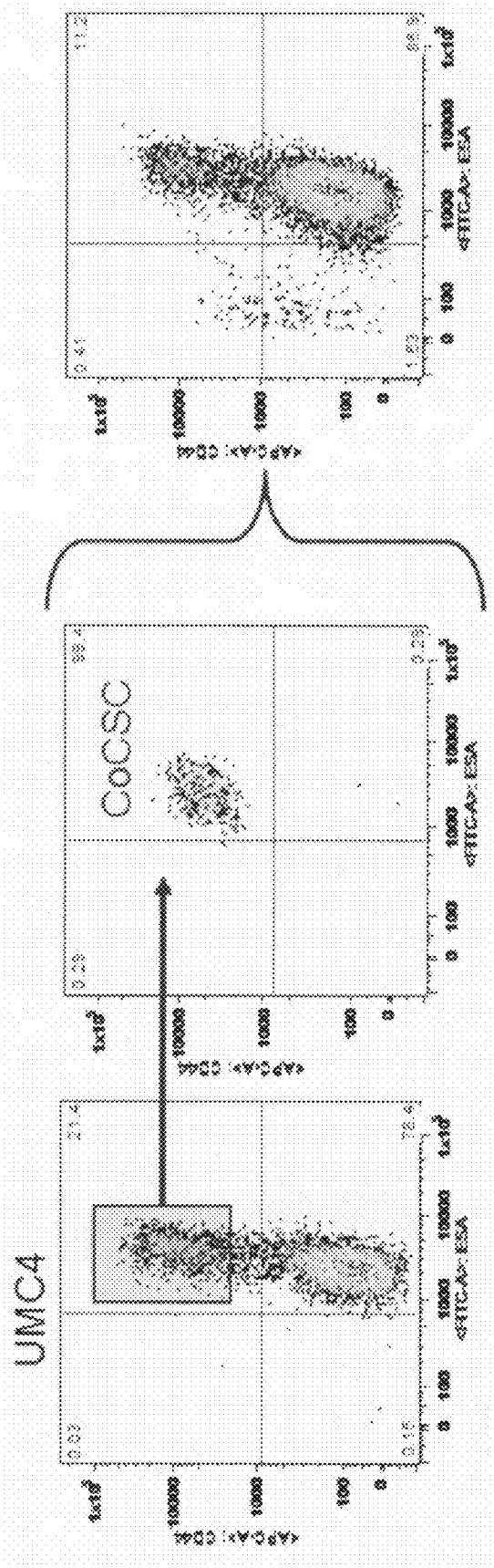

FIG. 3: Tumors generated by Colon Cancer Stem Cells Retain their Phenotypic Identity. A flow cytometry profile of colon tumor cells shows expression of ESA and CD44 (left). ESA+44+ colon cancer stem cells are isolated (middle) by FACS and injected into immunodeficient mice. When the tumors generated in mice from these purified CoCSC are reanalyzed for the expression of ESA and CD44, the tumor phenotype is identical to that of the original heterogeneous tumor (right).

Figure 4:
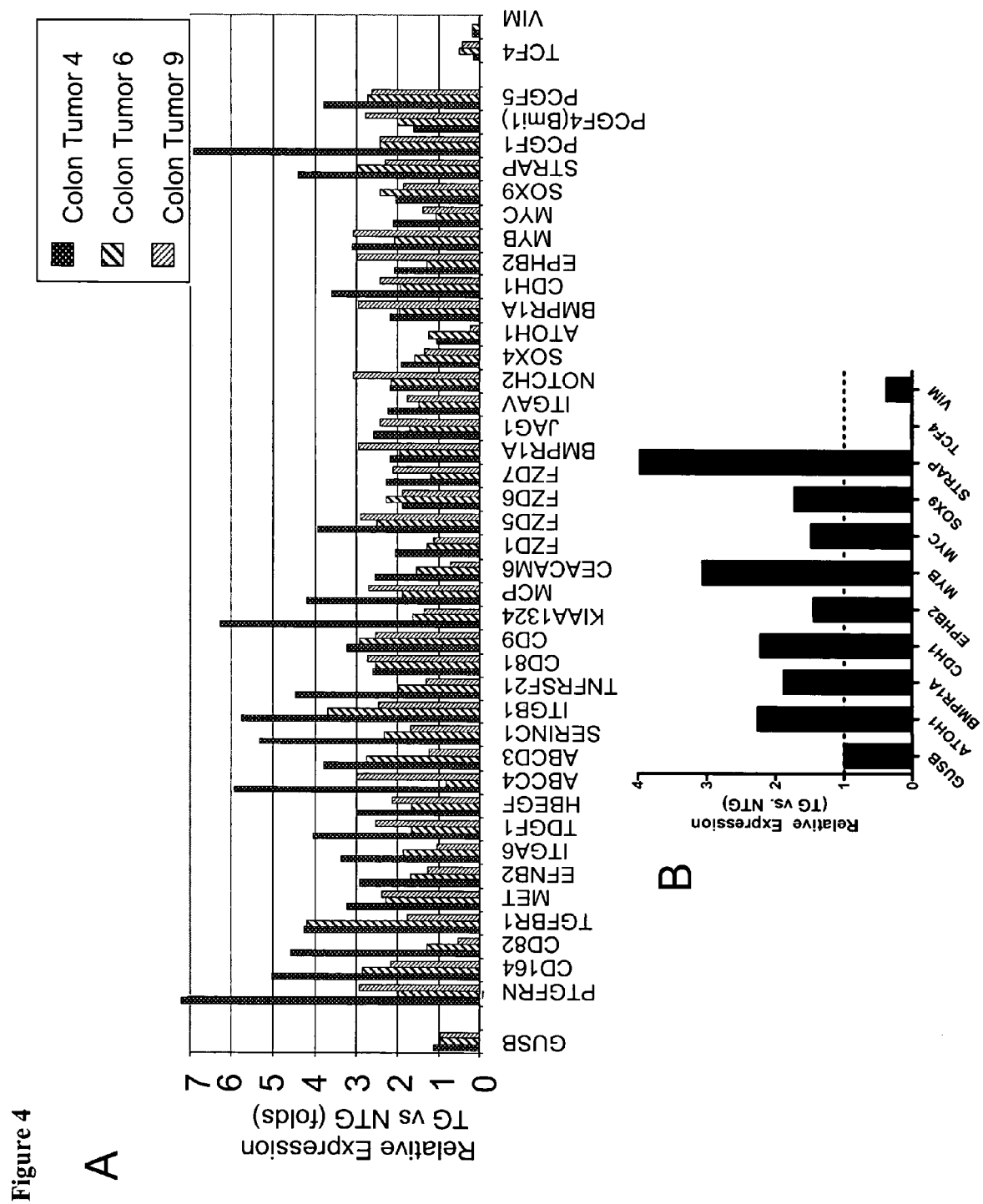

FIG. 4: Genes Differentially Expressed in Colon Cancer Stem Cells. A) The fold relative expression of different genes, as determined by microarray analysis, in ESA+44+ tumorigenic (TG) colon cancer stem cells versus non-tumorigenic (NTG) sorted tumor cells is graphed. B) Relative gene expression of targets was validated by Taqman quantitative RT-PCR using FACS-purified TG versus NTG UM-C4 colon cancer cells. Results were normalized versus an internal control (i.e. GUSB) prior to relative expression analysis.

Figure 5:
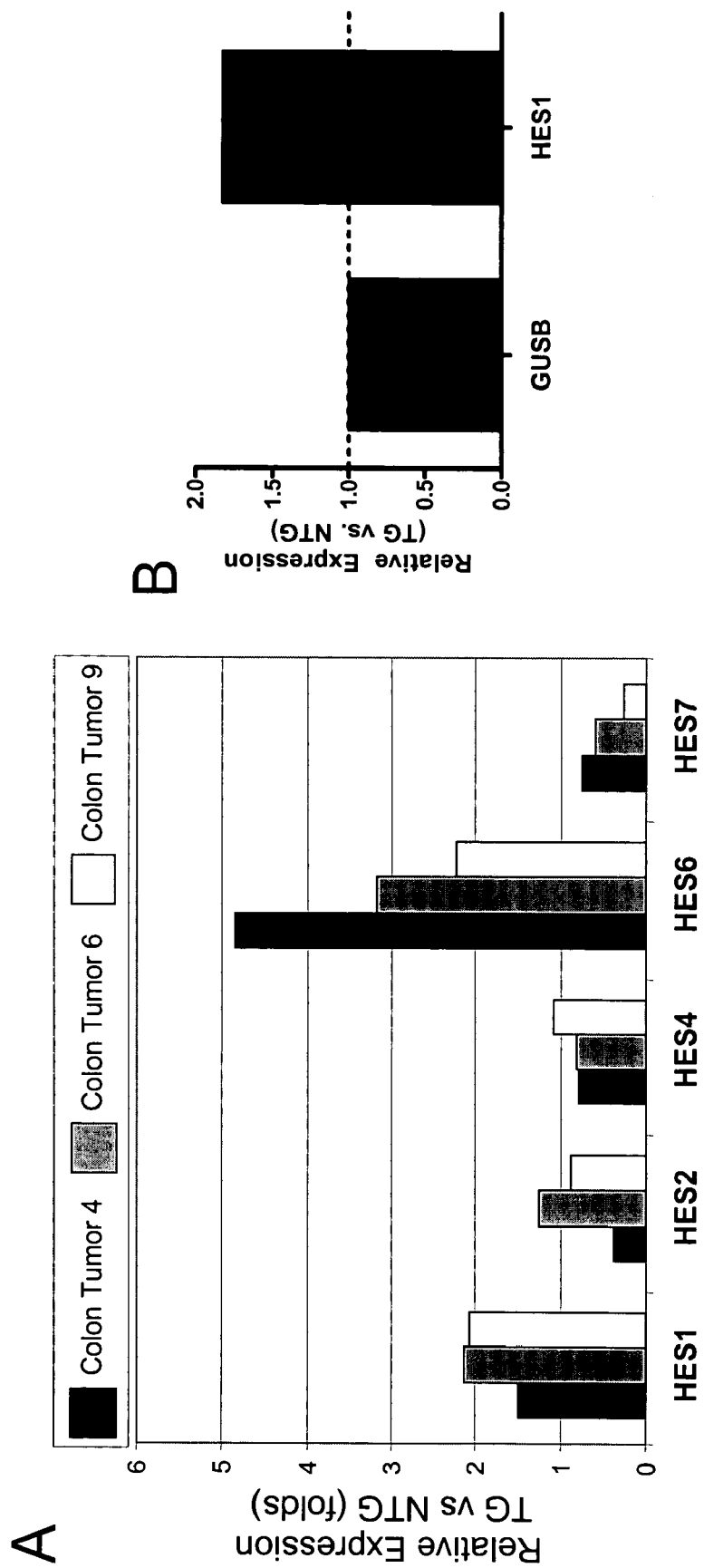

FIG. 5: Differential Expression of Hes1 and Hes6 in Colon Cancer Stem Cells. The relative expression of different Hes genes in ESA+44+ colon cancer stem cells versus non-tumorigenic sorted tumor cells is shown. A) In contrast to HES2, 4 and 7, HES1 & 6 show increased expression in colon cancer stem cells versus non-tumorigenic sorted tumor cells. B) Relative expression of HES1 was validated by Taqman quantitative RT-PCR using FACS-purified TG versus NTG UM-C4 colon cancer cells. Results were normalized versus an internal control (i.e. GUSB) prior to relative expression analysis.

Figure 6:
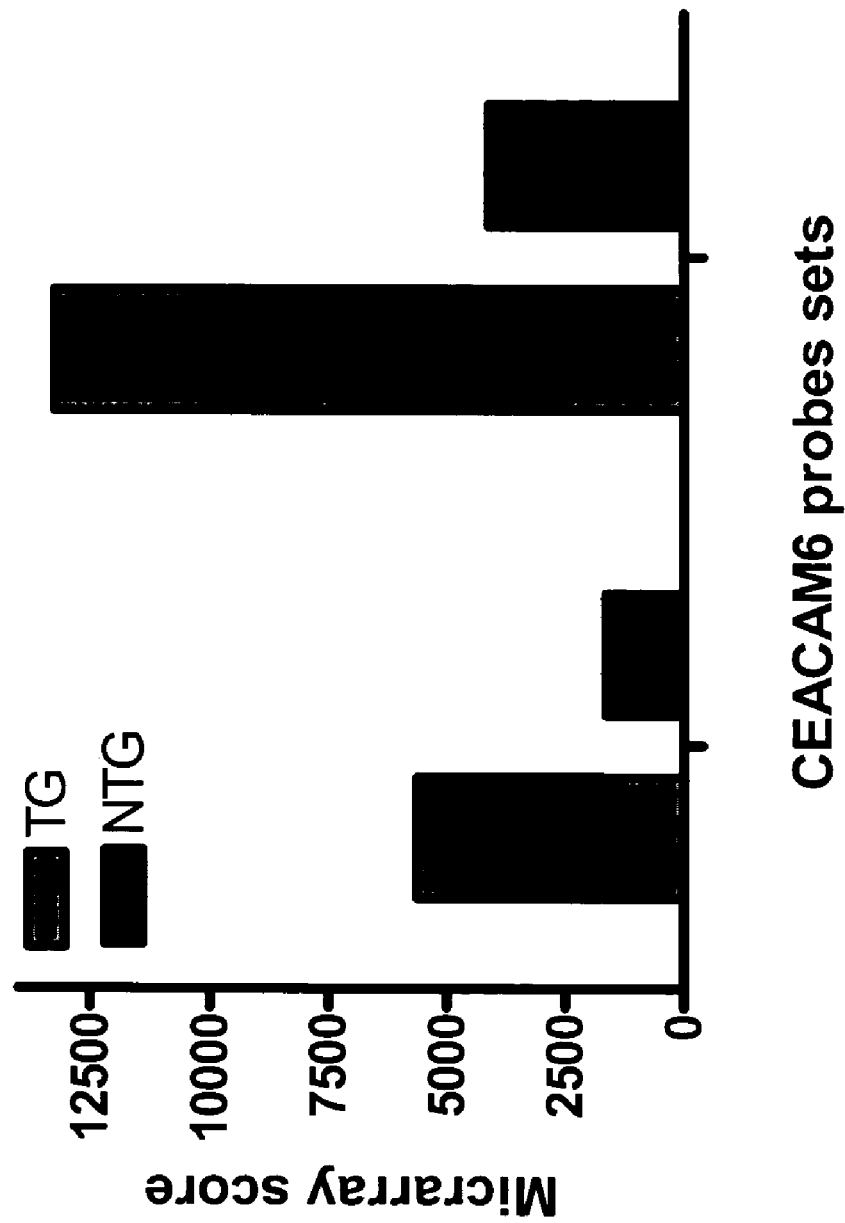

FIG. 6: Differential Expression CEACAM6 in Tumorigenic Colon Cells. Absolute expression by Affymetrix array analysis of CEACAM6 in ESA+44+ colon cancer stem cells (TG) compared to non-tumorigenic tumor cells (NTG).

Figure 7:
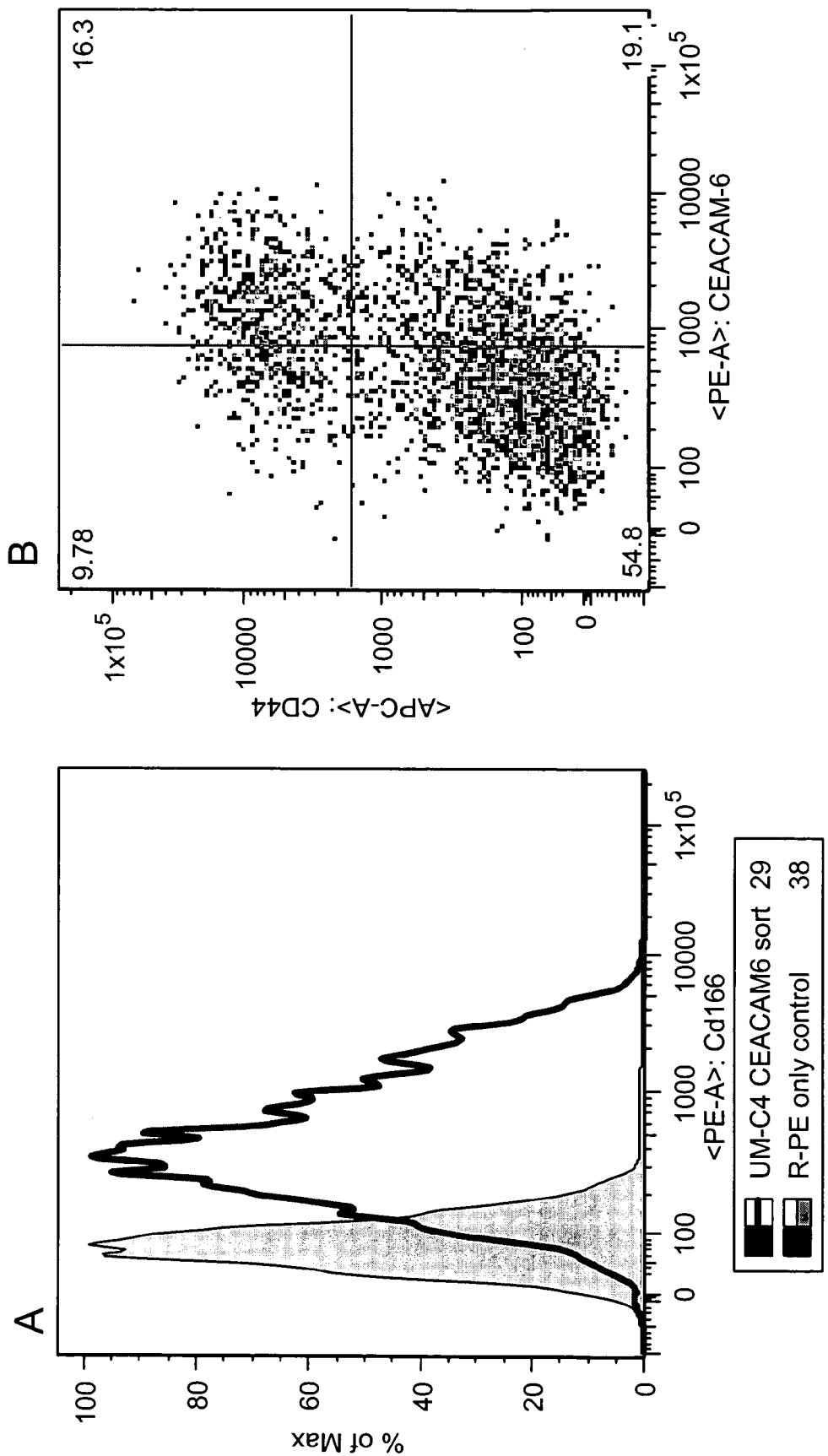

FIG. 7: Expression of CEACAM6 by Colon Tumor Cells. A) Flow cytometry analysis of colon tumor cells, demonstrating expression profile of CEACAM6. B) Flow cytometry profile of colon tumors, showing expression of CD44 and CEACAM6 by ESA+ colon tumor cells. Roughly 62% of ESA+44+ cells are also CEACAM6 positive.

Figure 8:
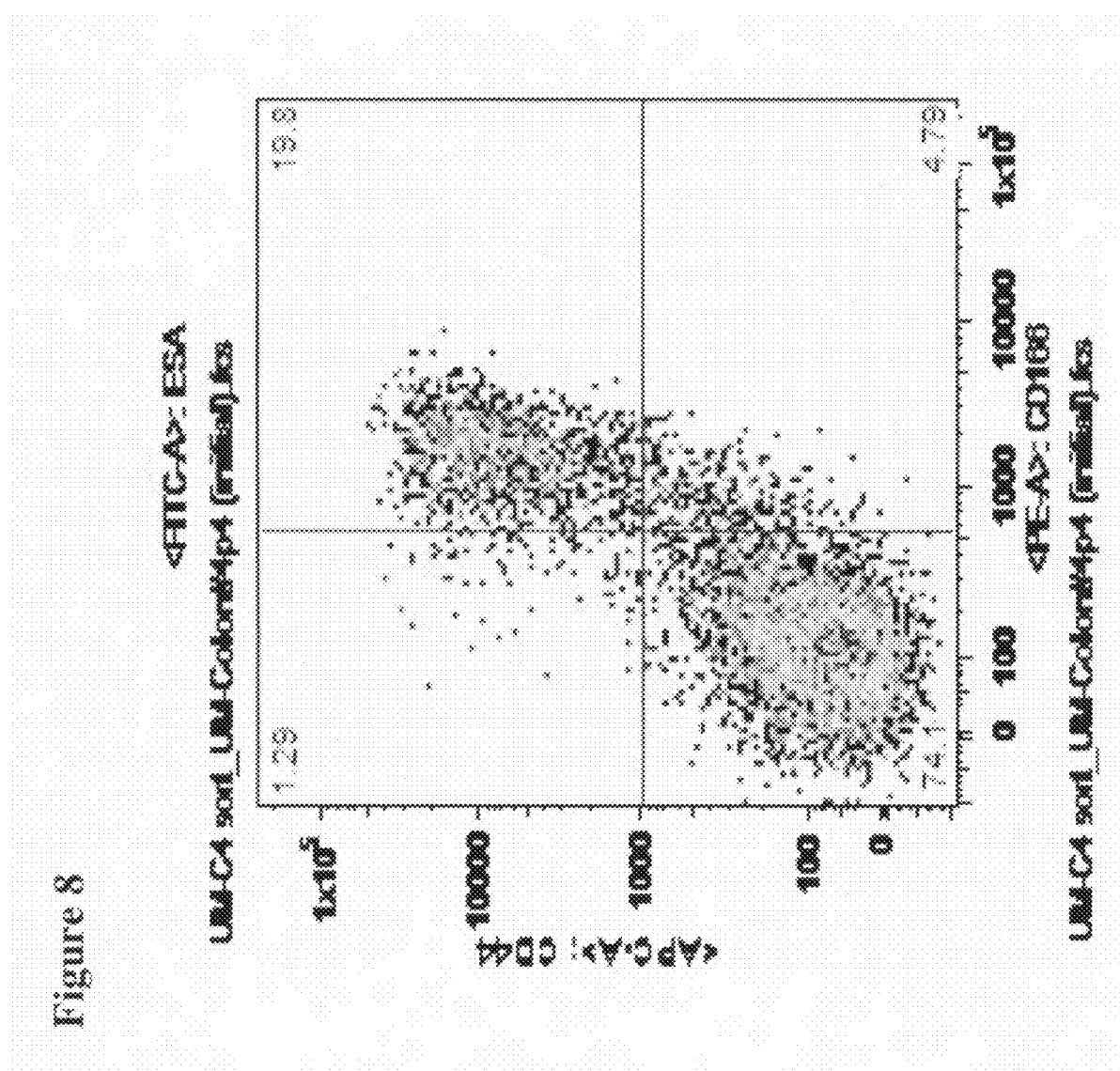

FIG. 8: Expression of CD166 by Colon Tumor Cells. A flow cytometry profile showing expression of CD44 and CD166 by ESA+ colon tumor cells. Roughly 94% of ESA+ 44+ cells are also CD166 positive.

Figure 9:
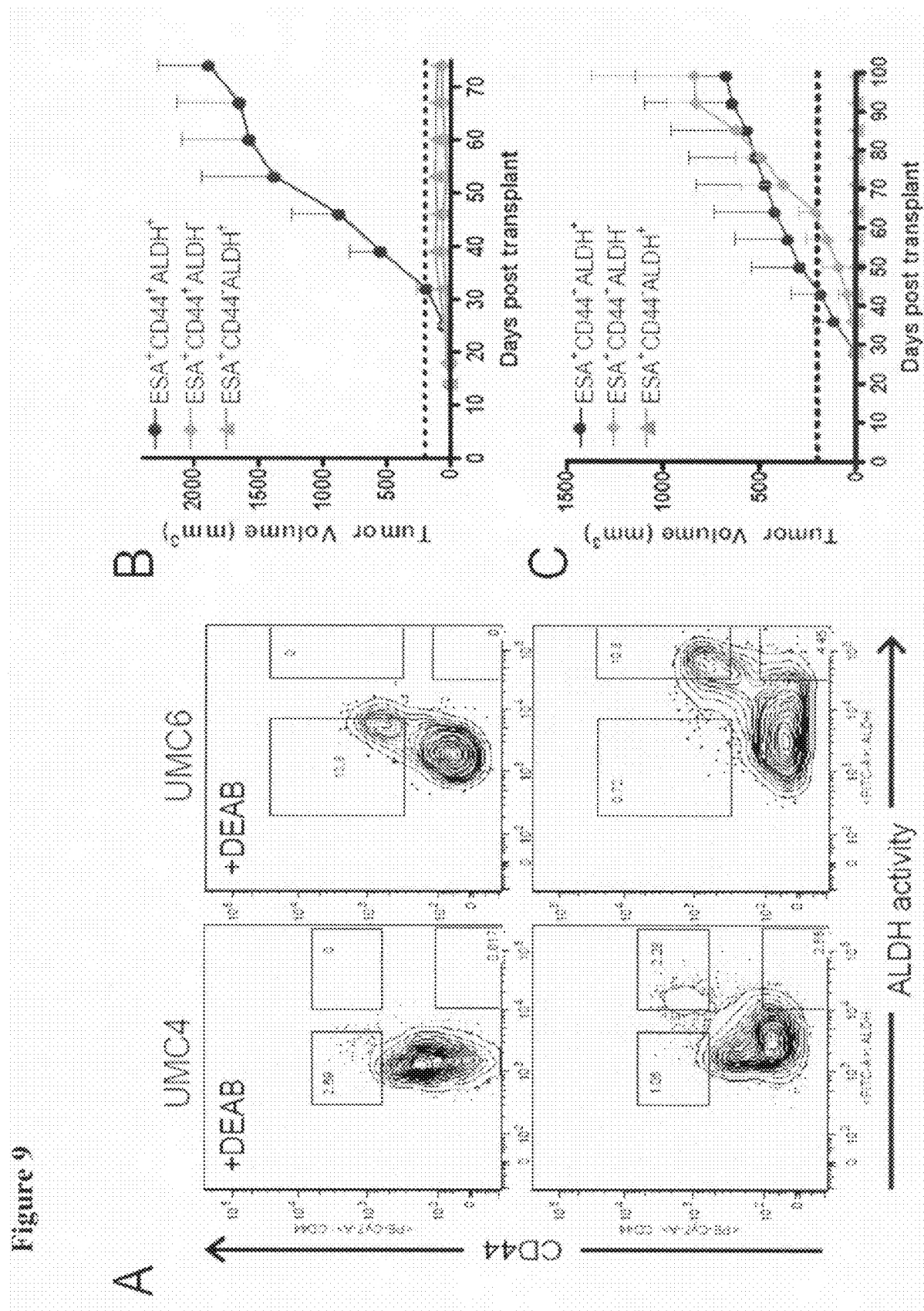

FIG. 9: The Majority of CD44+ Cells have Elevated ALDH Activity. A) CD44/Aldefluor™ flow cytometry profile of mouse lineage-negative (mLin−; $H2K^d$ and murine CD45), ESA+ xenogeneic UM-C4 and UM-C6 colon tumor cells in the presence or absence of the ALDH1 inhibitor, DEAB. Tumor growth curves are shown for the denoted FACS purified populations from B) UM-C4 and C) UM-C6 tumors injected at a dose of 500 cells subcutaneously. Means±SEM are plotted and reflect only those mice with palpable tumors.

Figure 10:
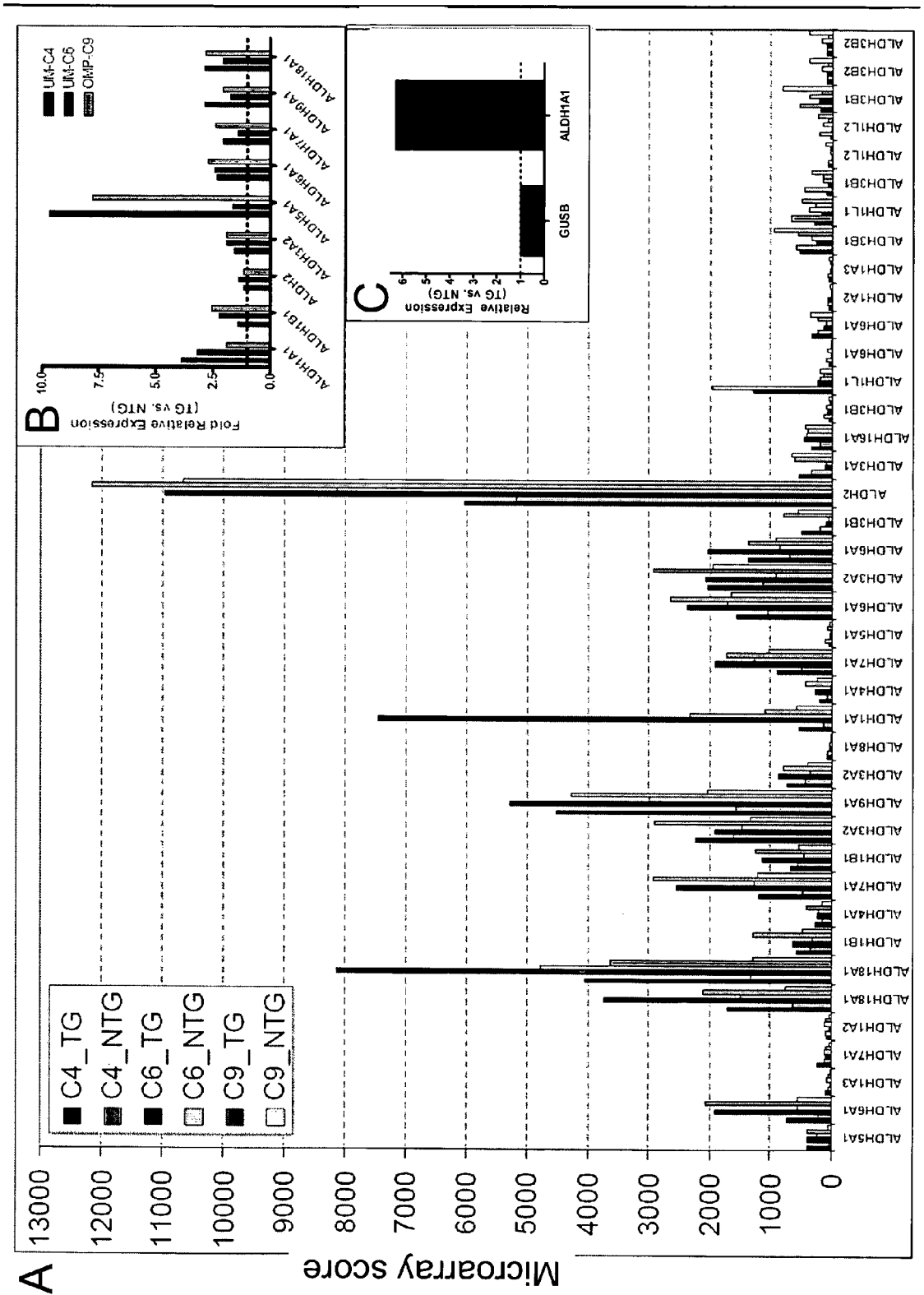

FIG. 10: Relative ALDH Gene Family Expression. A) Absolute expression levels of ALDH family member mRNA as determined by Affymetrix microarry analysis is shown. B) Inset shows the relative expression of several ALDH genes in TG versus NTG cells from different colon tumor xenografts. C) Inset shows relative expression of ALDH1A1 as validated by Taqman quantitative RT-PCR using FACS-purified TG versus NTG cells. Results were normalized versus an internal control (i.e. GUSB) prior to relative expression analysis.

Figure 11:
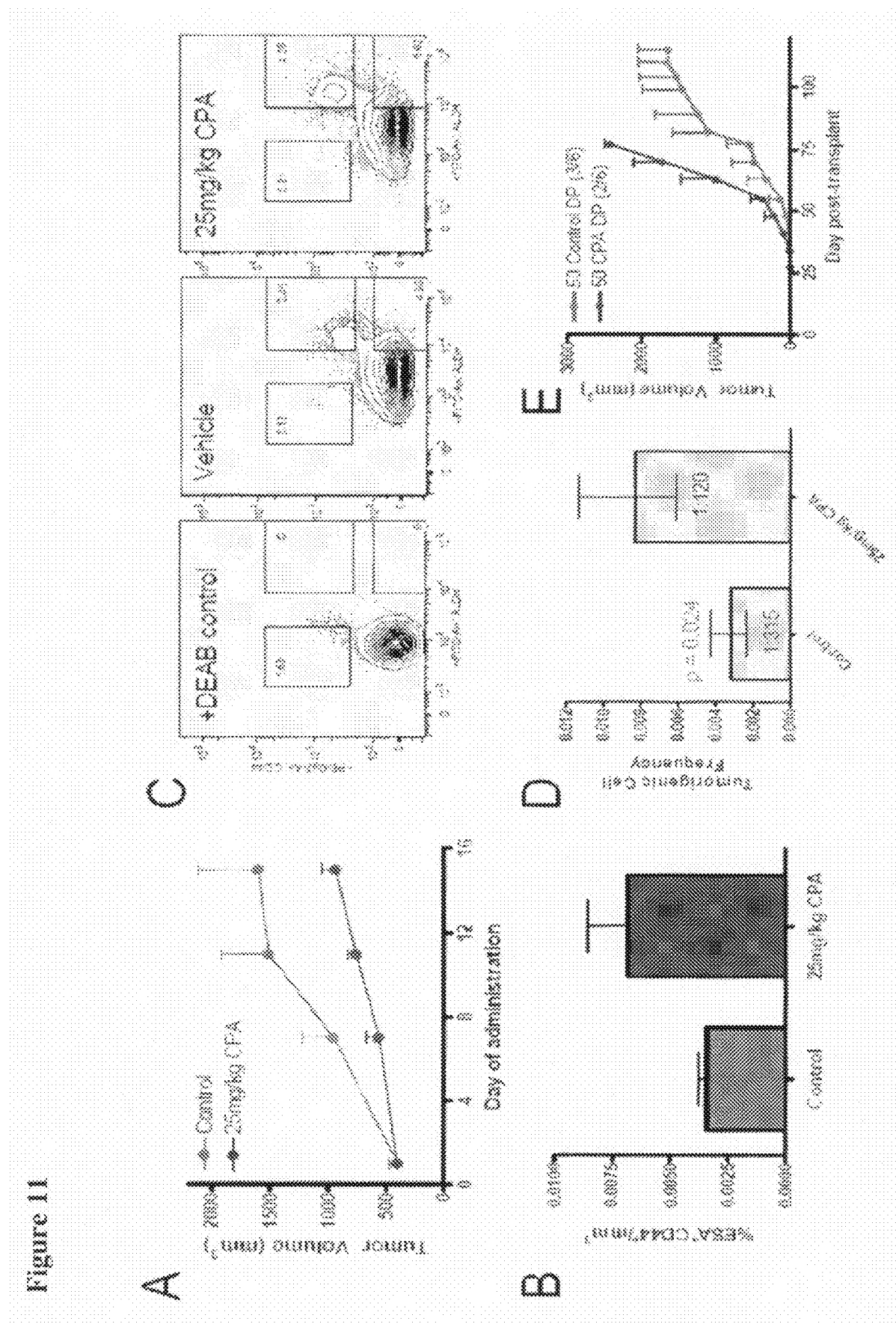

FIG. 11: Tumorigenic UM-C4 Cells Preferentially Survive CPA Chemotherapy. A) Twice weekly administration of 25 mg/kg CPA resulted in delayed UM-C4 tumor growth versus control, vehicle-treated mice. Phenotypic analysis of residual tumors at day fifteen demonstrated B) higher concentrations of ESA+CD44+ cells and C) an increased percentage of cells with ALDH activity. D) Limiting dilution analysis of unfractionated UM-C4 tumor cells demonstrated a significant increase in tumorigenic cell frequency. E) Though ESA+ CD44+ cells were equally tumorigenic, tumors were more aggressive when obtained from CPA compared to control tumors.

Figure 12:
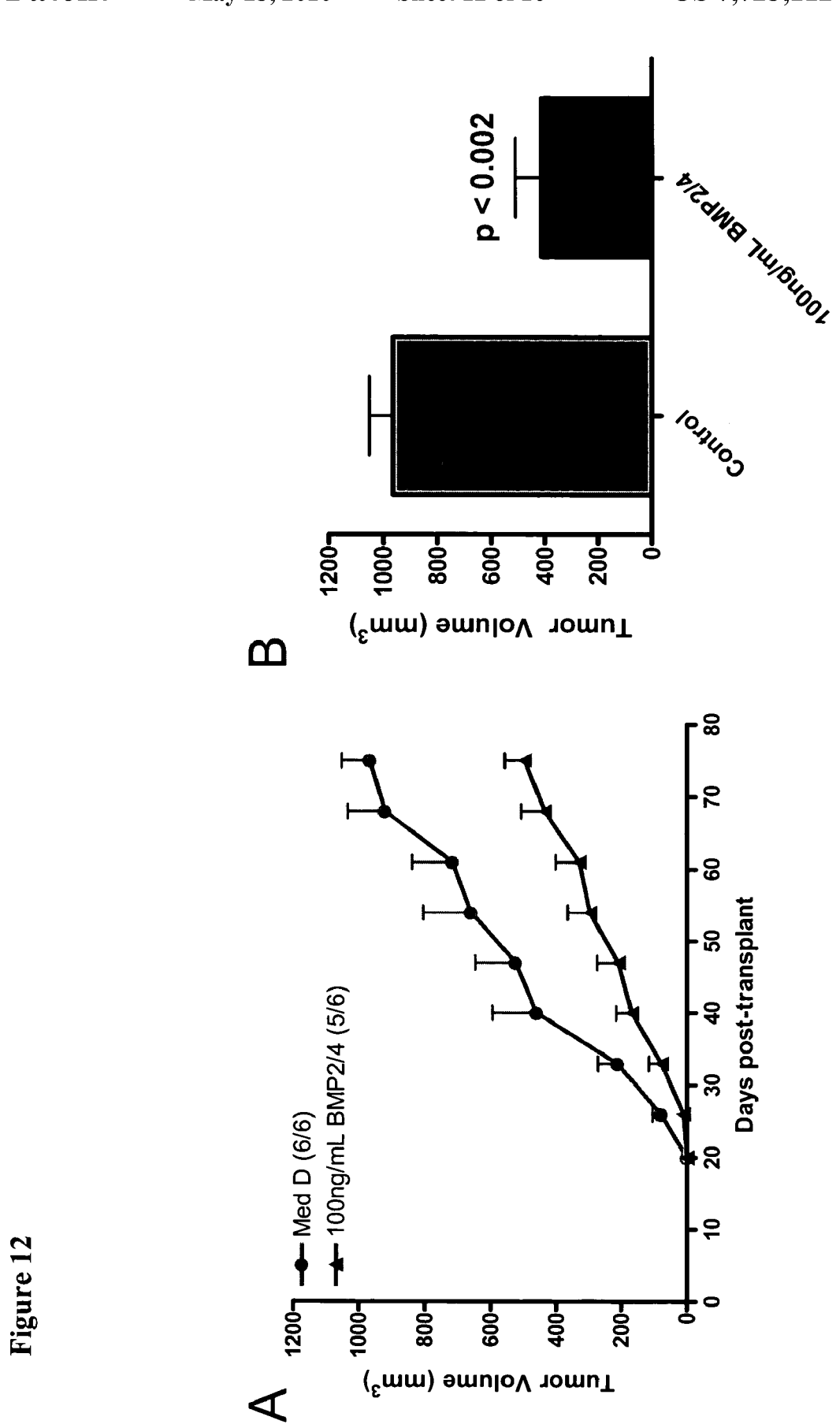

FIG. 12: In Vitro Exposure to BMPs Reduces Tumorigenicity of UM-C6 colon cancer cells. Mouse lineage-negative (mLin−; H2 $K^d$ and murine CD45) cells were plated on laminin-coated coverslips and cultured in the presence of absence of 100 ng/mL BMP2 and BMP4 for 6 days, then harvested and injected subcutaneously into mice to determine tumorigenicity. A) Tumor frequency is shown (in parentheses) for control (Med D) and BMP-exposed (BMP2/4) tumor cells and the Means±SEM are plotted to reflect only those mice with palpable tumors. B) The final measurement of all tumors at day 75 demonstrated a significant reduction in tumor growth following exposure to BMPs.

Figure 13:
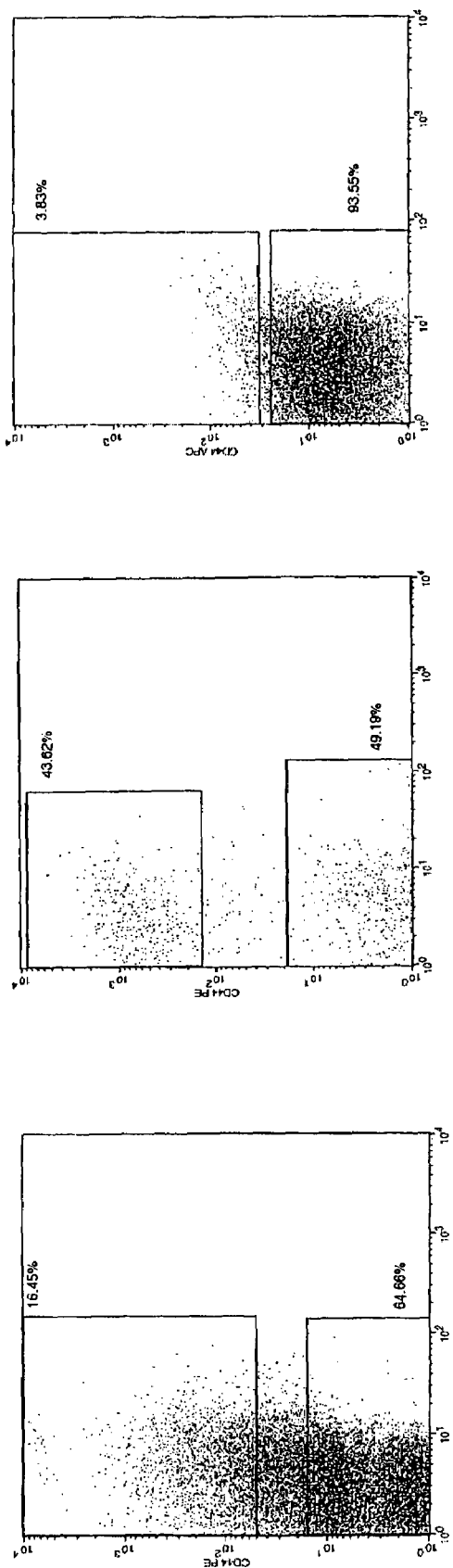

FIG. 13: Head and Neck Cancer Stem Cells. Shown are representative plots revealing the phenotypic diversity in tumors arising from CD44+Lin− cells in UMHN2. The plots depict the CD44 staining pattern of live cancer cells from (a) primary unpassaged tumor, (b) tumor resulting from the implantation of CD44⁺ Lin− cells from the primary tumor (once passaged tumor) and (c) tumor resulting from the implantation of CD44⁺ Lin− cells from the once passaged tumor.

Figure 14:
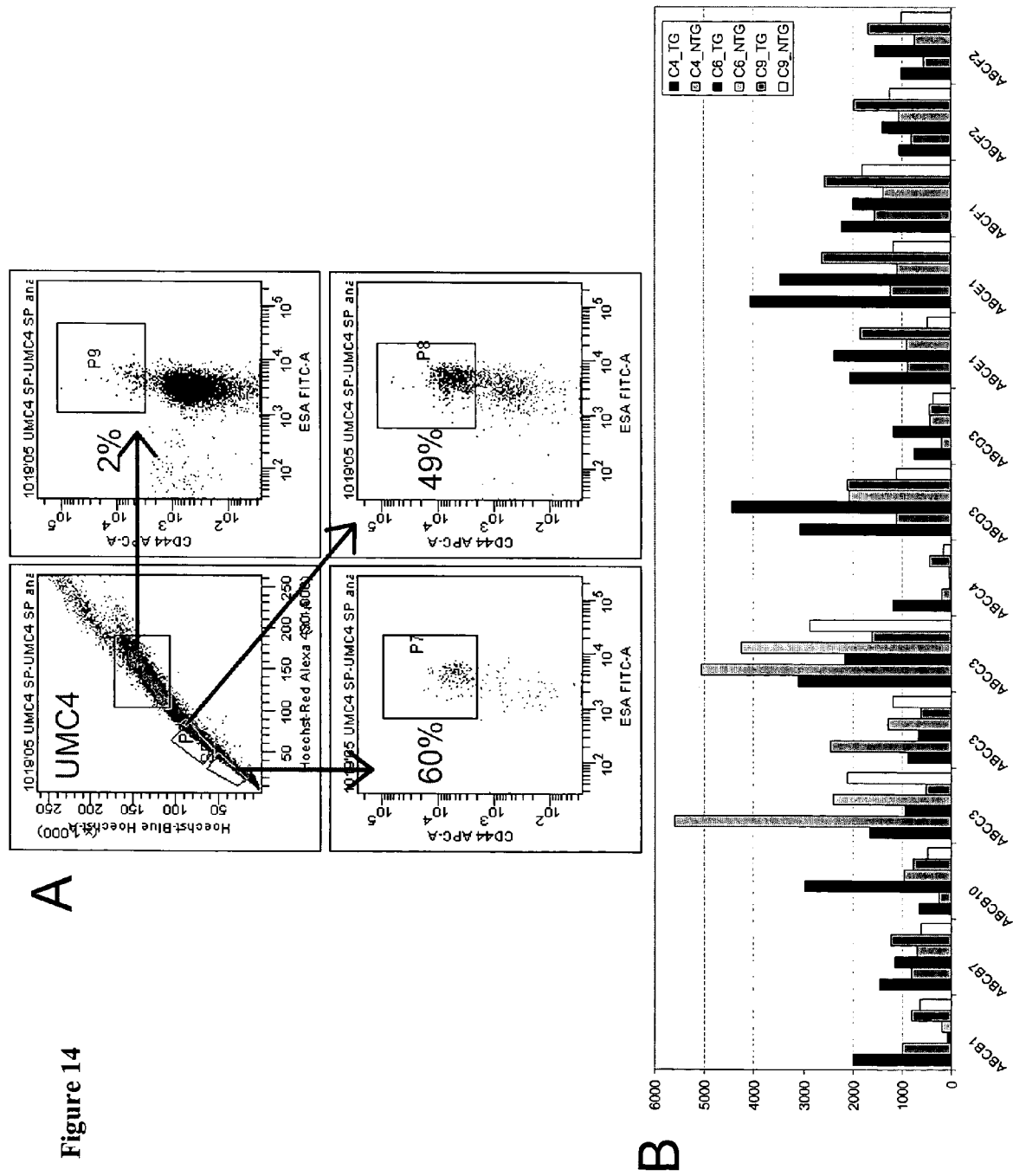

FIG. 14: Side population (SP) Enriches for Colon Cancer Stem Cells. A) SP phenotype cells (red) are enriched for colon cancer stem cells compared to SP-intermediate cells (green) and non-SP cells (dark blue). B) Microarray analysis revealed that tumorigenic (TG) mouse lineage-negative (mLin−), ESA+ xenogeneic UMC4 (C4), UMC6 (C6), and OMP-C9 (C9) colon tumor cells have elevated levels of ABC family member transporter mRNA compared to non-tumorigenic (NTG) cells.

Figure 15:
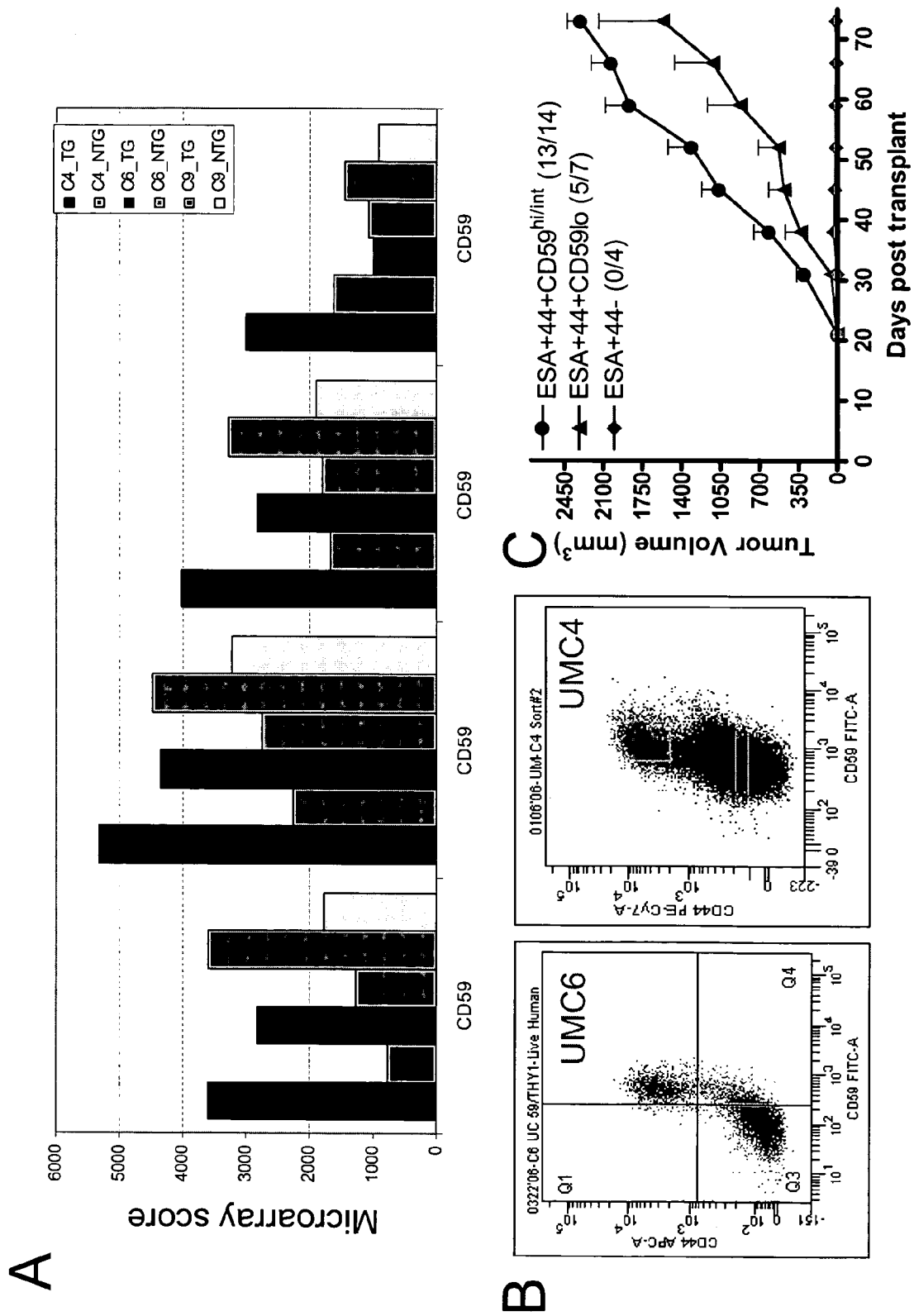

FIG. 15: CD59 Enriches for Colon Cancer Stem Cells. A) By microarray, tumorigenic (TG) mouse lineage-negative (mLin−), ESA+ xenogeneic UMC4, UMC6, and OMP-C9 colon tumor cells have elevated levels of CD59 mRNA compared to non-tumorigenic (NTG) cells. B) Colon tumor cells have elevated CD59 surface expression, which is preferentially found on CD44+ cells. C) A tumor growth curve is shown for the denoted FACS purified populations from ESA+ CD44+ cells further enriched based on CD59 expression. Means±SEM are plotted and reflect only those mice with palpable tumors. Tumor frequency is shown in parentheses and in Table 4.

Figure 16:
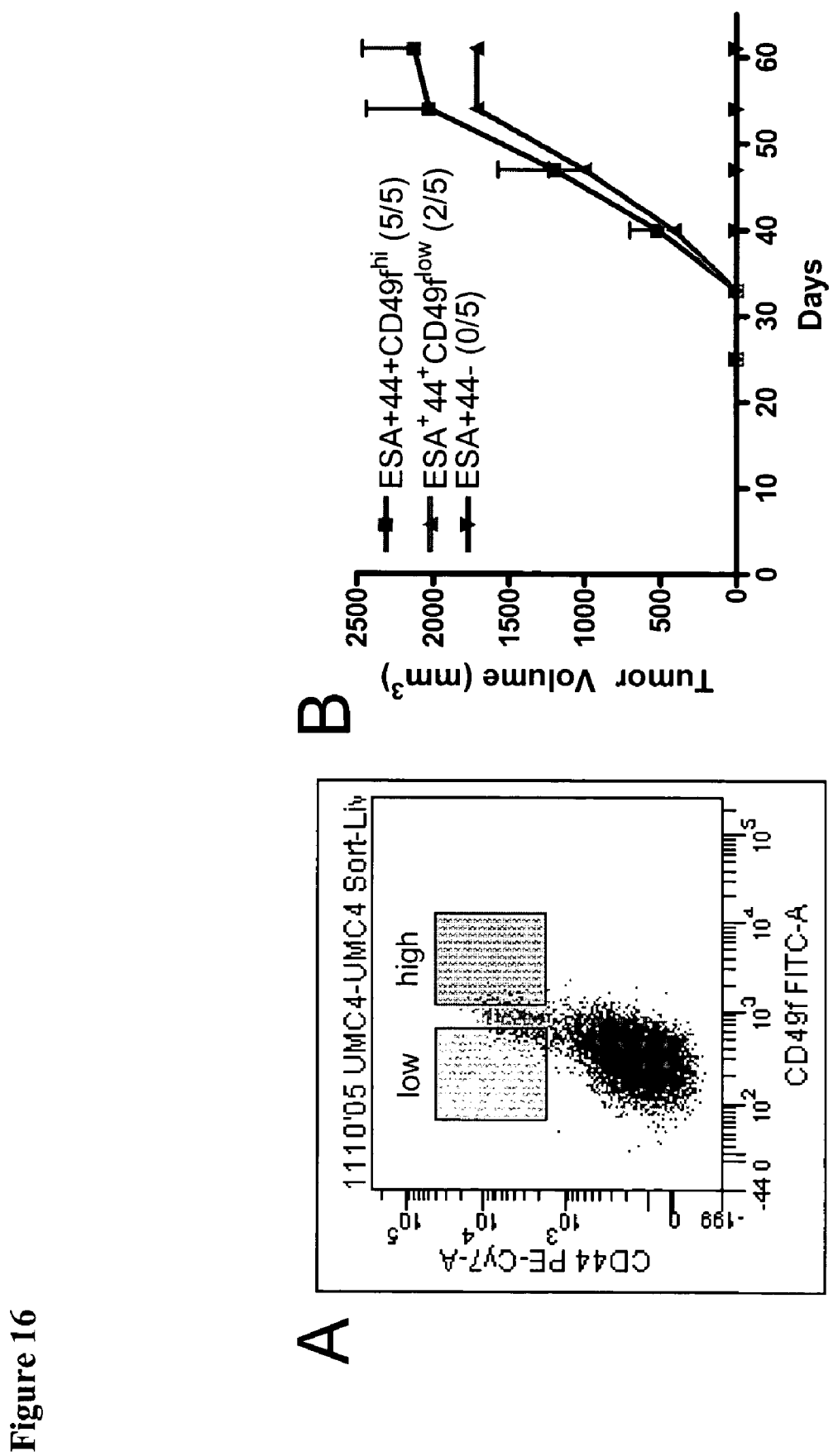

FIG. 16: CD49f (α6-integrin) Enriches for Colon Cancer Stem Cells. A) Mouse lineage-negative (mLin−), ESA+ xenogeneic UM-C4 colon tumor cells have elevated levels of CD49f, and CD49f surface expression was preferentially found on CD44+ cells. B) A tumor growth curves is shown for the denoted FACS purified populations from ESA+CD44+ cells further enriched based on CD49f expression. Means±SEM are plotted and reflect only those mice with palpable tumors. Tumor frequency is shown in parentheses and in Table 4. Data is representative of N=2 separate experiments.

DETAILED DESCRIPTION OF THE INVENTION

The present invention relates to compositions and methods for treating, characterizing and diagnosing cancer. This invention is based on the discovery of solid tumor stem cells (also referred to as cancer stem cells or cancer stem cells from a solid tumor) as a distinct and limited subset of cells within the heterogenous cell population of established solid tumors. These cancer stem cells share the properties of normal stem cells in that they extensively proliferate and efficiently give rise both to additional solid tumor stem cells (self-renewal) and to the majority of tumor cells of a solid tumor that lack tumorigenic potential. Identification of cancer stem cells relies both on 1) their expression of a unique pattern of cell-surface receptors used to isolate them from the bulk of non-tumorigenic tumor cells and 2) their properties of self-renewal and proliferation as assessed in xenograft animal models. This invention relates particularly to the discovery of solid tumor stem cells from colon cancer and head and neck cancer.

In one embodiment, the invention provides a method of selecting cells of a population to obtain a purified population of cancer stem cells (e.g. from a patient biopsy or from human tumor cells passaged via a xenograft in a mouse). The present invention also provides a method of selecting a purified population of tumor cells other than cancer stem cells, such as a population of non-tumorigenic (NTG) tumor cells. Specifically, using cell-surface markers an ESA+CD44+ tumor cell population from a cancer of epithelial origin has been identified that is enriched for the ability to form tumors—is tumorigenic-relative to unfractionated tumor cells and non-ESA+ CD44+ tumor cells (non-tumorigenic cells). The present invention provides research methods of characterizing the properties of cancer stem cells from a tumor of epithelial origin. The present invention provides methods of raising antibodies to the selected cells. The invention provides diagnostic methods using the selected cells. The invention also provides therapeutic methods, where the therapeutic is directed to a cancer stem cell (e.g. directed to one of the cancer stem cell markers identified herein directly or indirectly).

In certain embodiments, the present invention identifies genes that are differentially expressed in tumorigenic ESA+ 44+ colon stem cells compared to presorted colon tumor cells and to non-ESA+44+ sorted colon tumor cells (non-tumorigenic cells) using microarray analysis. A set of genes with increased expression in colon cancer stem cells as compared to non-stem cells is shown in Table 1, and these genes serve as a gene expression profile of colon cancer stem cells and as colon cancer stem cell markers useful for the characterization, diagnosis, and treatment of colon cancer stem cells. The differentially expressed genes, and the peptides encoded thereby, can be detected (e.g. quantitatively) in order to identify the presence and numbers of solid tumor stem cells, and to determine and screen molecules suitable for reducing the proliferation, inducing cell death, interfering with self-renewal pathways, or interfering with survival pathways of any solid tumor stem cells that are present. The differentially expressed genes, and peptides encoded thereby are also useful for generating therapeutic agents targeted to one or more of these markers (e.g. to inhibit or promote the activity of the marker). In certain embodiments of the invention, increased expression of HES1 and HES6 in colon cancer stem cells compared to unfractionated colon tumor cells and non-tumorigenic colon tumor cells is identified in contrast to the Notch target genes HES2, 4 and 7, and a colon cancer stem cell gene marker comprises upregulation of the Notch signaling pathway target genes HES1 and/or HES6.

In certain embodiments the cancer stem cell markers of the present invention can be detected (e.g. in a tumor sample) by expression levels of polynucleotides by, for example, in situ hybridization or RT-PCR. Furthermore, expression levels of polynucleotides such as, for example, mRNA can be quantified using, for example, Taqman analysis. Alternatively the colon cancer stem cell markers of the present invention can be detected in a tumor sample by expression levels of protein by, for example, immunohistochemistry or ELISA. Furthermore, protein expression levels can be quantified using, for example, quantitative immunofluorescence. In some embodiments, mRNA expression of the colon cancer stem cell marker HES6 is detected (e.g. in a tumor sample) by in situ hybridization. In some embodiments, protein expression of the colon cancer stem cell marker HES6 is detected (e.g. in a patient sample) by immunofluorescence using an antibody that specifically recognizes HES6. In other embodiments, HES6 expression is detected in a sample by real-time PCR using primer sets that specifically amplify polynucleotides encoding HES6. In other some embodiments, HES6 expression is quantified to determine the number of cancer stem cells present in a sample (e.g. from a patient).

Accordingly, the invention provides methods of selecting cells, diagnosing disease, conducting research studies, and treating solid tumors using selection methods, diagnostic methods and therapeutics directed to specific genes or a given pathway. Included are one or more of the following genes and gene products: PTGFRN, CD166, CD164, CD82, TGFBR1, MET, EFNB2, ITGA6, TDGF1, HBEGF, ABCC4, ABCD3, TDE2, ITGB1, TNFRSF21, CD81, CD9, KIAA1324, CEACAM6, FZD6, FZD7, BMPR1A, JAG1, ITGAV, NOTCH2, SOX4, HES1, HES6, ATOH1, CDH1, EPHB2, MYB, MYC, SOX9 or STRAP, or lower levels of one or more of TCF4 or VIM, as shown in Table 1 which are differentially expressed in colon cancer stem cells as compared with non-tumorigenic cancer cells, as shown herein.

The invention thus provides a method for selectively targeting diagnostic or therapeutic agents to cancer stem cells. The invention also provides an agent, such as a biomolecule, that is selectively targeted to cancer stem cells (e.g. directed to one of the colon cancer stem cell cancer markers disclosed herein). In some embodiments, the stem cell cancer marker targeted is part of a self-renewal or cell survival pathway. In certain embodiments, the present invention provides methods for screening for anti-cancer agents; for the testing of anti-cancer therapies; for the development of drugs targeting novel pathways; for the identification of new anti-cancer therapeutic targets; the identification and diagnosis of malignant cells in pathology specimens; for the testing and assaying of solid tumor stem cell drug sensitivity; for the measurement of specific factors that predict drug sensitivity; and for the screening of patients (e.g., as an adjunct for mammography).

Other features, objects, and advantages of the invention will be apparent from the detailed description below. Additional guidance is provided in Published PCT patent application WO 02/12447 by the Regents of the University of Michigan and PCT patent application PCT/USO2/39191 by the Regents of the University of Michigan, both of which are incorporated herein by reference.

To facilitate an understanding of the present invention, a number of terms and phrases are defined below:

An "antibody" is an immunoglobulin molecule that recognizes and specifically binds to a target, such as a protein, polypeptide, peptide, carbohydrate, polynucleotide, lipid, etc., through at least one antigen recognition site within the variable region of the immunoglobulin molecule. As used herein, the term is used in the broadest sense and encompasses intact polyclonal antibodies, intact monoclonal antibodies, antibody fragments (such as Fab, Fab', F(ab')$_2$, and Fv fragments), single chain Fv (scFv) mutants, multispecific antibodies such as bispecific antibodies generated from at least two intact antibodies, fusion proteins comprising an antibody portion, and any other modified immunoglobulin molecule comprising an antigen recognition site so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

As used herein, the term "antibody fragments" refers to a portion of an intact antibody. Examples of antibody fragments include, but are not limited to, linear antibodies; single-chain antibody molecules; Fc or Fc' peptides, Fab and Fab fragments, and multispecific antibodies formed from antibody fragments.

As used herein, "humanized" forms of non-human (e.g., murine) antibodies are chimeric antibodies that contain minimal sequence, or no sequence, derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies can comprise residues that are not found in the recipient antibody or in the donor antibody. These modifications are generally made to further refine antibody performance. In general, the humanized antibody will comprise substantially all of at least one, and typically two, variable domains, in which all or substantially all of the hypervariable loops correspond to those of a nonhuman immunoglobulin and all or substantially all of the FR residues are those of a human immunoglobulin sequence. The humanized antibody can also comprise at least a portion of an immunoglobulin constant region (Fc), typically that of a human immunoglobulin. Examples of methods used to generate humanized antibodies are described in U.S. Pat. No. 5,225,539 to Winter et al. (herein incorporated by reference).

The term "human antibody" as used herein means an antibody produced by a human or an antibody having an amino acid sequence corresponding to an antibody produced by a human made using any of the techniques known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

"Hybrid antibodies" are immunoglobulin molecules in which pairs of heavy and light chains from antibodies with different antigenic determinant regions are assembled together so that two different epitopes or two different antigens can be recognized and bound by the resulting tetramer.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g. mouse, rat, rabbit, etc) with the desired specificity, affinity, and capability while the constant regions are homologous to the sequences in antibodies derived from another (usually human) to avoid eliciting an immune response in that species.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation. An antigenic determinant can compete with the intact antigen (i.e., the "immunogen" used to elicit the immune response) for binding to an antibody.

That an antibody "specifically binds" to or shows "specific binding" towards an epitope means that the antibody reacts or associates more frequently, more rapidly, with greater duration, and/or with greater affinity with the epitope than with alternative substances. As used herein, "specifically binds" means that an antibody binds to a protein with a $K_D$ of at least about 0.1 mM, at least about 1 uM, at least about 0.1 uM or better, or 0.01 uM or better.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

As used herein, the term "receptor binding domain" refers to any native ligand for a receptor, including cell adhesion molecules, or any region or derivative of such native ligand retaining at least a qualitative receptor binding ability of a corresponding native ligand.

As used herein, the term "antibody-immunoadhesin chimera" comprises a molecule that combines at least one binding domain of an antibody with at least one immunoadhesin. Examples include, but are not limited to, the bispecific CD4-IgG chimeras described in Berg et al., PNAS (USA) 88:4723-4727 (1991) and Charnow et al., J. Immunol., 153:4268 (1994), both of which are hereby incorporated by reference.

"Enriched", as in an enriched population of cells, can be defined phenotypically based upon the increased number of cells having a particular marker (e.g. as shown in Table 1) in a fractionated set of cells as compared with the number of cells having the marker in the unfractionated set of cells. However, the term "enriched" can be defined functionally by tumorigenic function as the minimum number of cells that form tumors at limit dilution frequency in test mice. For example, if 500 tumor stem cells form tumors in 63% of test animals, but 5000 unfractionated tumor cells are required to form tumors in 63% of test animals, then the solid tumor stem cell population is 10-fold enriched for tumorigenic activity. The stem cell cancer markers of the present invention can be used to generate enriched populations of cancer stem cells. In some embodiments, the stem cell population is enriched at least 1.4 fold relative to unfractionated tumor cells. In other embodiments, the stem cell population is enriched 2 fold to 10 fold relative to unfractionated tumor cells. In further embodiments, the stem cell population is enriched 20 fold relative to unfractionated tumor cells.

"Isolated" in regard to cells, refers to a cell that is removed from its natural environment (such as in a solid tumor) and that is isolated or separated, and is at least about 30%, 50%, 75% free, or about 90% free, from other cells with which it is naturally present, but which lack the marker based on which the cells were isolated. The stem cell cancer markers of the present invention can be used to generate isolated populations of cancer stem cells.

As used herein, the terms "cancer" and "cancerous" refer to or describe the physiological condition in mammals in which a population of cells are characterized by unregulated cell growth. Examples of cancer include, but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer.

"Metastasis" as used herein refers to the process by which a cancer spreads or transfers from the site of origin to other regions of the body with the development of a similar cancerous lesion at the new location. A "metastatic" or "metastasizing" cell is one that loses adhesive contacts with neighboring cells and migrates via the bloodstream or lymph from the primary site of disease to invade neighboring body structures.

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "subject suspected of having cancer" refers to a subject that presents one or more symptoms indicative of a cancer (e.g., a noticeable lump or mass) or is being screened for a cancer (e.g., during a routine physical). A subject suspected of having cancer can also have one or more risk factors. A subject suspected of having cancer has generally not been tested for cancer. However, a "subject suspected of having cancer" encompasses an individual who has received an initial diagnosis but for whom the stage of cancer is not known. The term further includes people who once had cancer (e.g., an individual in remission).

As used herein, the term "subject at risk for cancer" refers to a subject with one or more risk factors for developing a specific cancer. Risk factors include, but are not limited to, gender, age, genetic predisposition, environmental exposure, previous incidents of cancer, preexisting non-cancer diseases, and lifestyle.

As used herein, the term "characterizing cancer in a subject" refers to the identification of one or more properties of a cancer sample in a subject, including but not limited to, the presence of benign, pre-cancerous or cancerous tissue, the stage of the cancer, and the subject's prognosis. Cancers can be characterized by the identification of the expression of one or more cancer marker genes, including but not limited to, the cancer markers disclosed herein.

The terms "cancer stem cell", "tumor stem cell", or "solid tumor stem cell" are used interchangeably herein and refer to a population of cells from a solid tumor that: (1) have extensive proliferative capacity; (2) are capable of asymmetric cell division to generate one or more kinds of differentiated progeny with reduced proliferative or developmental potential; and (3) are capable of symmetric cell divisions for self-renewal or self-maintenance. These properties of "cancer stem cells", "tumor stem cells" or "solid tumor stem cells" confer on those cancer stem cells the ability to form palpable tumors upon serial transplantation into an immunocompromised mouse compared to the majority of tumor cells that fail to generate tumors. Cancer stem cells undergo self-renewal versus differentiation in a chaotic manner to form tumors with abnormal cell types that can change over time as mutations occur. The solid tumor stem cells of the present invention differ from the "cancer stem line" provided by U.S. Pat. No. 6,004,528. In that patent, the "cancer stem line" is defined as a slow growing progenitor cell type that itself has few mutations but which undergoes symmetric rather than asymmetric cell divisions as a result of tumorigenic changes that occur in the cell's environment. This "cancer stem line" hypothesis thus proposes that highly mutated, rapidly proliferating tumor cells arise largely as a result of an abnormal environment, which causes relatively normal stem cells to accumulate and then undergo mutations that cause them to become tumor cells. U.S. Pat. No. 6,004,528 proposes that such a model can be used to enhance the diagnosis of cancer. The solid tumor stem cell model is fundamentally different than the "cancer stem line" model and as a result exhibits utilities not offered by the "cancer stem line" model. First, solid tumor stem cells are not "mutationally spared". The "mutationally spared cancer stem line" described by U.S. Pat. No. 6,004,528 can be considered a pre-cancerous lesion, while the solid tumor stem cells described by this invention are cancer cells that themselves contain the mutations that are responsible for tumorigenesis. That is, the solid tumor stem cells ("cancer stem cells") of the invention would be included among the highly mutated cells that are distinguished from the "cancer stem line" in U.S. Pat. No. 6,004,528. Second, the genetic mutations that lead to cancer can be largely intrinsic within the solid tumor stem cells as well as being environmental. The solid tumor stem cell model predicts that isolated solid tumor stem cells can give rise to additional tumors upon transplantation (thus explaining metastasis) while the "cancer stem line" model would predict that transplanted "cancer stem line" cells would not be able to give rise to a new tumor, since it was their abnormal environment that was tumorigenic. Indeed, the ability to transplant dissociated, and phenotypically isolated human solid tumor stem cells to mice (into an environment that is very different from the normal tumor environment), where they still form new tumors, distinguishes the present invention from the "cancer stem line" model. Third, solid tumor stem cells likely divide both symmetrically and asymmetrically, such that symmetric cell division is not an obligate property. Fourth, solid tumor stem cells can divide rapidly or slowly, depending on many variables, such that a slow proliferation rate is not a defining characteristic.

As used herein "tumorigenic" refers to the functional features of a solid tumor stem cell including the properties of self-renewal (giving rise to additional tumorigenic cancer stem cells) and proliferation to generate all other tumor cells (giving rise to differentiated and thus non-tumorigenic tumor cells) that allow solid tumor stem cells to form a tumor. These properties of self-renewal and proliferation to generate all other tumor cells confer on the cancer stem cells of this invention the ability to form palpable tumors upon serial transplantation into an immunocompromised mouse compared to the majority of tumor cells that are unable to form tumors upon the serial transplantation. Tumor cells, i.e. non-tumorigenic tumor cells, may form a tumor upon transplantation into an immunocompromised mouse a limited number of times (for example one or two times) after obtaining the tumor cells from a solid tumor.

As used herein, the terms "stem cell cancer marker(s)", "cancer stem cell marker(s)", "tumor stem cell marker(s)", or "solid tumor stem cell marker(s)" refer to a gene or genes or a protein, polypeptide, or peptide expressed by the gene or genes whose expression level, alone or in combination with other genes, is correlated with the presence of tumorigenic cancer cells compared to non-tumorigenic cells. The correlation can relate to either an increased or decreased expression of the gene (e.g. increased or decreased levels of mRNA or the peptide encoded by the gene).

As used herein, the terms "unfractionated tumor cells", "presorted tumor cells", "bulk tumor cells", and their grammatical equivalents are used interchangeably to refer to a tumor cell population isolated from a patient sample (e.g. a tumor biopsy or pleural effusion) that has not been segregated, or fractionated, based on cell surface marker expression.

As used herein, the terms "non-ESA+CD44+ tumor cells", "non-ESA+44+", "sorted non-tumorigenic tumor cells", "non-tumorigenic tumor cells," "non-stem cells," "tumor cells" and their grammatical equivalents are used interchangeably to refer to a tumor population from which the cancer stem cells of this invention have been segregated, or removed, based on cell surface marker expression.

"Gene expression profile" refers to identified expression levels of at least one polynucleotide or protein expressed in a biological sample.

A "gene profile," "gene pattern," "expression pattern" or "expression profile" refers to a specific pattern of gene expression that provides a unique identifier of a biological sample, for example, a breast or colon cancer pattern of gene expression, obtained by analyzing a breast or colon cancer sample and in those cases can be referred to as a "breast cancer gene profile" or a "colon cancer expression pattern". "Gene patterns" can be used to diagnose a disease, make a prognosis, select a therapy, and/or monitor a disease or therapy after comparing the gene pattern to a cancer stem cell gene signature.

As used herein, the term "gene expression" refers to the process of converting genetic information encoded in a gene into RNA (e.g., mRNA, rRNA, tRNA, or snRNA) through "transcription" of the gene (e.g., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (e.g., RNA or protein), while "down-regulation" or "repression" refers to regulation that decrease production. Molecules (e.g., transcription factors) that are involved in up-regulation or down-regulation are often called "activators" and "repressors," respectively.

The terms "high levels", "increased levels", "high expression", "increased expression", "elevated levels" or "upregulated expression" in regards to gene expression are used herein interchangeably to refer to expression of a gene in a cell or population of cells, particularly a cancer stem cell or population of cancer stem cells, at levels higher than the expression of that gene in a second cell or population of cells, for example, unfractionated colon tumor cells or non-ESA+ 44+ colon tumor cells. "Elevated levels" of gene expression refers to expression of a gene in a cancer stem cell or population of cancer stem cells at levels twice that or more of expression levels of the same gene in unfractionated colon tumor cells or non-ESA+44+ colon tumor cells. "Elevated levels" of gene expression also refers to expression of a gene in a cancer stem cell or population of cancer stem cells at levels six times that or more of expression levels of the same gene in unfractionated colon tumor cells or non-ESA+44+ colon tumor cells. "Elevated levels" of gene expression can be determined by detecting increased amounts of a polynucleotide (mRNA, cDNA, etc.) in cancer stem cells compared to unfractionated colon tumor cells or non-ESA+44+ colon tumor cells by, for example, quantitative RT-PCR or microarray analysis. Alternatively "elevated levels" of gene expression can be determined by detecting increased amounts of a protein in cancer stem cells compared to unfractionated colon tumor cells or non-ESA+44+ colon tumor cells by, for example, ELISA, Western blot, quantitative immunfluorescence.

The term "undetectable levels" or "loss of expression" in regards to gene expression as used herein refers to expression of a gene in a cell or population of cells, particularly a cancer stem cell or population of cancer stem cells, at levels that cannot be distinguished from background using conventional techniques such that no expression is identified. "Undetectable levels" of gene expression can be determined by the inability to detect levels of a polynucleotide (mRNA, cDNA, etc.) in cancer stem cells above background by, for example, quantitative RT-PCR or microarray analysis. Alternatively "undetectable levels" of gene expression can be determined by the inability to detect levels of a protein in cancer stem cells above background by, for example, ELISA, Western blot, or immunofluorescence.

As used herein, the terms "low levels", "decreased levels", "low expression", "reduced expression" or "decreased expression" in regards to gene expression are used herein interchangeably to refer to expression of a gene in a cell or population of cells, particularly a cancer stem cell or population of cancer stem cells, at levels less than the expression of that gene in a second cell or population of cells, for example unfractionated colon tumor cells or non-ESA+44+ colon tumor cells. "Low levels" of gene expression refers to expression of a gene in a cancer stem cell or population of cancer stem cells at levels: 1) half that or below expression levels of the same gene in unfractionated colon tumor cells or non-ESA+44+ colon tumor cells and 2) at the lower limit of detection using conventional techniques. "Low levels" of gene expression can be determined by detecting decreased to nearly undetectable amounts of a polynucleotide (mRNA, cDNA, etc.) in cancer stem cells compared to unfractionated colon tumor cells or non-ESA+44+ colon tumor cells by, for example, quantitative RT-PCR or microarray analysis. Alternatively "low levels" of gene expression can be determined by detecting decreased to nearly undetectable amounts of a protein in cancer stem cells compared to unfractionated colon tumor cells or non-ESA+44+ colon tumor cells by, for example, ELISA, Western blot, or quantitative immunfluorescence.

As used herein, the term "a reagent that specifically detects expression levels" refers to reagents used to detect the expression of one or more genes (e.g., including but not limited to, the cancer markers of the present invention). Examples of suitable reagents include but are not limited to, nucleic acid probes capable of specifically hybridizing to the gene of interest, aptamers, PCR primers capable of specifically amplifying the gene of interest, and antibodies capable of specifically binding to proteins expressed by the gene of interest. Other non-limiting examples can be found in the description and examples below.

As used herein, the term "detecting a decreased or increased expression relative to non-cancerous control" refers to measuring the level of expression of a gene (e.g., the level of mRNA or protein) relative to the level in a non-cancerous control sample. Gene expression can be measured using any suitable method, including but not limited to, those described herein.

As used herein, the term "detecting a change in gene expression in a cell sample in the presence of said test compound relative to the absence of said test compound" refers to measuring an altered level of expression (e.g., increased or decreased) in the presence of a test compound relative to the absence of the test compound. Gene expression can be measured using any suitable method.

As used herein, the term "instructions for using said kit for detecting cancer in said subject" includes instructions for using the reagents contained in the kit for the detection and characterization of cancer in a sample from a subject.

As used herein, "providing a diagnosis" or "diagnostic information" refers to any information that is useful in determining whether a patient has a disease or condition and/or in classifying the disease or condition into a phenotypic category or any category having significance with regards to the prognosis of or likely response to treatment (either treatment in general or any particular treatment) of the disease or condition. Similarly, diagnosis refers to providing any type of diagnostic information, including, but not limited to, whether a subject is likely to have a condition (such as a tumor), information related to the nature or classification of a tumor as for example a high risk tumor or a low risk tumor, information related to prognosis and/or information useful in selecting an appropriate treatment. Selection of treatment can include the choice of a particular chemotherapeutic agent or other treatment modality such as surgery or radiation or a choice about whether to withhold or deliver therapy.

As used herein, the terms "providing a prognosis", "prognostic information", or "predictive information" refer to providing information regarding the impact of the presence of cancer (e.g., as determined by the diagnostic methods of the present invention) on a subject's future health (e.g., expected morbidity or mortality, the likelihood of getting cancer, and the risk of metastasis).

As used herein, the term "post surgical tumor tissue" refers to cancerous tissue (e.g., biopsy tissue) that has been removed from a subject (e.g., during surgery).

As used herein, the term "subject diagnosed with a cancer" refers to a subject who has been tested and found to have cancerous cells. The cancer can be diagnosed using any suitable method, including but not limited to, biopsy, x-ray, blood test, and the diagnostic methods of the present invention.

As used herein, the terms "biopsy tissue", "patient sample", "tumor sample", and "cancer sample" refer to a sample of cells, tissue or fluid that is removed from a subject for the purpose of determining if the sample contains cancerous tissue, including cancer stem cells or for determining gene expression profile of that cancerous tissue. In some embodiment, biopsy tissue or fluid is obtained because a subject is suspected of having cancer. The biopsy tissue or fluid is then examined for the presence or absence of cancer, cancer stem cells, and/or cancer stem cell gene signature expression.

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of the sample to a desired cell or tissue. As used herein, the term "adenovirus gene transfer system" refers to gene transfer systems comprising intact or altered viruses belonging to the family Adenoviridae.

As used herein, the term "site-specific recombination target sequences" refers to nucleic acid sequences that provide recognition sequences for recombination factors and the location where recombination takes place.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns can contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "gene expression" refers to the process of converting genetic information encoded in a gene into RNA (e.g., mRNA, rRNA, tRNA, or snRNA) through "transcription" of the gene (e.g., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (e.g., RNA or protein), while "down-regulation" or "repression" refers to regulation that decrease production. Molecules (e.g., transcription factors) that are involved in up-regulation or down-regulation are often called "activators" and "repressors," respectively.

In addition to containing introns, genomic forms of a gene can also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region can contain regulatory sequences such as promoters and enhancers that control or influence the transcription of the gene. The 3' flanking region can contain sequences that direct the termination of transcription, post-transcriptional cleavage and polyadenylation.

The term "siRNAs" refers to short interfering RNAs. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to or substantially complementary to a target RNA molecule. The strand complementary to a target RNA molecule is the "antisense strand;" the strand homologous to the target RNA molecule is the "sense strand," and is also complementary to the siRNA antisense strand. siRNAs can also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene can be endogenous or exogenous to the organism, present integrated into a chromosome or present in a transfection vector that is not integrated into the genome. The expression of the gene is either completely or partially inhibited. RNAi can also be considered to inhibit the function of a target RNA; the function of the target RNA can be complete or partial.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence that encodes a gene product. The coding region can be present in a cDNA, genomic DNA or RNA form. When present in a DNA form, the oligonucleotide or polynucleotide can be single-stranded (i.e., the sense strand) or double-stranded. Suitable control elements such as enhancers/promoters, splice junctions, polyadenylation signals, etc. can be placed in close proximity to the coding region of the gene if needed to permit proper initiation of transcription and/or correct processing of the primary RNA transcript. Alternatively, the coding region utilized in the expression vectors of the present invention can contain endogenous enhancers/promoters, splice junctions, intervening sequences, polyadenylation signals, etc. or a combination of both endogenous and exogenous control elements.

As used herein the term "portion" when in reference to a nucleotide sequence (as in "a portion of a given nucleotide sequence") refers to fragments of that sequence. The fragments can range in size from four nucleotides to the entire nucleotide sequence minus one nucleotide (10 nucleotides, 20, 30, 40, 50, 100, 200, etc.).

The phrases "hybridizes", "selectively hybridizes", or "specifically hybridizes" refer to the binding or duplexing of a molecule only to a particular nucleotide sequence under stringent hybridization conditions when that sequence is present in a complex mixture (e.g., a library of DNAs or RNAs). See, e.g., Andersen (1998) Nucleic Acid Hybridization Springer-Verlag; Ross (ed. 1997) Nucleic Acid Hybridization Wiley.

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point (Tm) for the specific sequence at a defined ionic strength. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions can also be achieved with the addition of destabilizing agents such as formamide. For high stringency hybridization, a positive signal is at least two times background, or 10 times background hybridization. Exemplary high stringency or stringent hybridization conditions include: 50% formamide, 5×SSC, and 1% SDS incubated at 42° C. or 5×SSC and 1% SDS incubated at 65° C., with a wash in 0.2×SSC and 0.1% SDS at 65° C. For PCR, a temperature of about 36° C. is typical for low stringency amplification, although annealing temperatures can vary from about 32° C. to about 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C. to 95° C. for 30-120 sec, an annealing phase lasting 30-120 sec, and an extension phase of about 72° C. for 1-2 min.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide can be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide can be single-stranded), but can contain both the sense and anti-sense strands (i.e., the oligonucleotide or polynucleotide can be double-stranded).

"Amino acid sequence" and terms such as "polypeptide", "protein", or "peptide" are not meant to limit the amino acid sequence to the complete, native amino acid sequence associated with the recited protein molecule.

The term "native protein" as used herein to indicate that a protein does not contain amino acid residues encoded by vector sequences; that is, the native protein contains only those amino acids found in the protein as it occurs in nature. A native protein can be produced by recombinantly or can be isolated from a naturally occurring source.

As used herein the term "portion" when in reference to a protein (as in "a portion of a given protein") refers to fragments of that protein. The fragments can range in size from four amino acid residues to the entire amino acid sequence minus one amino acid.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA can be cleaved with restriction enzymes prior to electrophoresis. Following electrophoresis, the DNA can be partially depurinated and denatured prior to or during transfer to the solid support. Southern blots are a standard tool of molecular biologists (J. Sambrook et al., Molecular Cloning: A Laboratory Manual, Cold Spring Harbor Press, NY, pp 9.31-9.58 [1989]).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al., supra, pp 7.39-7.52 [1989]).

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies can be detected by various methods, including the use of radiolabeled antibodies.

The term "transgene" as used herein refers to a foreign gene that is placed into an organism by, for example, introducing the foreign gene into newly fertilized eggs or early embryos. The term "foreign gene" refers to any nucleic acid (e.g., gene sequence) that is introduced into the genome of an animal by experimental manipulations and can include gene sequences found in that animal so long as the introduced gene does not reside in the same location as does the naturally occurring gene.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of bodily function (e.g., cancer). Test compounds comprise both known and potential therapeutic compounds. A test compound can be determined to be therapeutic by screening using the screening methods of the present invention. In some embodiments of the present invention, test compounds include antisense compounds.

As used herein, the term "sample" is used in its broadest sense. In one sense, it is meant to include a specimen or culture obtained from any source, as well as biological and environmental samples. Biological samples can be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

By "specific binding" or "unique binding" is intended when an agent binds only to a particular ligand, receptor, or antigen. By "selective binding" is intended when an agent preferably binds to a ligand, receptor, or antigen over others by a magnitude of about two-fold or great, about five-fold or greater, about eight-fold or greater, or about ten-fold or greater.

As used herein, "about" refers to plus or minus 10% of the indicated number. For example, "about 10%" indicates a range of 9% to 11%.

The present invention provides compositions and methods for treating, characterizing, and diagnosing cancer. In particular, the present invention provides gene expression profiles associated with solid tumor stem cells, as well as novel markers useful for the diagnosis, characterization, and treatment of solid tumor stem cells.

Solid Tumor Stem Cells Cancer Markers

The present invention provides markers whose expression is differentially expressed in colon cancer stem cells compared to unfractionated colon tumor cells or non-ESA+44+ colon tumor cells. Such markers find use in the diagnosis and characterization and alteration (e.g., therapeutic targeting) of various cancers (e.g. colon cancer).

Example 1, provided below, describes methods used to identify solid tumor cancer markers. Preferred cancer markers are provided below in Table 1. While these tables provide gene names, it is noted that the present invention contemplates the use of both the nucleic acid sequences as well as the peptides encoded thereby, as well as fragments of the nucleic acid and peptides, in the therapeutic and diagnostic methods and compositions of the present invention.

TABLE 1

Solid Tumor Cancer Markers Up, or Down, Regulated in Tumorigenic Colon Cancer Stem Cells versus Non-Tumorigenic Cancer Cells

| UPREGULATED | | | |
|---|---|---|---|
| PTGFRN | CD166 | CD164 | CD82 |
| TGFBR1 | MET | EFNB2 | ITGA6 (CD49f) |
| TDGF1 | HBEGF | ABCC4 | ABCD3 |
| TDE2 | ITGB1 | TNFRSF21 | CD81 |
| CD9 | KIAA1324 | HES6 | SOX4 |
| FZD6 | FZD7 | BMPR1A | JAG1 |
| ITGAV | NOTCH2 | ATOH1 | CDH1 |
| EPHB2 | MYB | MYC | SOX9 |
| STRAP | HES1 | CD59 | PCGF1, |
| ALDH1A1 | | | 4(BMI1), 5 |
| DOWNREGULATED | | | |
| TCF4 | VIM | | |

In certain embodiments of the present invention, colon cancer stem cell expression comprises elevated levels of prostaglandin F2 receptor regulatory protein (PTGFRN or FPRP), CD81 and CD9 compared to non-tumorigenic colon tumor cells. PTGFRN is a member of the cell-surface Ig superfamily and associates robustly and specifically with CD81 and CD9, two members of the transmembrane-4 superfamily (TM4SF or tetraspanins) in cancer cell lines (Stipp et al., 2001, J. Biol. Chem. 276:4853-62; Charrin et al., 2001, J. Biol. Chem. 276:14329-37). PTGFRN contains six extracellular immunoglobulin domains and associates with seven transmembrane receptors including the prostaglandin $F_{2\alpha}$ receptor to reduce receptor ligand binding capacity (Orlicky, 1996, Prostaglandins Leukotrienes Essent. Fatty Acids 54:247-59: Orlicky et al., 1998, J. Lipid Res. 39:1152-61). Tetraspanins have been implicated in many cellular functions including adhesion, migration, signal transduction, and differentiation. CD81 knockout mice demonstrate a role for CD81 in B cell signaling and activation as well as T-cell proliferation (Maecker & Levy, 1997, J. Exp. Med. 185:1505-10; Tsitsikov et al., 1997, PNAS 94:10844-49; Miyazaki et al., 1997, EMBO J. 16:4217-25) whereas CD9 knockout mice show reduced fertilization due to impaired fusion of sperm and egg (Miyado et al., 2000, Science 287:321-4; Le Naour et al., 2000, Science 287:319-21). Furthermore, CD9 can act as a suppressor of metastasis as its expression in tumors in inversely correlated with metastases and it can reduce the metastatic potential of melanoma cells (Ikeyama et al., 1993, J. Exp. Med. 177:1231-

37; Si & Hersey, 1993, Int. J. Cancer 54:37-43; Miyake et al., 1995, Cancer Res. 55:4127-31; Adachi et al., 1998, J. Clin. Oncol. 16:1397-1406; Mori et al., 1998, Clin. Cancer Res. 4:1507-10). Yet, both CD81 and CD9 lack obvious intracellular signaling domains and can act as adaptors to connect a subset of cell-surface proteins into a network, or tetraspanin web (Maecker et al., 1997, 1997, FASEB J. 11:428-442; Rubinstein et al., 1996, Eur. J. Immunol. 26:2657-65). That PTGFRN, CD81 and CD9 have been identified as a discrete biochemical entity and that all are upregulated in colon cancer stem cells suggests that this complex can play a role in stem cell biology and serve as a useful target for cancer therapies.

In certain embodiments of the present invention, colon cancer stem cell expression comprises elevated levels of CD166 (or activated leukocyte adhesion molecule; ALCAM) compared to non-tumorigenic colon tumor cells. CD166 is a member of the immunoglobulin superfamily with five extracellular immunoglobulin-like domains and promotes both heterophilic and homophilic cell-cell interactions. CD166 shows broad expression in epithelia, neurons, lymphoid and myeloid cells, hematopoietic and mesenchymal stem cells and functions in the development and maintenance of tissue architecture, neurogenesis, hematopoiesis, immune responses and tumor progression (Swart, 2002, Eur. J. Cell Biol. 81:313-21). CD166 expression generally occurs in proliferating cells including a number of carcinoma cells and cell lines, and in the invasive cells of melanocytic skin lesions where its expression correlates with tumor progression (Degen et al., 1998, Am. J. Pathol. 152:805-13; van Kempen et al., 2000, Am. J. Pathol. 156:769-74; Kristiansen et al., 2003, Prostate 54:34-43). Furthermore, overexpression of truncated CD166, which cannot mediate homophilic cell interactions, promotes tissue invasion (van Kempen et al., 2001, J. Biol. Chem. 276:25783-90) suggesting CD166 plays a role in the transition between cell clustering and cell movement.

In certain embodiments of the present invention, colon cancer stem cell expression comprises elevated levels of CD164 compared to non-tumorigenic colon tumor cells. CD164 is a member of a family of glycoprotein sialomucin receptors and is highly expressed by primitive hematopoietic progenitor cells where it is involved in adhesion of progenitor cells to the stroma and can act as a negative regulator of progenitor cell proliferation (Watt & Chan, 2000, Leuk. Lymphoma 37:1-25).

In certain embodiments of the present invention, colon cancer stem cell expression comprises elevated levels of CD82 compared to non-tumorigenic colon tumor cells. CD82 is a ubiquitously member of the tetraspanin superfamily that has been implicated in many cellular functions including adhesion, migration, signal transduction, and differentiation (Maeker et al., 1997, FASEB J. 11:428-42). Like CD9 described in detail above, CD82 acts as a suppressor of metastasis, with expression lower in metastatic cells compared with a number of primary tumor (Liu et al., 2003, World J. Gastroenterol. 9:1231-6).

In certain embodiments of the present invention, colon cancer stem cell expression comprises elevated levels of transforming growth factor, beta receptor I (TGFBR1) compared to non-tumorigenic colon tumor cells. The TGF-β pathway regulates numerous processes including: cellular proliferation, adhesion and differentiation; hematopoiesis; inflammation; skeletal development and tissue homeostasis (Waite & Eng, 2003, Nat. Rev. Genet. 4:763; Chen et al., 2004, Growth Factors 22:233-41; He et al., 2005, Ann. N.Y. Acad. Sci. 1049:28-38). Deregulated TGF-β signaling is implicated in a range of human diseases including several cancers suggesting that carcinogenesis can proceed by usurping homeostatic mechanisms controlling normal development (Beachy et al., 2004, Nature 432:324).

TGFBR1 is the type 1 receptor for TGF-β isoforms. These secreted cytokines activate heteromeric complexes of type I and type II serine/threonine kinase receptors. The type II receptor kinase is constitutively active and upon ligand binding phosphorylates the type I receptor, activating a downstream signal through cytosolic SMAD proteins. TGF-β isoforms act through receptor-regulated SMAD 2 and 3 which in turn interact with a common partner SMAD, SMAD4, to regulate transcription (Waite & Eng, 2003, Nat. Rev. Genet. 4:763).

The anti-mitogenic response of cells to TGF-β ligands suggests that pathway components are tumor suppressors with inactivation of the pathway contributing to tumorigenesis (Itoh et al., 2000, Eur. J. Biochem. 267:6954). This has been confirmed in knock-out mice with Smad3-deficient mice developing metastatic colorectal cancer, Smad4 heterozygous mice developing malignant intestinal tumors, and conditional Bmpr1 loss in the epidermis and hair follicles results in hair matrix cell hyperplasia (Zhu et al., 1998, Cell 94:703-14; Takaku et al., 1998, Cell 92:645-56; Ming Kwan et al., 2004, Genesis 39:10-25). In humans, Smad4 is mutated or inactivated in a number of cancers including pancreatic, colon, breast and lung cancers (Hahn et al., 1996, Science 271:350-3; Schutte et al., 1996, Cancer Res. 56:2527-30). Furthermore, germline mutations in the mothers against decapentaplegic homologue 4 gene (MADH4), which encodes SMAD4, and the BMP receptor type IA gene (BMPR1A) are associated with 15-20% and 20-25%, respectively, of juvenile polyposis syndrome (JPS) cases, an autosomal dominant cancer syndrome characterized by gastrointestinal hamartomatous polyps and a high risk of gastrointestinal cancer (Howe et al., 1998, Science 280:1086-8; Howe et al., 2001, Nat. Genet. 28:184-7; Zhou et al., 2001, Am. J. Hum. Genet. 69:704-11). The identification of TGFBR1 as upregulated in colon cancer stem cells suggests that targeting the TGF-β pathway can help eliminate tumorigenic cells responsible for the formation and reoccurrence of solid tumors.

In certain embodiments of the present invention, colon cancer stem cell expression comprises elevated levels of MET, a receptor tyrosine kinase activated by the secreted hepatocyte growth factor/scatter factor (HGF/SF), compared to non-tumorigenic colon tumor cells. MET controls cell proliferation, dissociation, and migration during embryogenesis and aberrant activation of these processes in human cancer contributes to tumor growth and metastasis. MET activation phosphorylates beta-catenin, a modification that promotes loss of beta-catenin association with alpha-catenin at cell junctions and thus decreasing cellular adhesion and making beta-catenin available for Wnt mediated signaling, itself associated with carcinogenesis (Tokunou et al., 2001, Am. J. Pathol. 158:1451; Birchmeier et al., 2003, Nat. Rev. Mol. Cell. Biol. 4:915; Biez, 2004, Curr. Biol. 15:R64; Boccaccio et al., 2005, Nature 434:396; and Ma et al., 2005, Cancer Res. 65:1479).

In certain embodiments of the present invention, colon cancer stem cell expression comprises elevated levels of ephrin-B2 (EFNB2) compared to non-tumorigenic colon tumor cells. EFNB2 is a member of a family of membrane-bound ligands that interact with receptor tyrosine kinases, the Eph receptors to generate a bi-directional cell-cell contact signaling system that directs cell migration, neural cell guidance and vasculogenesis. EFNB2 is a transmembrane ligand that binds to the EPHB4 and EPHA3 receptors. Both Eph receptors and ephrin ligands are overexpressed in a number of cancers, including breast, small-cell lung, and gastrointestinal cancer, melanomas, and neuroblastomas (Nakamoto & Bergemann, 2002, Microsc. Res. Tech. 59:58-67).

In certain embodiments of the present invention, colon cancer stem cell expression comprises elevated levels of integrin alpha 6 (ITGA6; CD49f), integrin alpha V (ITGAV) and integrin beta 1 (ITGB1) compared to non-tumorigenic colon tumor cells. Integrins are integral cell-surface proteins that consist of both an alpha and a beta chain with chains associating with multiple partners to form different integrins. Integrins function in cellular adhesion and migration to reversibly connect cells to the extracellular matrix or to receptors on other cells and thus can play a critical role in cancer invasion and metastasis. Integrin-mediated adhesion also affects intracellular signaling and can thus regulate cell survival, proliferation, and differentiation (Danen, 2005, Curr. Pharm. Des. 11:881-91).

In certain embodiments of the present invention, colon cancer stem cell expression comprises elevated levels of teratocarcinoma-derived growth factor 1 (TDGF1) or CRIPTO compared to non-tumorigenic colon tumor cells. TDGF1 is a GPI-linked protein with a single EGF-like motif and a novel cysteine-rich domain called the Cripto, FRL-1, and Cryptic (CFC) motif and acts as a coreceptor to recruit the TGF-β ligand, Nodal, to the activin receptor (Yeo & Whitman, 2001, Mol. Cell. 7:949-57; Yan et al., 2002, Mol. Cell. Biol. 22:4439-49). TDGF1 and is highly overexpressed in a number of cancers including breast, pancreatic, ovarian and colon carcinomas (Salomon et al., 2000, Endocr. Relat. Cancer 7:199-226) and acts to block Activin B-mediated suppression of cell proliferation suggesting an important role in carcinogenesis (Shen, 2003, J. Clin. Invest. 112:500-2).

In certain embodiments of the present invention, colon cancer stem cell expression comprises elevated levels of heparin-binding EGF-like growth factor (HBEGF) compared to non-tumorigenic colon tumor cells. HBEGF is synthesized as a membrane bound precursor protein and, similar to other EGFR ligands, becomes active through release from the cell membrane by ectodomain shedding (Massague et al., 1993, Annu Rev Biochem, 62:515-41). HBEGF is a potent inducer of tumor growth and angiogenesis, and dysregulation of ectodomain shedding produces lethal hyperplasia in mice (Ongusaha et al., 2004, Cancer Res. 64:5283-90; Yamazaki et al., 2003, J. Cell Biol. 163:469-75).

In certain embodiments of the present invention, colon cancer stem cell expression comprises elevated levels of ABCC3 and ABCC4 compared to non-tumorigenic colon tumor cells. ABCC3 and ABCC4 are members of the ATP-binding cassette transporter superfamily and the MRP subfamily involved in multi-drug resistance by reducing the concentration of intracellular drugs. The increased expression of these transporters in colon cancer stem cells suggests a mechanism by which these cells evade chemotherapies leading to cancer reoccurrence and can serve as useful targets to render cancer stem cells vulnerable to such drugs.

In certain embodiments of the present invention, colon cancer stem cell expression comprises elevated levels of TDE2 compared to non-tumorigenic colon tumor cells. TDE2 has sequence similarity to the mouse testicular tumor-differentially-expressed (Tde1) gene and was identified as a gene upregulated in non-small cell lung cancers (Player et al., 2003, Int. J. Cancer 107:238-43).

In certain embodiments of the present invention, colon cancer stem cell expression comprises elevated levels of TNFRSF21 compared to non-tumorigenic colon tumor cells. TNFRSF21 is a member of the tumor necrosis factor receptor superfamily, which is critically involved in the regulation of inflammation, immune response, and lymphoid tissue homeostatsis (Smith et al., 1994, Cell 76:959-62; Locksley et al., 2001, Cell 104:487-501). TNFRSF21 can activate NFkappaB and MAPK8/JNK and induce cell apoptosis. Furthermore, knockout studies demonstrate TNFRSF21 acts as an important regulator of CD4+ T cell proliferation, Th differentiation, B cell activation and humoral immune responses (Liu et al., 2001, Immunity 15:23-34; Zhao et al., 2001, J. Exp. Med. 194:1441-8; Schmidt et al., 2003, J. Exp. Med. 197:51-62).

In certain embodiments of the present invention, colon cancer stem cell expression comprises elevated levels KIAA1324 compared to non-tumorigenic colon tumor cells. KIAA1324 is a putative cell-surface protein.

In certain embodiments of the present invention, colon cancer stem cell expression comprises elevated levels of SOX4 or SRY (sex determining region Y)-box 4 compared to non-tumorigenic colon tumor cells. SOX (SRY-related HMG box) family member gene products are critical to embryonic developmental and cell fate determination during organogenesis. The best defined system for the role of SOX4 in organogenesis is in brain development (Wegner & Stolt, 2005, Trends Neurosci, 28:583-8). Elevated SOX4 expression has also been correlated with increased survival of tumor cells in a number of tumor types, including, but not limited to, bladder and prostate cancer (Aaboe et al., 2006, Cancer Res, 66:3434-42; Liu et al., 2006, Cancer Res, 66:4011-9; Pramoonjago et al., 2006, Oncogene, 25:5626-39).

In certain embodiments of the present invention, colon cancer stem cell expression comprises elevated levels of atonal homolog 1 (ATOH1) compared to non-tumorigenic colon tumor cells. ATOH1 is a basic helix-loop-helix (BHLH) family transcription factor thought to be a target of the Wnt signaling pathway (Loew et al., 2005, Ann N Y Acad Sci, 1059:174-83). Its tight regulation of ATOH1 expression is important for normal colonic development (Loew et al., 2005, Ann N Y Acad Sci, 1059:174-83; Mutoh et al., 2006, Differentiation, 74:313-21).

In certain embodiments of the present invention, colon cancer stem cell expression comprises elevated levels of E-cadherin (CDH1) compared to non-tumorigenic colon tumor cells. CDH1 encodes a classical, calcium-dependent glycoprotein cadherin involved in cell-cell adhesion (Cavallaro & Christofori, 2004, Nat Rev Cancer, 4:118-32). Altered CDH1 expression, or mutations, result in tumorigenesis in a number of organs, and tumor aggressiveness has been correlated with loss of functional CDH1 (Georgolios et al., 2006, J Exp Clin Cancer Res, 25:5-14; Katoh, 2005, Int J Oncol, 27:1677-83; Cowin et al., 2005, Curr Opin Cell Biol, 17:499-508; Charalabopoulos et al., 2004, Exp Oncol, 26:256-60).

In certain embodiments of the present invention, colon cancer stem cell expression comprises elevated levels of Eph receptor B2 (EPHB2) compared to non-tumorigenic colon tumor cells. Ephrin receptors respond to their ligands, the ephrins, to regulate a number of tissue developmental processes, including gut organization, bone formation, and CNS regeneration (Crosnier et al., 2006, Nat Rev Genet, 7:349-59; Mundy & Elefteriou., 2006, Cell, 126:441-3; Klein, 2004, Curr Opin Cell Biol, 16:580). Of interest, altered EphB2 expression or function has been correlated with aggressiveness in neoplasias of the gut and prostate (Kokko et al., 2006, BMC Cancer, 6:145; Batlle et al., 2005, Nature, 435:1126-30; Huusko et al., 2004, Nat Genet, 36:979-83; Kataoka et al., 2002, J Cancer Clin Oncol, 128:343-8).

In certain embodiments of the present invention, colon cancer stem cell expression comprises elevated levels of v-myb myeloblastosis viral oncogene homolog (MYB) compared to non-tumorigenic colon tumor cells. MYB has been identified as an oncogene in pancreatic cancer and also plays a significant role in cell fate decisions during hematopoeitic development (Maitra et al., 2006, Best Pract Res Clin Gastroenterol, 20:211-26; Sakamoto et al., 2006, Blood, 108: 896-903; Ramsay, 2005, Growth Factors, 23:253-61). Overexpression of MYB may facilitate tumorigenesis by increasing the expression of genes that promote survival in low oxygen and nutrient conditions (Ramsay et al., 2005, Int J Biochem Cell Biol, 37:1254-68; Xu et al., 2003, Am J Physiol Cell Physiol, 284:c1262-71).

In certain embodiments of the present invention, colon cancer stem cell expression comprises elevated levels of (MYC) compared to non-tumorigenic colon tumor cells. Myc is a strong oncogene that promotes cell cycle progression and transformation, and its overexpression has been observed in many tumors (Vita & Henriksson, 2006, Semin Cancer Biol, 16:318-30; Wade & Wahl, 2006, Curr Top Microbiol Immunol, 302:169-203). Myc is a target of nuclear β-catenin and is upregulated in a large proportion of colon tumors, especially tumors with mutated APC and strong nuclear β-catenin signaling (Liu et al., 2006, Adv Anat Pathol, 13:270-4; Reichling et al., 2005, Cancer Res, 65:166-76).

In certain embodiments of the present invention, colon cancer stem cell expression comprises elevated levels of SRY-box 9 (SOX9) compared to non-tumorigenic colon tumor cells. SOX9 is believed to be important for cell fate decisions during organogenesis. In particular, SOX9 plays an important role in chondrogenesis and testicular maturation (Hardingham et al., 2006, J Anat, 209:469; Kobayashi et al., 2005, Ann N Y Acad Sci, 1061:9-17). SOX9 is an important intestinal crypt differentiation factor (Blache et al., 2004, J Cell Biol, 166:37-47) and represses the CDX2 and MUC2 genes, normally expressed in mature villus cells. Repression of differentiation in this manner may promote accumulation of undifferentiated intestinal cells, manifesting as neoplasia.

In certain embodiments of the present invention, colon cancer stem cell expression comprises elevated levels of serine/threonin kinase receptor associated protein (STRAP) compared to non-tumorigenic colon tumor cells. STRAP is a WD40 repeat protein that mediates TGF-β signaling via PDK1 in a phosphatidylinositol 3-kinase dependent manner (Seong et al., 2005, J Biol Chem, 280:42897-908). STRAP may also mediated repression of TGF-β signaling, as it recruits the inhibitory Smad7 protein to type I and II TGF-β receptors (Datta & Moses, 2000, Mol Cell Biol, 20:3157-67). Not only has STRAP amplification been observed in colorectal cancer (Buess et al., 2004, Neoplasia, 6:813-20), but STRAP has recently been described as an oncogene that is up-regulated in 60% of colon and 78% of lung carcinomas (Halder et al., 2006, Cancer Res, 66:6156-66).

In certain embodiments of the present invention, colon cancer stem cell expression comprises elevated levels of CD59 compared to non-tumorigenic colon tumor cells. CD59 binds to complement C8 and C9 components, thereby inhibiting complement-mediated lysis (Longhi M P, Harris C L, Morgan B P, Gallimore A. Trends Immunol. (2006) 27:102-108; Cole D S, Morgan B P. Clin Sci (Lond) (2003) 104:455-466). Because of this role, it is also known as membrane inhibitor of reactive lysis (MIRL) or membrane-attack-complex-inhibitory factor (MACIF). Its molecular weight is ~19 kDa and is a GPI-linked glycoprotein expressed on a variety of cell types, including hematopoietic and non-hematopoietic cells. Recently, CD59 has been shown to modulate adaptive immune responses by inhibiting CD4+ T-cell activation (Longhi M P, Harris C L, Morgan B P, Gallimore A. Trends Immunol. (2006) 27:102-108). As a result of these functions, higher expression of CD59 on colon cancer stem cells may promote cell survival by diminishing T-cell responses to abnormal antigen presentation by MHC class II molecules and preventing complement mediated lysis (Knutson K L, Disis M L., Curr Drug Targets Immune Endocr Metabol Disord. (2005) 5:365-371). In support of this argument, resistance to Rituximab can be overcome when neutralizing CD59 antibodies are present (Cerny T, Borisch B, Introna M, Johnson P, Rose A L., Anticancer Drugs. (2002) 13 Suppl 2:S3-10). Furthermore, CD59 mRNA expression is higher in metastatic vs. non-metastatic prostate cancer cells (Loberg R D, Wojno K J, Day L L, Pienta K J., Urology. (2005) 66:1321-1326), and may provide metastatic cells with a protective advantage. Finally, Prod 1, a newt orthologue of mammalian CD59, has been demonstrated to have an important role in tissue patterning during appendage regeneration (Brockes J P, Kumar A., Science (2005) 310:1919-1923). These studies suggest that CD59 has an important role in tumorigenesis via enhancement of survival, immune-response evasion and stem cell biology.

In certain embodiments of the present invention, colon cancer stem cell expression comprises repressed levels of transcription factor 4 (TCF4) compared to non-tumorigenic colon tumor cells. TCF4 is a basic helix-loop-helix (bHLH) transcription factor that recognizes Ephrussi-box (E-box) binding sites and activates transcription when complexed with other TCF family members and β-catenin (Barker et al., 2000, Adv Cancer Res, 77:1-24). Constitutive TCF4/β-catenin complexes are thought to be present in the majority of colon tumors due to APC mutations and constitutive nuclear localization of β-catenin (Clevers, 2004, Cancer Cell, 5:5-6). This interaction results in dysregulation of many genes, including MYC, and a proliferative phenotype. While disruption of this complex can reverse the proliferative phenotype, the effect of reduced TCF4 for β-catenin association and action in the nucleus is unknown.

In certain embodiments of the present invention, colon cancer stem cell expression comprises repressed levels of vimentin (VIM) compared to non-tumorigenic colon tumor cells. Vimentin is an intermediate filament predominantly present in mesenchymal tissue. In benign hyperplastic colon polyps, vimentin is consistently present and is likely a marker of differentiated colon cells (Groisman et al., 2006, Histopathology, 48:431-7). VIM has been identified as a target of TCF4/β-catenin complexes (Gilles et al., 2003, Cancer Res, 63:2658-64), and thus its repressed expression in TG cells may correlate with reduced levels of TCF4 (see above). It is also of interest that the epithelial to mesenchymal switch that accompanies aggressive and metastatic phenotypes of many tumors is characterized by a loss of E-cadherin and increase in vimentin expression (Huber et al., 2005, Curr Opin Cell Biol, 17:1-11). Thus the opposite expression profile in most TG vs NTG profiles may reflect the early stage of colon cancer stem cells in the progression to an advanced and aggressive disease state.

In certain embodiments of the present invention, colon cancer stem cell expression comprises elevated levels of BMPR1A compared to non-tumorigenic colon tumor cells.

In certain embodiments of the present invention, colon cancer stem cells expression comprises elevated levels of ALDH activity.

(1) The BMP Signaling Pathway and Cancer

Bone morphogenetic proteins (BMPs) are multi-functional growth factors of the transforming growth factor-β (TGF-β superfamily. The TGF-β pathway regulates numerous processes including: cellular proliferation, adhesion and differentiation; hematopoiesis; inflammation; skeletal development and tissue homeostasis with BMP signaling playing critical roles in heart, neural and cartilage development, postnatal bone formation, and regulation of hematopoietic and intestinal stem cell behavior (Waite & Eng, 2003, Nat. Rev. Genet. 4:763; Chen et al., 2004, Growth Factors 22:233-41; He et al., 2005, Ann. N.Y. Acad. Sci. 1049:28-38). Deregulated TGF-β signaling is implicated in a range of human diseases including several cancers suggesting that carcinogenesis may proceed by usurping homeostatic mechanisms controlling normal development and tissue repair by stem cell populations (Beachy et al., 2004, Nature 432:324).

Members of the TGF-β family include the structurally related TGF-β isoforms, activins and BMPs. These secreted cytokines activate heteromeric complexes of type I and type II serine/threonine kinase receptors. The type II receptor kinase is constitutively active and upon ligand binding phosphorylates the type I receptor, activating a downstream signal through cytosolic SMAD proteins. BMPs act through receptor-regulated SMAD 1, 5 and 8 which in turn interact with a common partner SMAD, SMAD4, to regulate transcription (Waite & Eng, 2003, Nat. Rev. Genet. 4:763).

The anti-mitogenic response of cell to TGF-β ligands suggests that pathway components are tumor suppressors with inactivation of the pathway contributing to tumorigenesis (Itoh et al., 2000, Eur. J. Biochem. 267:6954). This has been confirmed in knock-out mice with Smad3-deficient mice developing metastatic colorectal cancer, Smad4 heterozygous mice developing malignant intestinal tumors, and conditional Bmpr1 loss in the epidermis and hair follicles results in hair matrix cell hyperplasia (Zhu et al., 1998, Cell 94:703-14; Takaku et al., 1998, Cell 92:645-56; Ming Kwan et al., 2004, Genesis 39:10-25). In humans, Smad4 is mutated or inactivated in a number of cancers including pancreatic, colon, breast and lung cancers (Hahn et al., 1996, Science 271:350-3; Schutte et al., 1996, Cancer Res. 56:2527-30). Furthermore, germline mutations in the mothers against decapentaplegic homologue 4 gene (MADH4), which encodes SMAD4, and the BMP receptor type IA gene (BMPR1A) are associated with 15-20% and 20-25%, respectively, of juvenile polyposis syndrome (JPS) cases, an autosomal dominant cancer syndrome characterized by gastrointestinal hamartomatous polyps and a high risk of gastrointestinal cancer (Howe et al., 1998, Science 280:1086-8; Howe et al., 2001, Nat. Genet. 28:184-7; Zhou et al., 2001, Am. J. Hum. Genet. 69:704-11).

Though BMP ligands commonly act as negative regulators of cell proliferation and tumor growth (Miyazaki et al., 2004, Oncogene 23:9326-35; Nishanian et al., 2004, Cancer Biol. Ther. 3:667-75; Wen et al., 2004, Biochem. Biophys. Res. Commun. 26:100-6; Baada Ro et al., 2004 Oncogene 23:3024-32), activation of the BMP pathway may play a role in certain cancers. Expression of BMPR1B has been implicated in the progression and dedifferentiation of oestrogen positive breast cancers (Helms et al., 2005, J. Pathol. 206:366-76) and expression of BMP ligands may promote growth of human breast, pancreatic and prostate cancer cells and prevent apoptosis and hypoxic death of cancer cells (Raida et al., 2005, Int. J. Oncol. 26:1465-70; Pouliot et al., 2003, 63:277-81; Kleeff et al., 1999, Gastroenterology 116:1202-16; Ide et al., 1997, Cancer Res. 57:5022-7; Chen et al., 2001, J. Biol. Chem. 276:39259-63; Izumi et al., 2001, J. Biol. Chem. 276:31133-41).

BMP signaling is also involved in vascular development and angiogenesis. BMP-2 enhances neovascularization of developing tumors (Langenfeld & Langenfeld, 2004, Mol. Cancer. Res. 2:141-9), and BMP-7 induces vascular endothelial growth factor (VEGF) in prostate cancer cell lines suggesting a contribution of BMPs to osteoblastic metastases (Dai et al., 2004, Cancer Res. 64:994-9). In humans, germline loss of function mutations in the BMP receptor type II (BMPR2) gene produce an autosomal dominant vascular disorder known as primary pulmonary hypertension (PPH). PPH is characterized by the loss of small pulmonary arteries and arterioles resulting in persistent elevation of pulmonary vascular resistance, pulmonary hypertension and heart failure. Pulmonary vascular endothelial hyperproliferation is observed in PPH patients, suggesting that some BMP ligands may act as vascular growth suppressors (Waite & Eng, 2003, Nat. Rev. Genet. 4:763).

The identification of BMPR1A as upregulated in colon cancer stem cells suggests that targeting the BMP pathway may help eliminate tumorigenic cells responsible for the formation and reoccurrence of solid tumors. Furthermore, because of the prominent role of angiogenesis in tumor formation and maintenance, targeting the BMP pathway may also inhibit angiogenesis, starving a cancer of nutrients and contributing to its elimination.

In other embodiments of the present invention, colon cancer stem cell expression comprises elevated levels of the Wnt receptor FZD6 compared to non-tumorigenic colon tumor cell. In yet other embodiments of the present invention, colon cancer stem cell expression comprises elevated levels of the Wnt receptor FZD7 compared to non-tumorigenic colon tumor cell (2) The Wnt Signaling Pathway and Cancer The Wnt signaling pathway is one of several critical regulators of embryonic pattern formation, post-embryonic tissue maintenance, and stem cell biology. More specifically, Wnt signaling plays an important role in the generation of cell polarity and cell fate specification including self-renewal by stem cell populations. Unregulated activation of the Wnt pathway is associated with numerous human cancers where it may alter the developmental fate of tumor cells to maintain them in an undifferentiated and proliferative state. Thus carcinogenesis may proceed by usurping homeostatic mechanisms controlling normal development and tissue repair by stem cells (reviewed in Reya & Clevers, 2005, Nature 434:843; Beachy et al., (04) Nature 432:324).

The Wnt signaling pathway was first elucidated in the *Drosophila* developmental mutant wingless (wg) and from the murine proto-oncogene int-1, now Wnt1 (Nusse & Varmus, 1982, Cell 31:99-109; Van Ooyen & Nusse, 1984, Cell 39:233-40; Cabrera et al., 1987, Cell 50:659-63; Rijsewijk et al., 1987, Cell 50:649-57). Wnt genes encode secreted lipid-modified glycoproteins of which 19 have been identified in mammals. These secreted ligands activate a receptor complex consisting of a Frizzled (Fzd) receptor family member and low-density lipoprotein (LDL) receptor-related protein 5 or 6 (LPR5/6). The Fzd receptors are seven transmembrane domain proteins of the G-protein coupled receptor (GPCR) superfamily and contain a large extracellular N-terminal ligand binding domain with 10 conserved cysteines, known as a cysteine-rich domain (CRD) or Fzd domain. Different Fzd CRDs have different binding affinities for specific Wnts (Wu & Nusse, 2002, J. Biol. Chem. 277:41762-9), and Fzd receptors have been grouped into those that activate the canonical β-catenin pathway and those that activate non-canonical pathways described below (Miller et al., 1999, Oncogene 18:7860-72). FZD6 and FZD7 are two of ten identified human Wnt receptors. LRP5/6 are single pass transmembrane proteins with four extracellular EGF-like domains separated by six YWTD amino acid repeats that contribute to Fzd and ligand binding (Johnson et al., 2004, J. Bone Mineral Res 19:1749).

The canonical Wnt signaling pathway activated upon receptor binding is mediated by the cytoplasmic protein Dishevelled (Dsh) interacting directly with the Fzd receptor and results in the cytoplasmic stabilization and accumulation of β-catenin. In the absence of a Wnt signal, β-catenin is localized to a cytoplasmic destruction complex that includes the tumor suppressor proteins adenomatous polyposis coli (APC) and auxin. These proteins function as critical scaffolds to allow glycogen synthase kinase (GSK)-3β to bind and phosphorylate β-catenin, marking it for degradation via the ubiquitin/proteasome pathway. Activation of Dsh results in phosphorylation of GSK3β and the dissociation of the destruction complex. Accumulated cytoplasmic β-catenin is then transported into the nucleus where it interacts with the DNA-binding proteins of the Tcf/Lef family to activate transcription.

In addition to the canonical signaling pathway, Wnt ligands also active β-catenin-independent pathways (Veeman et al., 2003, Dev. Cell 5:367-77). Non-canonical Wnt signaling has been implicated in numerous processes but most convincingly in gastrulation movements via a mechanism similar to the *Drosophila* planar cell polarity (PCP) pathway. Other potential mechanisms of non-canonical Wnt signaling include calcium flux, JNK, and both small and heterotrimeric G-proteins. Antagonism is often observed between the canonical and non-canonical pathways, and some evidence indicates that non-canonical signaling may suppress cancer formation (Olson & Gibo, 1998, Exp. Cell Res. 241:134; Topol et al., 2003, J. Cell Biol. 162:899-908).

Hematopoietic stem cells (HSCs) are the best understood stem cells in the body, and Wnt signaling is implicated both in their normal maintenance as well as in leukemic transformation (Reya & Clevers, 2005, Nature 434:843). HSCs are a rare population of cells that reside in a stomal niche within the adult bone marrow. These cells are characterized both by a unique gene expression profile as well as an ability to continuously give rise to more differentiated progenitor cells to reconstitute the entire hematopoietic system. Both HSCs and the cells of their stromal microenvironment express Wnt ligands, and Wnt reporter activation is present in HSCs in vivo. Furthermore, both β-catenin and purified Wnt3A promote self-renewal of murine HSCs in vitro and enhance their ability to reconstitute the hematopoietic system in vivo while Wnt5A promotes expansion of human hematopoietic progenitors in vitro and re-population in a NOD-SCID xenotransplant model (Reya et al., 2003, Nature 423:409-14; Willert et al., 2003, Nature 423:448-52; Van Den Berg et al., 1998, Blood 92:3189-202; Murdoch et al., 2003, PNAS 100: 3422-7).

More recently Wnt signaling has been found to play a role in the oncogenic growth of both myeloid and lymphoid lineages. For example, granulocyte-macrophage progenitors (GMPs) from chronic myelogenous leukemias display activated Wnt signaling on which they are depended for growth and renewal (Jamieson et al., 2004, N. Engl. J. Med. 351:657-67) And while leukemias do not appear to harbor mutations within the Wnt pathway, autocrine and/or paracrine Wnt signaling may sustain cancerous self-renewal (Reya & Clevers 2005, Nature 434:843).

The canonical Wnt signaling pathway also plays a central role in the maintenance of stem cell populations in the small intestine and colon, and the inappropriate activation of this pathway plays a prominent role in colorectal cancers (Reya & Clevers, 2005, Nature 434:843). The absorptive epithelium of the intestines is arranged into villi and crypts. Stem cells reside in the crypts and slowly divide to produce rapidly proliferating cells which give rise to all the differentiated cell populations that move up out of the crypts to occupy the intestinal villi. The Wnt signaling cascade plays a dominant role in controlling cell fates along the crypt-villi axis and is essential for the maintenance of the stem cell population. Disruption of Wnt signaling either by genetic loss of Tcf7/2 by homologous recombination (Korinek et al., 1998, Nat. Genet. 19:379) or overexpression of Dickkopf-1 (Dkk1), a potent secreted Wnt antagonist (Pinto et al., 2003, Genes Dev. 17:1709-13; Kuhnert et al., 2004, PNAS 101:266-71), results in depletion of intestinal stem cell populations.

Colorectal cancer is most commonly initiated by activating mutations in the Wnt signaling cascade. Approximately 5-10% of all colorectal cancers are hereditary with one of the main forms being familial adenomatous polyposis (FAP), an autosomal dominant disease in which about 80% of affected individuals contain a germline mutation in the adenomatous polyposis coli (APC) gene. Mutations have also been identified in other Wnt pathway components including auxin and β-catenin. Individual adenomas are clonal outgrowths of epithelial cell containing a second inactivated allele, and the large number of FAP adenomas inevitably results in the development of adenocarcinomas through addition mutations in oncogenes and/or tumor suppressor genes. Furthermore, activation of the Wnt signaling pathway, including gain-of-function mutations in APC and β-catenin, can induce hyperplastic development and tumor growth in mouse models (Oshima et al., 1997, Cancer Res. 57:1644-9; Harada et al., 1999, EMBO J. 18:5931-42).

A role for Wnt signaling in cancer was first uncovered with the identification of Wnt1 (originally int1) as an oncogene in mammary tumors transformed by the nearby insertion of a murine virus (Nusse & Varmus, 1982, Cell 31:99-109). Additional evidence for the role of Wnt signaling in breast cancer has since accumulated. For instance, transgenic overexpression of β-catenin in the mammary glands results in hyperplasias and adenocarcinomas (Imbert et al., 2001, J. Cell Biol. 153:555-68; Michaelson & Leder, 2001, Oncogene 20:5093-9) whereas loss of Wnt signaling disrupts normal mammary gland development (Tepera et al., 2003, J. Cell Sc. 116:1137-49; Hatsell et al., 2003, J. Mammary Gland Biol. Neoplasia 8:145-58). More recently mammary stem cells have been shown to be activated by Wnt signaling (Liu et al., 2004, PNAS 101:4158). In human breast cancer, β-catenin accumulation implicates activated Wnt signaling in over 50% of carcinomas, and though specific mutations have not been identified, upregulation of Frizzled receptor expression has been observed (Brennan & Brown, 2004, J. Mammary Gland Neoplasia 9:119-31; Malovanovic et al., 2004, Int. J. Oncol. 25:1337-42).

In other embodiments of the present invention, colon cancer stem cell expression comprises elevated levels of Carcinoembryonic antigen-related cell adhesion molecule 6 (CEACAM6; CD66c; NCA) compared to non-tumorigenic colon tumor cells. CEACAM6 is a glycophosphatidylinositol (GPI) anchored immunoglobulin superfamily member found in higher primates that is thought to mediate intercellular interactions (Yasui et al., 2004 Cancer Sci 95:385-92). CEACAM6 is predominantly expressed in the colon where it is a potential target of the TCF-1 transcription factor in colonic crypts where stem cells are believed to reside (Scholzel et al., 2000, Am. J. Pathol. 156:595-605; Liebig et al., 2005, Cancer Lett. 223:159-67; Roose et al., 1999, 285:1923-6). CEACAM6 expression has also been detected in neutrophils. However, whereas other family members, such as CEACAM5 (which also shows increased in expression in colon cancer stem cells) mediate NK-cell inhibitory interactions via CEACAM1 on NK-cells, CEACAM6 does not appear to have this activity (Market et al., 2004, J. Immunol. 173:3732-9)

CEACAM6 is overexpressed in a number of gastrointestinal malignancies (Yasui et al., 2004 Cancer Sci 95:385-92), including colorectal and pancreatic cancers, and this expression correlates with aggressive (usually non-differentiated) tumors (Kodera et al., 1993, Br. J. Cancer 68:130-6; Ilantzis et al., 2002, Neoplasia 4:151-63) in which a high percentage of cancer stem cells are thought to reside. CEACAM6 expression is also highest at the invasion front (Liebig et al., 2005, Cancer Lett. 223:159-67), again the location within colon tumors where we believe cancer stem cells reside. Upregulation of CEACAM6 expression in hyperplastic polyps and early adenomas represents one of the earliest observable molecular events leading to colorectal tumors (Yasui et al., 2004 Cancer Sci 95:385-92), and CEACAM6 expression as an independent marker predicts poor overall survival and disease-free survival (Jantscheff et al., 2003, J. Clin. Oncol. 21:3638-46). Ectopic expression of CEACAM6 facilitates anchorage-independent growth in vitro (i.e. survival) and greater metastatic ability in vivo (Duxbury et al., 2004, Oncogene 23:465-73). Furthermore, repression of CEACAM6 gene expression by siRNA in chemoresistance pancreatic cancer cell lines renders them susceptible to chemotherapy and anoikis, and in vivo prevents liver metastasis (Whang et al., 2005, Annals of Surgery 240:667). Resistance to chemotherapy and anoikis appears to be mediated by c-Src, FAK and Akt, all downstream mediators of integrin signaling suggesting crosstalk between CEACAM6 and the integrins (Duxbury et al., 2004. Biochem Biophys. Res. Commun. 317:133-141; Duxbury et al., 2004, J. Biol. Chem. 279:23176-82). Interestingly integrin expression is significantly higher in tumorigenic vs. nontumorigenic colon tumor cells, as are a number of mediators of integrin signaling including members of the Src-family kinase family. It is possible that high levels of CEACAM6 stimulate non-canonical β-catenin activation in coordination with the integrins, potentially circumventing requirements for canonical β-catenin activation via Wnts and Frizzled receptors.

In certain embodiments of the present invention, colon cancer stem cell expression comprises elevated levels of Notch2 compared to non-tumorigenic colon tumor cells. In other embodiments, colon cancer stem cell expression comprises elevated levels the of Notch ligand JAG1 compared to non-tumorigenic colon tumor cells. In other embodiments, colon cancer stem cell expression comprises elevated levels of HES1 and HES6, which are Notch signaling pathway target genes, compared to non-tumorigenic colon tumor cells. The identification of Notch2, JAG1, Hes1 and Hes6 as upregulated in colon cancer stem cells suggest a role for Notch signaling in colon cancer stem cell biology and cancer.

(3) The Notch Signaling Pathway and Cancer

The Notch signaling pathway is one of several critical regulators of embryonic pattern formation, post-embryonic tissue maintenance, and stem cell biology. More specifically, Notch signaling is involved in the process of lateral inhibition between adjacent cell fates and plays an important role in cell fate determination during asymmetric cell divisions. Unregulated Notch signaling is associated with numerous human cancers where it may alter the developmental fate of tumor cells to maintain them in an undifferentiated and proliferative state (Brennan and Brown, 2003, Breast Cancer Res. 5:69). Thus carcinogenesis may proceed by usurping homeostatic mechanisms controlling normal development and tissue repair by stem cell populations (Beachy et al., 2004, Nature 432:324).

The Notch receptor was first identified in *Drosophila* mutants with haploinsufficiency resulting in notches at the wing margin whereas loss-of-function producing an embryonic lethal "neurogenic" phenotype where cells of the epidermis switch fate to neural tissue (Moohr, 1919, Genet. 4:252; Poulson, 1937, PNAS 23:133; Poulson, 1940, J. Exp. Zool. 83:271). The Notch receptor is a single-pass transmembrane receptor containing numerous tandem epidermal growth factor (EGF)-like repeats and cysteine-rich Notch/LIN-12 repeats within a large extracellular domain (Wharton et al., 1985, Cell 43:567; Kidd et al., 1986, Mol. Cell. Biol. 6:3094; reviewed in Artavanis-Tsakonas et al., 1999, Science 284: 770). Four mammalian Notch proteins have been identified, and mutations in these receptors invariably result in developmental abnormalities and human pathologies including several cancers as described in detail below (Gridley, 1997, Mol. Cell. Neurosci. 9:103; Joutel & Tournier-Lasserve, 1998, Semin. Cell Dev. Biol. 9:619-25).

The Notch receptor is activated by single-pass transmembrane ligands of the Delta, Serrated, Lag-2 (DSL) family. There are five known Notch ligands in mammals: Delta-like 1 (Dl11), Delta-like 3 (Dl13), Delta-like 4 (Dl14), Jagged 1 and Jagged 2 characterized by a DSL domain and tandem EGF-like repeats within the extracellular domain. The extracellular domain of the Notch receptor interacts with that of its ligands, typically on adjacent cells, resulting in two proteolytic cleaveages of Notch, one extracellular mediated by an ADAM protease and one within the transmembrane domain mediated by gamma secretase. This latter cleavage generates the Notch intracellular domain (NICD), which then enters the nucleus where it activates the CBF1, Suppressor of Hairless [Su(H)], Lag-2 (CSL) family of transcription factors (or RBP-J) as the major downstream effectors to increase transcription of nuclear basic helix-loop-helix transcription factors of the Hairy and Enhancer of Split [E(spl)] family (Artavanis-Tsakonas et al., 1999, Science 284:770; Brennan and Brown, 2003, Breast Cancer Res. 5:69; Iso et al., 2003, Arterioscler. Thromb. Vasc. Biol. 23:543).

Hematopoietic stem cells (HSCs) are the best understood stem cells in the body, and Notch signaling is implicated both in their normal maintenance as well as in leukemic transformation (Kopper & Hajdu, 2004, Pathol. Oncol. Res. 10:69-73). HSCs are a rare population of cells that reside in a stomal niche within the adult bone marrow. These cells are characterized both by a unique gene expression profile as well as an ability to continuously give rise to more differentiated progenitor cells to reconstitute the entire hematopoietic system. Constitutive activation of Notch1 signaling in HSCs and progenitors cells establishes immortalized cell lines that generate both lymphoid and myeloid cells in vitro and in long-term reconstitution assays (Varnum-Finney et al., 2000, Nat. Med. 6:1278-81), and the presence of Jagged 1 increases engraftment of human bone marrow cell populations enriched for HSCs (Karanu et al., 2000, J. Exp. Med. 192:1365-72). More recently, Notch signaling has been demonstrate in HSCs in vivo and shown to be involved in inhibiting HSC differentiation. Furthermore, Notch signaling appears to be required for Wnt-mediated HSC self-renewal (Duncan et al., 2005, Nat. Immunol. 6:314).

The Notch signaling pathway also plays a central role in the maintenance of neural stem cells is implicated both in their normal maintenance as well as in brain cancers (Kopper & Hajdu, 2004, Pathol. Oncol. Res. 10:69-73; Purow et al., 2005, Cancer Res. 65:2353-63; Hallahan et al., 2004, Cancer Res. 64:7794-800). Neural stem cells give rise to all neuronal and glial cells in the mammalian nervous system during development, and more recently have been identified in the adult brain (Gage, 2000, Science 287:1433-8). Mice deficient for Notch1; the Notch target genes Hes1, 3, and 5; and a regulator of Notch signaling presenilin1 (PS1) show decreased numbers of embryonic neural stem cells. Furthermore, adult neural stem cells are reduced in the brains of PS1 heterozygote mice (Nakamura et al., 2000, J. Neurosci. 20:283-93; Hitoshi et al., 2002, Genes Dev. 16:846-58). The reduction in neural stem cells appears to result from their premature differentiation into neurons (Hatakeyama et al., 2004, Dev. 131:5539-50) suggesting that Notch signaling regulates neural stem cell differentiation and self-renewal.

In the gastrointestinal track, it is the Wnt signaling pathway that appears to play the major role in maintaining stem cell populations and in controlling cell fate along the crypt-villus axis. Furthermore, inappropriate activation of the Wnt pathway plays a prominent role in colorectal cancers (Reya & Clevers, 2005, Nature 434:843). Here Notch signaling is involved in inhibiting stem cell differentiation into non-secretory absorptive enterocytes cells and promoting differentiation of secretory cell types, including enteroendocrines and goblet cells (Schonhoff et al., 2004, Endocrinol. 145:2639-44), and new evidence suggests that Notch signaling may also be required for the maintenance of stem cells (van Es et al., 2005, Nature, 435:959). Specifically, activation of Notch signaling by transgenic expression of the Notch intracellular domain in the intestinal epithelium blocks secretory cell differentiation and expands the progenitor cell population (Fre et al., 2005, Nature 435). Conversely, conditional loss of the common Notch activated transcription factor CSL/RBP-J in the intestines or treatment with a gamma-secretase inhibitor, both of which abolish Notch signaling, result in a rapid and extensive conversion of proliferative crypt cells into goblet cell, and gamma-secretase inhibitors could also convert proliferative adenoma cells into post-mitotic goblet cells in a mouse model of colon cancer (van Es et al., 2005, Nature, 435:959). Furthermore, the Notch activated Hairy and Enhancer of Split [E(spl)] family transcription factor Hes6 is expressed in the proliferative cell domain and lost in the absence of CSL/RBP-J suggesting that Hes6 may regulate intestinal epithelial cell fate decisions and stem cell maintenance downstream of Notch (van Es et al., 2005, Nature, 435:959). Hes6 has been identified as a gene upregulated in both colon metastases and in primary tumors derived from the lung, breast, and kidney (Swearingen et al., 2003, Cancer Lett. 198:229-39). The identification by the present invention of the upregulation of Hes6 as a colon cancer stem cells, and thus as a colon cancer stem cell marker, suggests its use in characterizing, diagnosing, and treating colon cancers.

(4) Aldehyde Dehydrogenase

Intracellular aldehyde dehydrogenases (ALDH) enzymes oxidize aldehydes to carboxylic acids and carry out various catabolic processes, including ethanol and amine catabolism and conversion of vitamin A to retinoic acid (Labrecque J, Bhat P V, Lacroix A., Biochem Cell Biol. (1993) 71:85-89; Russo J E, Hilton J., Cancer Res. (1988) 48:2963-2968). High levels of the ALDH enzyme protect hematopoietic stem cells (HSC) and intestinal crypt cells from the cytotoxic effects of cyclophosphamide (CPA) in procedures that purge grafts of tumor cells (Colvin O M, Pharmacological Purging of the Bone Marrow (2d ed.) Blackwell Sciences Inc. (1999); Russo J E, Hilton J, Colvin O M, Prog. Clin. Biol. Res. (1989) 290:65-79). Because of high ALDH activity in HSC (Kastan M B, Schlaffer E, Russo J E, Colvin O M, Civin C I, Hilton J, Blood (1990) 75:1947-1950), fluorescent ALDH substrates can be used for HSC purification (Storms R W, Trujillo A P, Springer J B, et al., Proc. Natl. Acad. Sci. USA. (1999) 96:9118-9123). Specifically, Aldefluor™ (StemCo Biomedical; Durham, N.C.), a non-toxic ALDH substrate consisting of a BODIPY-conjugated aminoacetaldehyde, can be used in conjunction with fluorescence activated cell sorting (FACS) through the combination of ALDH-dependent increases in Aldefluor™ fluorescence with the low side scatter characteristics of stem cell populations such as HSC and neural stem cells (Cai J, Cheng A, Luo Y, et al., J, Neurochem. (2004) 88:212-226).

Humans have nineteen ALDH family member genes. Though the exact repertoire of ALDH family member gene products capable of Aldefluor™ processing remains unclear, ALDH1 is believed to be a substrate for Aldefluor™ and ALDH1 mRNA and protein levels correlate with resistance to CPA (Magni M, Shammah S, Schiro R, Mellado W, Dalla-Favera R, Gianni A M., Blood (1996) 87:1097-1103; Moreb J S, Turner C, Sreerama L, Zucali J R, Sladek N E, Schweder M., Leuk. Lymphoma (1995) 20:77-84; Quash G, Fournet G, Chantepie J, et al., Biochem. Pharmacol. (2002) 64:1279-1292; Sladek N E, Kollander R, Sreerama L, Kiang D T. Cancer Chemother. Pharmacol. (2002) 49:309-321; Yang X W, Wang W, Fu J X, et al., Zhongguo Shi Yan Xue Ye Xue Za Zhi. (2002) 10:205-208). Procedurally, ALDH-specific increases in Aldefluor™ fluorescence observed by FACS are determined against a control containing a competitive inhibitor of ALDH; diethylaminobenzaldehyde (DEAB). Recent studies involving DEAB suggest an important role for ALDH enzymes in determining HSC fate, and specifically that HSC differentiation requires the retinoic acids generated by intracellular ALDH (Chute J P, Muramoto G G, Whitesides J, et al., Proc. Natl. Acad. Sci. USA. (2006) 103:11707-12.

Additional solid tumor stem cells cancer markers can be identified, for example, using the methods described in Example 2 below.

The invention for the first time identifies colon cancer stem cell markers that are upregulated in colon cancer stem cells compared to nontumorigenic colon tumor cells. These markers can be used to provide a diagnosis, prognosis, and/or select a therapy based on the identification and quantification of colon cancer stem cells in a tumor as well as to monitor a diagnosis, prognosis, and/or therapy over time. If it is known that a patient has a tumor that contains a significant number of colon cancer stem cells, a more aggressive approach to therapy can be warranted than in tumors that contain a smaller number of colon cancer stem cells. For example, in patients where there is no evidence of disease in lymph nodes (node-negative patients), a decision must be made regarding whether to administer chemotherapy (adjuvant therapy) following surgical removal of the tumor. While some patients are likely to benefit from such treatment, it has significant side effects and can preferably be avoided by patients with tumors that contain few cancer stem cells. Presently it is difficult or impossible to predict which patients would benefit. Detecting and quantifying the number of cancer stem cell in a patient can help in this decision. Furthermore, detecting the colon cancer stem cell markers of the present invention can provide information related to tumor progression. It is well known that as tumors progress, their phenotypic characteristics may change. The invention thus contemplates the possibility that colon tumors may evolve from containing a small number of colon cancer stem cells to containing a larger number (or vice versa) either in response to therapy or in response to lack of therapy. Thus detection of colon cancer stem cell markers can be used to detect such progression and alter therapy accordingly.

It is well known in the art that some tumors respond to certain therapies while others do not. At present there is very little information that may be used to determine, prior to treatment, the likelihood that a specific tumor will respond to a given therapeutic agent. Many compounds have been tested for anti-tumor activity and appear to be effective in only a small percentage of tumors. Due to the current inability to predict which tumors will respond to a given agent, these compounds have not been developed into marketed therapeutics. This problem reflects the fact that current methods of classifying tumors are limited. However, the present invention offers the possibility of characterizing tumors based on the presence of cancer stem cell markers and thus increasing the likelihood of response to a given agent. Tumor sample archives containing tissue samples obtained from patients that have undergone therapy with various agents are available along with information regarding the results of such therapy. In general such archives consist of tumor samples embedded in paraffin blocks. These tumor samples can be analyzed for their expression of colon cancer stem cell marker polypeptides of the present invention. For example, immunohistochemistry can be performed using antibodies that bind to the polypeptides. Alternatively these tumor samples can be analyzed by their expression of polynucleotides of a colon cancer stem cell marker of the present invention. For example, RNA can be extracted from the tumor sample and RT-PCR used to quantitatively amplify colon cancer stem cell marker mRNAs. It is then possible to correlate the expression of colon cancer stem cell markers with the response of the tumor to therapy, thereby identifying particular compounds that show a superior efficacy against colon cancer stem cells. Once such compounds are identified it will be possible to select patients for additional clinical trials using these compounds. Such clinical trials, performed on a selected group of patients, are more likely to demonstrate efficacy. The reagents provided herein, therefore, are valuable both for retrospective and prospective trials.

In certain embodiments of the present invention, colon cancer stem cell markers can be used experimentally to test and assess lead compounds including, for example, small molecules, siRNAs, and antibodies for the treatment of cancer. For example tumor cells from a patient can be screened for colon cancer stem cells and then transplanted into the xenograft model described herein and the effect of test compounds, such as for example antibodies against one or more of the colon cancer stem cell markers described herein, tested for effects on tumor growth and survival. Furthermore the number of colon cancer stem cells can be determined following treatment to assess the effectiveness of the therapy on targeting cancer stem cells and used to guide a future treatment regimen.

Detection of Solid Tumor Stem Cell Cancer Markers

In some embodiments, the present invention provides methods for detection of expression of stem cell cancer markers (e.g., breast cancer stem cell cancer markers). In some embodiments, expression is measured directly (e.g., at the RNA or protein level). In some embodiments, expression is detected in tissue samples (e.g., biopsy tissue). In other embodiments, expression is detected in bodily fluids (e.g., including but not limited to, plasma, serum, whole blood, mucus, and urine). The present invention further provides panels and kits for the detection of markers. In some embodiments, the presence of a stem cell cancer marker is used to provide a prognosis to a subject. The information provided is also used to direct the course of treatment. For example, if a subject is found to have a marker indicative of a solid tumor stem cell (see, e.g. Tables 4-9), additional therapies (e.g., hormonal or radiation therapies) can be started at an earlier point when they are more likely to be effective (e.g., before metastasis). In addition, if a subject is found to have a tumor that is not responsive to hormonal therapy, the expense and inconvenience of such therapies can be avoided.

The present invention is not limited to the markers described above. Any suitable marker that correlates with cancer or the progression of cancer can be utilized. Additional markers are also contemplated to be within the scope of the present invention. Any suitable method can be utilized to identify and characterize cancer markers suitable for use in the methods of the present invention, including but not limited to, those described in illustrative Example 4 below. For example, in some embodiments, markers identified as being up or down-regulated in solid tumor stem cells using the gene expression microarray methods of the present invention are further characterized using tissue microarray, immunohistochemistry, Northern blot analysis, siRNA or antisense RNA inhibition, mutation analysis, investigation of expression with clinical outcome, as well as other methods disclosed herein.

In some embodiments, the present invention provides a panel for the analysis of a plurality of markers. The panel allows for the simultaneous analysis of multiple markers correlating with carcinogenesis and/or metastasis. Depending on the subject, panels can be analyzed alone or in combination in order to provide the best possible diagnosis and prognosis. Markers for inclusion on a panel are selected by screening for their predictive value using any suitable method, including but not limited to, those described in the illustrative examples below.

1. Detection of RNA

In some embodiments, detection of solid tumor stem cell cancer markers (e.g., including but not limited to, those disclosed in Tables 4-9) are detected by measuring the expression of corresponding mRNA in a tissue sample (e.g., breast cancer tissue). mRNA expression can be measured by any suitable method, including but not limited to, those disclosed below.

In some embodiments, RNA is detection by Northern blot analysis. Northern blot analysis involves the separation of RNA and hybridization of a complementary labeled probe.

In still further embodiments, RNA (or corresponding cDNA) is detected by hybridization to an oligonucleotide probe). A variety of hybridization assays using a variety of technologies for hybridization and detection are available. For example, in some embodiments, TaqMan assay (PE Biosystems, Foster City, Calif.; See e.g., U.S. Pat. Nos. 5,962,233 and 5,538,848, each of which is herein incorporated by reference) is utilized. The assay is performed during a PCR reaction. The TaqMan assay exploits the 5'-3' exonuclease activity of the AMPLITAQ GOLD DNA polymerase. A probe consisting of an oligonucleotide with a 5'-reporter dye (e.g., a fluorescent dye) and a 3'-quencher dye is included in the PCR reaction. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In yet other embodiments, reverse-transcriptase PCR (RT-PCR) is used to detect the expression of RNA. In RT-PCR, RNA is enzymatically converted to complementary DNA or "cDNA" using a reverse transcriptase enzyme. The cDNA is then used as a template for a PCR reaction. PCR products can be detected by any suitable method, including but not limited to, gel electrophoresis and staining with a DNA specific stain or hybridization to a labeled probe. In some embodiments, the quantitative reverse transcriptase PCR with standardized mixtures of competitive templates method described in U.S. Pat. Nos. 5,639,606, 5,643,765, and 5,876,978 (each of which is herein incorporated by reference) is utilized.

2. Detection of Protein

In other embodiments, gene expression of stem cell cancer markers is detected by measuring the expression of the corresponding protein or polypeptide. Protein expression can be detected by any suitable method. In some embodiments, proteins are detected by immunohistochemistry. In other embodiments, proteins are detected by their binding to an antibody raised against the protein. The generation of antibodies is described below.

Antibody binding is detected by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many methods are known in the art for detecting binding in an immunoassay and are within the scope of the present invention.

In some embodiments, an automated detection assay is utilized. Methods for the automation of immunoassays include those described in U.S. Pat. Nos. 5,885,530, 4,981,785, 6,159,750, and 5,358,691, each of which is herein incorporated by reference. In some embodiments, the analysis and presentation of results is also automated. For example, in some embodiments, software that generates a prognosis based on the presence or absence of a series of proteins corresponding to cancer markers is utilized.

In other embodiments, the immunoassay described in U.S. Pat. Nos. 5,599,677 and 5,672,480; each of which is herein incorporated by reference.

3. cDNA Microarray Technology cDNA microarrays consist of multiple (usually thousands) of different cDNAs spotted (usually using a robotic spotting device) onto known locations on a solid support, such as a glass microscope slide. The cDNAs are typically obtained by PCR amplification of plasmid library inserts using primers complementary to the vector backbone portion of the plasmid or to the gene itself for genes where sequence is known. PCR products suitable for production of microarrays are typically between 0.5 and 2.5 kB in length Full length cDNAs, expressed sequence tags (ESTs), or randomly chosen cDNAs from any library of interest can be chosen. ESTs are partially sequenced cDNAs as described, for example, in Hillier, et al., 1996, 6:807-828. Although some ESTs correspond to known genes, frequently very little or no information regarding any particular EST is available except for a small amount of 3' and/or 5' sequence and, possibly, the tissue of origin of the mRNA from which the EST was derived. As will be appreciated by one of ordinary skill in the art, in general the cDNAs contain sufficient sequence information to uniquely identify a gene within the human genome. Furthermore, in general the cDNAs are of sufficient length to hybridize, selectively, specifically or uniquely, to cDNA obtained from mRNA derived from a single gene under the hybridization conditions of the experiment.

In a typical microarray experiment, a microarray is hybridized with differentially labeled RNA, DNA, or cDNA populations derived from two different samples. Most commonly RNA (either total RNA or poly A+ RNA) is isolated from cells or tissues of interest and is reverse transcribed to yield cDNA. Labeling is usually performed during reverse transcription by incorporating a labeled nucleotide in the reaction mixture. Although various labels can be used, most commonly the nucleotide is conjugated with the fluorescent dyes Cy3 or Cy5. For example, Cy5-dUTP and Cy3-dUTP can be used. cDNA derived from one sample (representing, for example, a particular cell type, tissue type or growth condition) is labeled with one fluorophore while cDNA derived from a second sample (representing, for example, a different cell type, tissue type, or growth condition) is labeled with the second fluorophore. Similar amounts of labeled material from the two samples are cohybridized to the microarray. In the case of a microarray experiment in which the samples are labeled with Cy5 (which fluoresces red) and Cy3 (which fluoresces green), the primary data (obtained by scanning the microarray using a detector capable of quantitatively detecting fluorescence intensity) are ratios of fluorescence intensity (red/green, R/G). These ratios represent the relative concentrations of cDNA molecules that hybridized to the cDNAs represented on the microarray and thus reflect the relative expression levels of the mRNA corresponding to each cDNA/gene represented on the microarray.

Each microarray experiment can provide tens of thousands of data points, each representing the relative expression of a particular gene in the two samples. Appropriate organization and analysis of the data is of key importance, and various computer programs that incorporate standard statistical tools have been developed to facilitate data analysis. One basis for organizing gene expression data is to group genes with similar expression patterns together into clusters. A method for performing hierarchical cluster analysis and display of data derived from microarray experiments is described in Eisen et al., 1998, PNAS 95:14863-14868. As described therein, clustering can be combined with a graphical representation of the primary data in which each data point is represented with a color that quantitatively and qualitatively represents that data point. By converting the data from a large table of numbers into a visual format, this process facilitates an intuitive analysis of the data. Additional information and details regarding the mathematical tools and/or the clustering approach itself can be found, for example, in Sokal & Sneath, Principles of numerical taxonomy, xvi, 359, W. H. Freeman, San Francisco, 1963; Hartigan, Clustering algorithms, xiii, 351, Wiley, New York, 1975; Paull et al., 1989, J. Natl. Cancer Inst. 81:1088-92; Weinstein et al. 1992, Science 258:447-51; van Osdol et al., 1994, J. Natl. Cancer Inst. 86:1853-9; and Weinstein et al., 1997, Science, 275:343-9.

Further details of the experimental methods used in the present invention are found in the Examples. Additional information describing methods for fabricating and using microarrays is found in U.S. Pat. No. 5,807,522, which is herein incorporated by reference. Instructions for constructing microarray hardware (e.g., arrayers and scanners) using commercially available parts can be found at http://cmgm.stanford.edu/pbr-own/ and in Cheung et al., 1999, Nat. Genet. Supplement 21:15-19, which are herein incorporated by reference. Additional discussions of microarray technology and protocols for preparing samples and performing microarray experiments are found in, for example, DNA arrays for analysis of gene expression, Methods Enzymol, 303:179-205, 1999; Fluorescence-based expression monitoring using microarrays, Methods Enzymol, 306: 3-18, 1999; and M. Schena (ed.), DNA Microarrays: A Practical Approach, Oxford University Press, Oxford, UK, 1999. Descriptions of how to use an arrayer and the associated software are found at http://cmgm.stanford.edu/pbrown/mguide/a-rrayerHTML/ArrayerDocs.html, which is herein incorporated by reference.

4. Data Analysis

In some embodiments, a computer-based analysis program is used to translate the raw data generated by the detection assay (e.g., the presence, absence, or amount of a given marker or markers) into data of predictive value for a clinician. The clinician can access the predictive data using any suitable means. Thus, in some embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject can visit a medical center to have the sample obtained and sent to the profiling center, or subjects can collect the sample themselves and directly send it to a profiling center. Where the sample comprises previously determined biological information, the information can be directly sent to the profiling service by the subject (e.g., an information card containing the information can be scanned by a computer and the data transmitted to a computer of the profiling center using an electronic communication system). Once received by the profiling service, the sample is processed and a profile is produced (e.g., expression data), specific for the diagnostic or prognostic information desired for the subject.

The profile data is then prepared in a format suitable for interpretation by a treating clinician. For example, rather than providing raw expression data (e.g. examining a number of the markers described in Tables 4-9), the prepared format can represent a diagnosis or risk assessment for the subject, along with recommendations for particular treatment options. The data can be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject can chose further intervention or counseling based on the results. In some embodiments, the data is used for research use. For example, the data can be used to further optimize the inclusion or elimination of markers as useful indicators of a particular condition or stage of disease.

5. Kits

In yet other embodiments, the present invention provides kits for the detection and characterization of cancer (e.g. for detecting one or more of the markers shown in Tables 4-9, or for modulating the activity of a peptide expressed by one or more of markers shown in Tables 4-9). In some embodiments, the kits contain antibodies specific for a cancer marker, in addition to detection reagents and buffers. In other embodiments, the kits contain reagents specific for the detection of mRNA or cDNA (e.g., oligonucleotide probes or primers). In some embodiments, the kits contain all of the components necessary and/or sufficient to perform a detection assay, including all controls, directions for performing assays, and any necessary software for analysis and presentation of results.

Another embodiment of the present invention comprises a kit to test for the presence of the polynucleotides or proteins, e.g. in a tissue sample or in a body fluid, of a solid tumor stem cell gene signature, such as the alpha-catenin signature. The kit can comprise for example, an antibody for detection of a polypeptide or a probe for detection of a polynucleotide. In addition, the kit can comprise a reference or control sample; instructions for processing samples, performing the test and interpreting the results; and buffers and other reagents necessary for performing the test. In certain embodiments the kit comprises a panel of antibodies for detecting expression of one or more of the proteins encoded by the genes of the alpha-catenin signature. In other embodiments the kit comprises pairs of primers for detecting expression of one or more of the genes of the solid tumor stem cell gene signature. In other embodiments the kit comprises a cDNA or oligonucleotide array for detecting expression of one or more of the genes of the solid tumor stem cell gene signature.

6. In Vivo Imaging

In some embodiments, in vivo imaging techniques are used to visualize the expression of cancer markers in an animal (e.g., a human or non-human mammal). For example, in some embodiments, cancer marker mRNA or protein is labeled using a labeled antibody specific for the cancer marker. A specifically bound and labeled antibody can be detected in an individual using an in vivo imaging method, including, but not limited to, radionuclide imaging, positron emission tomography, computerized axial tomography, X-ray or magnetic resonance imaging method, fluorescence detection, and chemiluminescent detection. Methods for generating antibodies to the cancer markers of the present invention are described below.

The in vivo imaging methods of the present invention are useful in the diagnosis of cancers that express the solid tumor stem cell cancer markers of the present invention (e.g., in breast cancer). In vivo imaging is used to visualize the presence of a marker indicative of the cancer. Such techniques allow for diagnosis without the use of an unpleasant biopsy. The in vivo imaging methods of the present invention are also useful for providing prognoses to cancer patients. For example, the presence of a marker indicative of cancer stem cells can be detected. The in vivo imaging methods of the present invention can further be used to detect metastatic cancers in other parts of the body.

In some embodiments, reagents (e.g., antibodies) specific for the cancer markers of the present invention are fluorescently labeled. The labeled antibodies are introduced into a subject (e.g., orally or parenterally). Fluorescently labeled antibodies are detected using any suitable method (e.g., using the apparatus described in U.S. Pat. No. 6,198,107, herein incorporated by reference).

In other embodiments, antibodies are radioactively labeled. The use of antibodies for in vivo diagnosis is well known in the art. Sumerdon et al., (Nucl. Med. Biol 17:247-254 [1990] have described an optimized antibody-chelator for the radioimmunoscintographic imaging of tumors using Indium-111 as the label. Griffin et al., (J Clin One 9:631-640 [1991]) have described the use of this agent in detecting tumors in patients suspected of having recurrent colorectal cancer. The use of similar agents with paramagnetic ions as labels for magnetic resonance imaging is known in the art (Lauffer, Magnetic Resonance in Medicine 22:339-342 [1991]). The label used will depend on the imaging modality chosen. Radioactive labels such as Indium-111, Technetium-99m, or Iodine-131 can be used for planar scans or single photon emission computed tomography (SPECT). Positron emitting labels such as Fluorine-19 can also be used for positron emission tomography (PET). For MRI, paramagnetic ions such as Gadolinium (III) or Manganese (II) can be used.

Radioactive metals with half-lives ranging from 1 hour to 3.5 days are available for conjugation to antibodies, such as scandium-47 (3.5 days) gallium-67 (2.8 days), gallium-68 (68 minutes), technetiium-99m (6 hours), and indium-111 (3.2 days), of which gallium-67, technetium-99m, and indium-111 are preferable for gamma camera imaging, gallium-68 is preferable for positron emission tomography.

A useful method of labeling antibodies with such radiometals is by means of a bifunctional chelating agent, such as diethylenetriaminepentaacetic acid (DTPA), as described, for example, by Khaw et al. (Science 209:295 [1980]) for In-111 and Tc-99m, and by Scheinberg et al. (Science 215:1511 [1982]). Other chelating agents can also be used, but the 1-(p-carboxymethoxybenzyl)EDTA and the carboxycarbonic anhydride of DTPA are advantageous because their use permits conjugation without affecting the antibody's immunoreactivity substantially.

Another method for coupling DPTA to proteins is by use of the cyclic anhydride of DTPA, as described by Hnatowich et al. (Int. J. Appl. Radiat. Isot. 33:327 [1982]) for labeling of albumin with In-111, but which can be adapted for labeling of antibodies. A suitable method of labeling antibodies with Tc-99m which does not use chelation with DPTA is the pretinning method of Crockford et al., (U.S. Pat. No. 4,323,546, herein incorporated by reference).

A method of labeling immunoglobulins with Tc-99m is that described by Wong et al. (Int. J. Appl. Radiat. Isot., 29:251 [1978]) for plasma protein, and recently applied successfully by Wong et al. (J. Nucl. Med., 23:229 [1981]) for labeling antibodies.

In the case of the radiometals conjugated to the specific antibody, it is likewise desirable to introduce as high a proportion of the radiolabel as possible into the antibody molecule without destroying its immunospecificity. A further improvement can be achieved by effecting radiolabeling in the presence of the specific stem cell cancer marker of the present invention, to insure that the antigen binding site on the antibody will be protected.

In still further embodiments, in vivo biophotonic imaging (Xenogen, Almeda, Calif.) is utilized for in vivo imaging. This real-time in vivo imaging utilizes luciferase. The luciferase gene is incorporated into cells, microorganisms, and animals (e.g., as a fusion protein with a cancer marker of the present invention). When active, it leads to a reaction that emits light. A CCD camera and software is used to capture the image and analyze it.

Antibodies and Antibody Fragments

The present invention provides isolated antibodies against a cancer stem cell marker. The antibody, or antibody fragment, can be any monoclonal or polyclonal antibody that specifically recognizes the described colon cancer stem cell marker. In some embodiments, the present invention provides monoclonal antibodies, or fragments thereof, that specifically bind to a colon cancer stem cell marker polypeptide described herein. In some embodiments, the monoclonal antibodies, or fragments thereof, are chimeric or humanized antibodies that specifically bind to the extracellular domain of a colon cancer stem cell marker polypeptide described herein. In other embodiments, the monoclonal antibodies, or fragments thereof, are human antibodies that specifically bind to the extracellular domain of a colon cancer stem cell marker polypeptide described herein.

The antibodies against a cancer stem cell marker find use in the experimental, diagnostic and therapeutic methods described herein. In certain embodiments, the antibodies of the present invention are used to detect the expression of a colon cancer stem cell marker protein in biological samples such as, for example, a patient tissue biopsy, pleural effusion, or blood sample. Tissue biopsies can be sectioned and protein detected using, for example, immunofluorescence or immunohistochemistry. Alternatively, individual cells from a sample are isolated, and protein expression detected on fixed or live cells by FACS analysis. Furthermore, the antibodies can be used on protein arrays to detect expression of a colon cancer stem cell marker, for example, on tumor cells, in cell lysates, or in other protein samples. In other embodiments, the antibodies of the present invention are used to inhibit the growth of tumor cells by contacting the antibodies with tumor cells either in vitro cell based assays or in vivo animal models. In still other embodiments, the antibodies are used to treat cancer in a human patient by administering a therapeutically effective amount of an antibody against a colon cancer stem cell marker.

Polyclonal antibodies can be prepared by any known method. Polyclonal antibodies can be raised by immunizing an animal (e.g. a rabbit, rat, mouse, donkey, etc) by multiple subcutaneous or intraperitoneal injections of the relevant antigen (a purified peptide fragment, full-length recombinant protein, fusion protein, etc) optionally conjugated to keyhole limpet hemocyanin (KLH), serum albumin, etc. diluted in sterile saline and combined with an adjuvant (e.g. Complete or Incomplete Freund's Adjuvant) to form a stable emulsion. The polyclonal antibody is then recovered from blood, ascites and the like, of an animal so immunized. Collected blood is clotted, and the serum decanted, clarified by centrifugation, and assayed for antibody titer. The polyclonal antibodies can be purified from serum or ascites according to standard methods in the art including affinity chromatography, ion-exchange chromatography, gel electrophoresis, dialysis, etc.

Monoclonal antibodies can be prepared using hybridoma methods, such as those described by Kohler and Milstein (1975) Nature 256:495. Using the hybridoma method, a mouse, hamster, or other appropriate host animal, is immunized as described above to elicit the production by lymphocytes of antibodies that will specifically bind to an immunizing antigen. Alternatively, lymphocytes can be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay such as radioimmunoassay (RIA) or enzyme-linked immunosorbent assay (ELISA) can then be propagated either in vitro culture using standard methods (Goding, Monoclonal Antibodies: Principles and Practice, Academic Press, 1986) or in vivo as ascites tumors in an animal. The monoclonal antibodies can then be purified from the culture medium or ascites fluid as described for polyclonal antibodies above.

Alternatively monoclonal antibodies can also be made using recombinant DNA methods as described in U.S. Pat. No. 4,816,567. The polynucleotides encoding a monoclonal antibody are isolated, such as from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as E. coli cells, simian COS cells, Chinese hamster ovary (CHO) cells, or myeloma cells that do not otherwise produce immunoglobulin protein, monoclonal antibodies are generated by the host cells. Also, recombinant monoclonal antibodies or fragments thereof of the desired species can be isolated from phage display libraries as described (McCafferty et al., 1990, Nature, 348:552-554; Clackson et al., 1991, Nature, 352:624-628; and Marks et al., 1991, J. Mol. Biol., 222:581-597).

The polynucleotide(s) encoding a monoclonal antibody can further be modified in a number of different manners using recombinant DNA technology to generate alternative antibodies. In one embodiment, the constant domains of the light and heavy chains of, for example, a mouse monoclonal antibody can be substituted 1) for those regions of, for example, a human antibody to generate a chimeric antibody or 2) for a non-immunoglobulin polypeptide to generate a fusion antibody. In other embodiments, the constant regions are truncated or removed to generate the desired antibody fragment of a monoclonal antibody. Furthermore, site-directed or high-density mutagenesis of the variable region can be used to optimize specificity, affinity, etc. of a monoclonal antibody.

In some embodiments, of the present invention the monoclonal antibody against a colon cancer stem cell marker is a humanized antibody. Humanized antibodies are antibodies that contain minimal sequences from non-human (e.g murine) antibodies within the variable regions. Such antibodies are used therapeutically to reduce antigenicity and HAMA (human anti-mouse antibody) responses when administered to a human subject. In practice, humanized antibodies are typically human antibodies with minimum to no non-human sequences. A human antibody is an antibody produced by a human or an antibody having an amino acid sequence corresponding to an antibody produced by a human.

Humanized antibodies can be produced using various techniques known in the art. An antibody can be humanized by substituting the CDR of a human antibody with that of a non-human antibody (e.g. mouse, rat, rabbit, hamster, etc.) having the desired specificity, affinity, and capability (Jones et al., 1986, Nature, 321:522-525; Riechmann et al., 1988, Nature, 332:323-327; Verhoeyen et al., 1988, Science, 239:1534-1536). The humanized antibody can be further modified by the substitution of additional residue either in the Fv framework region and/or within the replaced non-human residues to refine and optimize antibody specificity, affinity, and/or capability.

Human antibodies can be directly prepared using various techniques known in the art. Immortalized human B lymphocytes immunized in vitro or isolated from an immunized individual that produce an antibody directed against a target antigen can be generated (See, for example, Cole et al., Monoclonal Antibodies and Cancer Therapy, Alan R. Liss, p. 77 (1985); Boerner et al., 1991, J. Immunol., 147 (1):86-95; and U.S. Pat. No. 5,750,373). Also, the human antibody can be selected from a phage library, where that phage library expresses human antibodies (Vaughan et al., 1996, Nature Biotechnology, 14:309-314; Sheets et al., 1998, PNAS, 95:6157-6162; Hoogenboom and Winter, 1991, J. Mol. Biol., 227:381; Marks et al., 1991, J. Mol. Biol., 222:581). Humanized antibodies can also be made in transgenic mice containing human immunoglobulin loci that are capable upon immunization of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

This invention also encompasses bispecific antibodies that specifically recognize a colon cancer stem cell marker. Bispecific antibodies are antibodies that are capable of specifically recognizing and binding at least two different epitopes. The different epitopes can either be within the same molecule (e.g. the same colon cancer stem cell marker polypeptide) or on different molecules such that both, for example, the antibodies can specifically recognize and bind a colon cancer stem cell marker as well as, for example, 1) an effector molecule on a leukocyte such as a T-cell receptor (e.g. CD3) or Fc receptor (e.g. CD64, CD32, or CD16) or 2) a cytotoxic agent as described in detail below. Bispecific antibodies can be intact antibodies or antibody fragments. Techniques for making bispecific antibodies are common in the art (Millstein et al., 1983, Nature 305:537-539; Brennan et al., 1985, Science 229:81; Suresh et al, 1986, Methods in Enzymol. 121:120; Traunecker et al., 1991, EMBO J. 10:3655-3659; Shalaby et al., 1992, J. Exp. Med. 175:217-225; Kostelny et al., 1992, J. Immunol. 148:1547-1553; Gruber et al., 1994, J. Immunol. 152:5368; and U.S. Pat. No. 5,731,168).

In certain embodiments of the invention, it may be desirable to use an antibody fragment, rather than an intact antibody, to increase tumor penetration, for example. Various techniques are known for the production of antibody fragments. Traditionally, these fragments are derived via proteolytic digestion of intact antibodies (for example Morimoto et al., 1993, Journal of Biochemical and Biophysical Methods 24:107-117 and Brennan et al., 1985, Science, 229:81). However, these fragments are now typically produced directly by recombinant host cells as described above. Thus Fab, Fv, and scFv antibody fragments can all be expressed in and secreted from E. coli or other host cells, thus allowing the production of large amounts of these fragments. Alternatively, such antibody fragments can be isolated from the antibody phage libraries discussed above. The antibody fragment can also be linear antibodies as described in U.S. Pat. No. 5,641,870, for example, and can be monospecific or bispecific. Other techniques for the production of antibody fragments will be apparent to the skilled practitioner.

It may further be desirable, especially in the case of antibody fragments, to modify an antibody in order to increase its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

The present invention further embraces variants and equivalents which are substantially homologous to the chimeric, humanized and human antibodies, or antibody fragments thereof, set forth herein. These can contain, for example, conservative substitution mutations, i.e. the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid. What is intended by a conservative amino acid substitution is well known in the art.

The invention also pertains to immunoconjugates comprising an antibody conjugated to a cytotoxic agent. Cytotoxic agents include chemotherapeutic agents, growth inhibitory agents, toxins (e.g., an enzymatically active toxin of bacterial, fungal, plant, or animal origin, or fragments thereof), radioactive isotopes (i.e., a radioconjugate), etc. Chemotherapeutic agents useful in the generation of such immunoconjugates include, for example, methotrexate, adriamicin, doxorubicin, melphalan, mitomycin C, chlorambucil, daunorubicin or other intercalating agents. Enzymatically active toxins and fragments thereof that can be used include diphtheria A chain, nonbinding active fragments of diphtheria toxin, exotoxin A chain, ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies including $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). Conjugates of an antibody and one or more small molecule toxins, such as a calicheamicin, maytansinoids, a trichothene, and CC1065, and the derivatives of these toxins that have toxin activity, can also be used.

In some embodiments the antibody of the invention contains human Fc regions that are modified to enhance effector function, for example, antigen-dependent cell-mediated cyotoxicity (ADCC) and/or complement dependent cytotoxicity (CDC). This can be achieved by introducing one or more amino acid substitutions in an Fc region of the antibody. For example, cysteine residue(s) can be introduced in the Fc region to allow interchain disulfide bond formation in this region to improve complement-mediated cell killing and antibody-dependent cellular cytotoxicity (ADCC) (Caron et al., 1992, J. Exp Med. 176:1191-1195; Shopes, 1992, Immunol. 148:2918-2922). Homodimeric antibodies with enhanced anti-tumor activity can also be prepared using heterobifunctional cross-linkers as described in Wolff et al., 1993, Cancer Research 53:2560-2565. Alternatively, an antibody can be engineered which has dual Fc regions (Stevenson et al., 1989, Anti-Cancer Drug Design 3:219-230).

Drug Screening

In some embodiments, the present invention provides drug screening assays (e.g., to screen for anticancer drugs). The screening methods of the present invention utilize stem cell cancer markers identified using the methods of the present invention (e.g., including but not limited to, the stem cell cancer markers shown in Tables 4-9). For example, in some embodiments, the present invention provides methods of screening for compound that alter (e.g., increase or decrease) the expression of stem cell cancer marker genes. In some embodiments, candidate compounds are antisense agents or siRNA agents (e.g., oligonucleotides) directed against cancer markers. In other embodiments, candidate compounds are antibodies that specifically bind to a stem cell cancer marker of the present invention. In certain embodiments, libraries of compounds of small molecules are screened using the methods described herein.

In one screening method, candidate compounds are evaluated for their ability to alter stem cell cancer marker expression by contacting a compound with a cell expressing a stem cell cancer marker and then assaying for the effect of the candidate compounds on expression. In some embodiments, the effect of candidate compounds on expression of a cancer marker gene is assayed by detecting the level of cancer marker mRNA expressed by the cell. mRNA expression can be detected by any suitable method. In other embodiments, the effect of candidate compounds on expression of cancer marker genes is assayed by measuring the level of polypeptide encoded by the cancer markers. The level of polypeptide expressed can be measured using any suitable method, including but not limited to, those disclosed herein. In some embodiments, other changes in cell biology (e.g., apoptosis) are detected.

Specifically, the present invention provides screening methods for identifying modulators, i.e., candidate or test compounds or agents (e.g., proteins, peptides, peptidomimetics, peptoids, small molecules or other drugs) which bind to, or alter the signaling or function associated with the cancer markers of the present invention, have an inhibitory (or stimulatory) effect on, for example, stem cell cancer marker expression or cancer markers activity, or have a stimulatory or inhibitory effect on, for example, the expression or activity of a cancer marker substrate. Compounds thus identified can be used to modulate the activity of target gene products (e.g., stem cell cancer marker genes) either directly or indirectly in a therapeutic protocol, to elaborate the biological function of the target gene product, or to identify compounds that disrupt normal target gene interactions. Compounds which inhibit the activity or expression of cancer markers are useful in the treatment of proliferative disorders, e.g., cancer, particularly metastatic cancer or eliminating or controlling tumor stem cells to prevent or reduce the risk of cancer.

In one embodiment, the invention provides assays for screening candidate or test compounds that are substrates of a cancer markers protein or polypeptide or a biologically active portion thereof. In another embodiment, the invention provides assays for screening candidate or test compounds that bind to or modulate the activity of a cancer marker protein or polypeptide or a biologically active portion thereof.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 [1993]; Erb et al., Proc. Nad. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl. 33.2059 [1994]; Carell et al., Angew. Chem. Int. Ed. Engl. 33:2061 [1994]; and Gallop et al., J. Med. Chem. 37:1233 [1994].

Libraries of compounds can be presented in solution (e.g., Houghten, Biotechniques 13:412-421 [1992]), or on beads (Lam, Nature 354:82-84 [1991]), chips (Fodor, Nature 364: 555-556 [1993]), bacteria or spores (U.S. Pat. No. 5,223,409; herein incorporated by reference), plasmids (Cull et al., Proc. Nad. Acad. Sci. USA 89:18651869 [1992]) or on phage (Scott and Smith, Science 249:386-390 [1990]; Devlin Science 249: 404-406 [1990]; Cwirla et al., Proc. Natl. Acad. Sci. 87:6378-6382 [1990]; Felici, J. Mol. Biol. 222:301 [1991]).

In one embodiment, an assay is a cell-based assay in which a cell that expresses a stem cell cancer marker protein or biologically active portion thereof is contacted with a test compound, and the ability of the test compound to the modulate cancer marker's activity is determined. Determining the ability of the test compound to modulate stem cell cancer marker activity can be accomplished by monitoring, for example, changes in enzymatic activity. The cell, for example, can be of mammalian origin.

The ability of the test compound to modulate cancer marker binding to a compound, e.g., a stem cell cancer marker substrate, can also be evaluated. This can be accomplished, for example, by coupling the compound, e.g., the substrate, with a radioisotope or enzymatic label such that binding of the compound, e.g., the substrate, to a cancer marker can be determined by detecting the labeled compound, e.g., substrate, in a complex.

Alternatively, the stem cell cancer marker is coupled with a radioisotope or enzymatic label to monitor the ability of a test compound to modulate cancer marker binding to a cancer markers substrate in a complex. For example, compounds (e.g., substrates) can be labeled with $^{125}I$, $^{35}S$ $^{14}C$ or $^{3}H$, either directly or indirectly, and the radioisotope detected by direct counting of radioemission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a stem cell cancer marker substrate) to interact with a stem cell cancer marker with or without the labeling of any of the interactants can be evaluated. For example, a microphysiometer can be used to detect the interaction of a compound with a cancer marker without the labeling of either the compound or the cancer marker (McConnell et al. Science 257:1906-1912 [1992]). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and cancer markers.

In yet another embodiment, a cell-free assay is provided in which a cancer marker protein or biologically active portion thereof is contacted with a test compound and the ability of the test compound to bind to the stem cell cancer marker protein or biologically active portion thereof is evaluated. Biologically active portions of the cancer markers proteins to be used in assays of the present invention include fragments that participate in interactions with substrates or other proteins, e.g., fragments with high surface probability scores.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FRET) (see, for example, Lakowicz et al., U.S. Pat. No. 5,631,169; Stavrianopoulos et al., U.S. Pat. No. 4,968,103; each of which is herein incorporated by reference). A fluorophore label is selected such that a first donor molecule's emitted fluorescent energy will be absorbed by a fluorescent label on a second, 'acceptor' molecule, which in turn is able to fluoresce due to the absorbed energy.

Alternately, the 'donor' protein molecule can simply utilize the natural fluorescent energy of tryptophan residues. Labels are chosen that emit different wavelengths of light, such that the 'acceptor' molecule label can be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in 1 5 the assay should be maximal. An FRET binding event can be conveniently measured through standard fluorometric detection means well known in the art (e.g., using a fluorimeter).

In another embodiment, determining the ability of the stem cell cancer markers protein to bind to a target molecule can be accomplished using real-time Biomolecular Interaction Analysis (BIA) (see, e.g., Sjolander and Urbaniczky, Anal. Chem. 63:2338-2345 [1991] and Szabo et al. Curr. Opin. Struct. Biol. 5:699-705 [1995]). "Surface plasmon resonance" or "BIA" detects biospecific interactions in real time, without labeling any of the interactants (e.g., B1Acore). Changes in the mass at the binding surface (indicative of a binding event) result in alterations of the refractive index of light near the surface (the optical phenomenon of surface plasmon resonance (SPR)), resulting in a detectable signal that can be used as an indication of real-time reactions between biological molecules.

In one embodiment, the target gene product or the test substance is anchored onto a solid phase. The target gene product/test compound complexes anchored on the solid phase can be detected at the end of the reaction. The target gene product can be anchored onto a solid surface, and the test compound, (which is not anchored), can be labeled, either directly or indirectly, with detectable labels discussed herein.

It may be desirable to immobilize stem cell cancer markers, an anti-cancer marker antibody or its target molecule to facilitate separation of complexed from non-complexed forms of one or both of the proteins, as well as to accommodate automation of the assay. Binding of a test compound to a stem cell cancer marker protein, or interaction of a cancer marker protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase-cancer marker fusion proteins or glutathione-S-transferase/target fusion proteins can be adsorbed onto glutathione Sepharose beads (Sigma Chemical, St. Louis, Mo.) or glutathione-derivatized microtiter plates, which are then combined with the test compound or the test compound and either the non-adsorbed target protein or cancer marker protein, and the mixture incubated under conditions conducive for complex formation (e.g., at physiological conditions for salt and pH). Following incubation, the beads or microtiter plate wells are washed to remove any unbound components, the matrix immobilized in the case of beads, complex determined either directly or indirectly, for example, as described above.

Alternatively, the complexes can be dissociated from the matrix, and the level of cancer markers binding or activity determined using standard techniques. Other techniques for immobilizing either cancer markers protein or a target molecule on matrices include using conjugation of biotin and streptavidin. Biotinylated cancer marker protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-IgG antibody).

This assay is performed utilizing antibodies reactive with stem cell cancer marker protein or target molecules but which do not interfere with binding of the stem cell cancer markers protein to its target molecule. Such antibodies can be derivatized to the wells of the plate, and unbound target or cancer markers protein trapped in the wells by antibody conjugation. Methods for detecting such complexes, in addition to those described above for the GST-immobilized complexes, include immunodetection of complexes using antibodies reactive with the cancer marker protein or target molecule, as well as enzyme-linked assays which rely on detecting an enzymatic activity associated with the cancer marker protein or target molecule.

Alternatively, cell free assays can be conducted in a liquid phase. In such an assay, the reaction products are separated from unreacted components, by any of a number of standard techniques, including, but not limited to: differential centrifugation (see, for example, Rivas and Minton, Trends Biochem Sci 18:284-7 [1993]); chromatography (gel filtration chromatography, ion-exchange chromatography); electrophoresis (see, e.g., Ausubel et al., eds. Current Protocols in Molecular Biology 1999, J. Wiley: New York.); and immunoprecipitation (see, for example, Ausubel et al., eds. Current Protocols in Molecular Biology 1999, J. Wiley: New York). Such resins and chromatographic techniques are known to one skilled in the art (See e.g., Heegaard J. Mol. Recognit. 11:141-8 [1998]; Hageand Tweed J. Chromatogr. Biomed. Sci. Appl 699:499-525 [1997]). Further, fluorescence energy transfer can also be conveniently utilized, as described herein, to detect binding without further purification of the complex from solution.

The assay can include contacting the stem cell cancer markers protein or biologically active portion thereof with a known compound that binds the cancer marker to form an assay mixture, contacting the assay mixture with a test compound, and determining the ability of the test compound to interact with a cancer marker protein, wherein determining the ability of the test compound to interact with a cancer marker protein includes determining the ability of the test compound to preferentially bind to cancer markers or biologically active portion thereof, or to modulate the activity of a target molecule, as compared to the known compound.

To the extent that stem cell cancer markers can, in vivo, interact with one or more cellular or extracellular macromolecules, such as proteins, inhibitors of such an interaction are useful. A homogeneous assay can be used can be used to identify inhibitors.

For example, a preformed complex of the target gene product and the interactive cellular or extracellular binding partner product is prepared such that either the target gene products or their binding partners are labeled, but the signal generated by the label is quenched due to complex formation (see, e.g., U.S. Pat. No. 4,109,496, herein incorporated by reference, that utilizes this approach for immunoassays). The addition of a test substance that competes with and displaces one of the species from the preformed complex will result in the generation of a signal above background. In this way, test substances that disrupt target gene product-binding partner interaction can be identified. Alternatively, cancer markers protein can be used as a "bait protein" in a two-hybrid assay or three-hybrid assay (see, e.g., U.S. Pat. No. 5,283,317; Zervos et al., Cell 72:223-232 [1993]; Madura et al., J. Biol. Chem. 268.12046-12054 [1993]; Bartel et al., Biotechniques 14:920-924 [1993]; Iwabuchi et al., Oncogene 8:1693-1696 [1993]; and Brent WO 94/10300; each of which is herein incorporated by reference), to identify other proteins, that bind to or interact with cancer markers ("cancer marker-binding proteins" or "cancer marker-bp") and are involved in cancer marker activity. Such cancer marker-bps can be activators or inhibitors of signals by the cancer marker proteins or targets as, for example, downstream elements of a cancer markers-mediated signaling pathway.

Modulators of cancer markers expression can also be identified. For example, a cell or cell free mixture is contacted with a candidate compound and the expression of cancer marker mRNA or protein evaluated relative to the level of expression of stem cell cancer marker mRNA or protein in the absence of the candidate compound. When expression of cancer marker mRNA or protein is greater in the presence of the candidate compound than in its absence, the candidate compound is identified as a stimulator of cancer marker mRNA or protein expression. Alternatively, when expression of cancer marker mRNA or protein is less (i.e., statistically significantly less) in the presence of the candidate compound than in its absence, the candidate compound is identified as an inhibitor of cancer marker mRNA or protein expression. The level of cancer markers mRNA or protein expression can be determined by methods described herein for detecting cancer markers mRNA or protein.

A modulating agent can be identified using a cell-based or a cell free assay, and the ability of the agent to modulate the activity of a cancer markers protein can be confirmed in vivo, e.g., in an animal such as an animal model for a disease (e.g., an animal with prostate cancer or metastatic prostate cancer; or an animal harboring a xenograft of a prostate cancer from an animal (e.g., human) or cells from a cancer resulting from metastasis of a prostate cancer (e.g., to a lymph node, bone, or liver), or cells from a prostate cancer cell line.

This invention further pertains to novel agents identified by the above-described screening assays (See e.g., below description of cancer therapies). Accordingly, it is within the scope of this invention to further use an agent identified as described herein (e.g., a cancer marker modulating agent, an antisense cancer marker nucleic acid molecule, a siRNA molecule, a cancer marker specific antibody, or a cancer marker-binding partner) in an appropriate animal model (such as those described herein) to determine the efficacy, toxicity, side effects, or mechanism of action, of treatment with such an agent. Furthermore, novel agents identified by the above-described screening assays can be, e.g., used for treatments as described herein (e.g. to treat a human patient who has cancer).

Cancer Therapies

In some embodiments, the present invention provides therapies for cancer (e.g., breast cancer). In some embodiments, therapies target cancer markers (e.g., including but not limited to, those shown in Tables 4-9).

Antibody Therapy

In some embodiments, the present invention provides antibodies that target tumors that express a stem cell cancer marker of the present invention (e.g., those shown in Tables 4-9). Any suitable antibody (e.g., monoclonal, polyclonal, or synthetic) can be utilized in the therapeutic methods disclosed herein. In some embodiments, the antibodies used for cancer therapy are humanized antibodies. Methods for humanizing antibodies are well known in the art (See e.g., U.S. Pat. Nos. 6,180,370, 5,585,089, 6,054,297, and 5,565,332; each of which is herein incorporated by reference).

In some embodiments, the therapeutic antibodies comprise an antibody generated against a stem cell cancer marker of the present invention, wherein the antibody is conjugated to a cytotoxic agent. In such embodiments, a tumor specific therapeutic agent is generated that does not target normal cells, thus reducing many of the detrimental side effects of traditional chemotherapy. For certain applications, it is envisioned that the therapeutic agents will be pharmacologic agents that will serve as useful agents for attachment to antibodies, particularly cytotoxic or otherwise anticellular agents having the ability to kill or suppress the growth or cell division of endothelial cells. The present invention contemplates the use of any pharmacologic agent that can be conjugated to an antibody, and delivered in active form. Exemplary anticellular agents include chemotherapeutic agents, radioisotopes, and cytotoxins. The therapeutic antibodies of the present invention can include a variety of cytotoxic moieties, including but not limited to, radioactive isotopes (e.g., iodine-131, iodine-123, technicium-99m, indium-111, rhenium-188, rhenium-186, gallium-67, copper-67, yttrium-90, iodine-125 or astatine-211), hormones such as a steroid, antimetabolites such as cytosines (e.g., arabinoside, fluorouracil, methotrexate or aminopterin; an anthracycline; mitomycin C), vinca alkaloids (e.g., demecolcine; etoposide; mithramycin), and antitumor alkylating agent such as chlorambucil or melphalan. Other embodiments can include agents such as a coagulant, a cytokine, growth factor, bacterial endotoxin or the lipid A moiety of bacterial endotoxin. For example, in some embodiments, therapeutic agents will include plant-, fungus- or bacteria-derived toxin, such as an A chain toxins, a ribosome inactivating protein, α-sarcin, aspergillin, restrictocin, a ribonuclease, diphtheria toxin or pseudomonas exotoxin, to mention just a few examples. In some embodiments, deglycosylated ricin A chain is utilized.

In any event, it is proposed that agents such as these can, if desired, be successfully conjugated to an antibody, in a manner that will allow their targeting, internalization, release or presentation to blood components at the site of the targeted tumor cells as required using known conjugation technology (See, e.g., Ghose et al., Methods Enzymol., 93:280 [1983]).

For example, in some embodiments the present invention provides immunotoxins targeted a stem cell cancer marker of the present invention. Immunotoxins are conjugates of a specific targeting agent typically a tumor-directed antibody or fragment, with a cytotoxic agent, such as a toxin moiety. The targeting agent directs the toxin to, and thereby selectively kills, cells carrying the targeted antigen. In some embodiments, therapeutic antibodies employ crosslinkers that provide high in vivo stability (Thorpe et al., Cancer Res., 48:6396 [1988]).

In other embodiments, particularly those involving treatment of solid tumors, antibodies are designed to have a cytotoxic or otherwise anticellular effect against the tumor vasculature, by suppressing the growth or cell division of the vascular endothelial cells. This attack is intended to lead to a tumor-localized vascular collapse, depriving the tumor cells, particularly those tumor cells distal of the vasculature, of oxygen and nutrients, ultimately leading to cell death and tumor necrosis.

In some embodiments, antibody based therapeutics are formulated as pharmaceutical compositions as described below. In some embodiments, administration of an antibody composition of the present invention results in a measurable decrease in cancer (e.g., decrease or elimination of tumor).

Pharmaceutical Compositions

The present invention further provides pharmaceutical compositions (e.g., comprising a small molecule, antisense, antibody, or siRNA that targets the stem cell cancer markers of the present invention). The pharmaceutical compositions of the present invention can be administered in a number of ways depending upon whether local or systemic treatment is desired and upon the area to be treated. Administration can be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like can be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders can be desirable.

Compositions and formulations for parenteral, intrathecal or intraventricular administration can include sterile aqueous solutions that can also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions can be generated from a variety of components that include, but are not limited to, preformed liquids, self-emulsifying solids and self-emulsifying semisolids.

The pharmaceutical formulations of the present invention, which can conveniently be presented in unit dosage form, can be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention can be formulated into any of many possible dosage forms such as, but not limited to, tablets, capsules, liquid syrups, soft gels, suppositories, and enemas. The compositions of the present invention can also be formulated as suspensions in aqueous, non-aqueous or mixed media. Aqueous suspensions can further contain substances that increase the viscosity of the suspension including, for example, sodium carboxymethylcellulose, sorbitol and/or dextran. The suspension can also contain stabilizers.

In one embodiment of the present invention the pharmaceutical compositions can be formulated and used as foams. Pharmaceutical foams include formulations such as, but not limited to, emulsions, microemulsions, creams, jellies and liposomes. While basically similar in nature these formulations vary in the components and the consistency of the final product.

Agents that enhance uptake of oligonucleotides at the cellular level can also be added to the pharmaceutical and other compositions of the present invention. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present invention can additionally contain other adjunct components conventionally found in pharmaceutical compositions. Thus, for example, the compositions can contain additional, compatible, pharmaceutically-active materials such as, for example, antipruritics, astringents, local anesthetics or anti-inflammatory agents, or can contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Certain embodiments of the invention provide pharmaceutical compositions containing (a) one or more compounds that modulate the activity of a stem cell caner marker (e.g. antibody, small molecule, siRNA, anti-sense, etc.) and (b) one or more other chemotherapeutic agents. Examples of such chemotherapeutic agents include, but are not limited to, anticancer drugs such as daunorubicin, dactinomycin, doxorubicin, bleomycin, mitomycin, nitrogen mustard, chlorambucil, melphalan, cyclophosphamide, 6-mercaptopurine, 6-thioguanine, cytarabine (CA), 5-fluorouracil (5-FU), floxuridine (5-FUdR), methotrexate (MTX), colchicine, vincristine, vinblastine, etoposide, teniposide, cisplatin and diethylstilbestrol (DES). Anti-inflammatory drugs, including but not limited to nonsteroidal anti-inflammatory drugs and corticosteroids, and antiviral drugs, including but not limited to ribivirin, vidarabine, acyclovir and ganciclovir, can also be combined in compositions of the invention. Other chemotherapeutic agents are also within the scope of this invention. Two or more combined compounds can be used together or sequentially.

Dosing is dependent on severity and responsiveness of the disease state to be treated, with the course of treatment lasting from several days to several months, or until a cure is effected or a diminution of the disease state is achieved (e.g. reduction in tumor size). Optimal dosing schedules can be calculated from measurements of drug accumulation in the body of the patient. The administering physician can easily determine optimum dosages, dosing methodologies and repetition rates. Optimum dosages can vary depending on the relative potency of individual oligonucleotides, and can generally be estimated based on $EC_{50}$s found to be effective in vitro and in vivo animal models or based on the examples described herein. In general, dosage is from 0.01 µg to 100 g per kg of body weight, and can be given once or more daily, weekly, monthly or yearly. The treating physician can estimate repetition rates for dosing based on measured residence times and concentrations of the drug in bodily fluids or tissues. Following successful treatment, it can be desirable to have the subject undergo maintenance therapy to prevent the recurrence of the disease state, wherein the oligonucleotide is administered in maintenance doses, ranging from 0.01 µg to 100 g per kg of body weight, once or more daily, to once every 20 years.

Transgenic Animals Expressing Cancer Marker Genes

The present invention contemplates the generation of transgenic animals comprising an exogenous cancer marker gene of the present invention or mutants and variants thereof (e.g., truncations or single nucleotide polymorphisms) or knock-outs thereof. In some embodiments, the transgenic animal displays an altered phenotype (e.g., increased or decreased presence of markers) as compared to wild-type animals. Methods for analyzing the presence or absence of such phenotypes include but are not limited to, those disclosed herein. In some embodiments, the transgenic animals further display an increased or decreased growth of tumors or evidence of cancer.

The transgenic animals of the present invention find use in drug (e.g., cancer therapy) screens. In some embodiments, test compounds (e.g., a drug that is suspected of being useful to treat cancer) and control compounds (e.g., a placebo) are administered to the transgenic animals and the control animals and the effects evaluated.

The transgenic animals can be generated via a variety of methods. In some embodiments, embryonal cells at various developmental stages are used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter that allows reproducible injection of 1-2 picoliters (pl) of DNA solution. The use of zygotes as a target for gene transfer has a major advantage in that in most cases the injected DNA will be incorporated into the host genome before the first cleavage (Brinster et al., 1985, PNAS 82:4438-4442). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873,191 describes a method for the micro-injection of zygotes; the disclosure of this patent is incorporated herein in its entirety.

In other embodiments, retroviral infection is used to introduce transgenes into a non-human animal. In some embodiments, the retroviral vector is utilized to transfect oocytes by injecting the retroviral vector into the perivitelline space of the oocyte (U.S. Pat. No. 6,080,912, incorporated herein by reference). In other embodiments, the developing non-human embryo can be cultured in vitro to the blastocyst stage. During this time, the blastomeres can be targets for retroviral infection (Janenich, 1976, PNAS 73:1260). Efficient infection of the blastomeres is obtained by enzymatic treatment to remove the zona pellucida (Hogan et al., in *Manipulating the Mouse Embryo*, Cold Spring Harbor Laboratory Press, Cold Spring Harbor, N.Y. [1986]). The viral vector system used to introduce the transgene is typically a replication-defective retrovirus carrying the transgene (Jahner et al., 1985, PNAS 82:6927). Transfection is easily and efficiently obtained by culturing the blastomeres on a monolayer of virus-producing cells (Stewart, et al., 1987, EMBO J., 6:383).

Alternatively, infection can be performed at a later stage. Virus or virus-producing cells can be injected into the blastocoele (Jahner et al., 1982, Nature 298:623). Most of the founders will be mosaic for the transgene since incorporation occurs only in a subset of cells that form the transgenic animal. Further, the founder can contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jahner et al., supra [1982]). Additional means of using retroviruses or retroviral vectors to create transgenic animals known to the art involve the micro-injection of retroviral particles or mitomycin C-treated cells producing retrovirus into the perivitelline space of fertilized eggs or early embryos (PCT International Application WO 90/08832 [1990], and Haskell and Bowen, 1995, Mol. Reprod. Dev., 40:386).

In other embodiments, the transgene is introduced into embryonic stem cells and the transfected stem cells are utilized to form an embryo. ES cells are obtained by culturing pre-implantation embryos in vitro under appropriate conditions (Evans et al., 1981, Nature 292:154; Bradley et al., 1984, Nature 309:255; Gossler et al., 1986, PNAS 83:9065; and Robertson et al., 1986, Nature 322:445). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes can also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science, 1988, 240:1468). Prior to the introduction of transfected ES cells into the blastocoel, the transfected ES cells can be subjected to various selection protocols to enrich for ES cells which have integrated the transgene assuming that the transgene provides a means for such selection. Alternatively, the polymerase chain reaction can be used to screen for ES cells that have integrated the transgene. This technique obviates the need for growth of the transfected ES cells under appropriate selective conditions prior to transfer into the blastocoel.

In still other embodiments, homologous recombination is utilized to knock-out gene function or create deletion mutants (e.g., truncation mutants). Methods for homologous recombination are described in U.S. Pat. No. 5,614,396, incorporated herein by reference.

EXPERIMENTAL

The following examples are provided in order to demonstrate and further illustrate certain embodiments and aspects of the present invention and are not to be construed as limiting the scope thereof.

In the experimental disclosure which follows, the following abbreviations apply: N (normal); M (molar); mM (millimolar); μM (micromolar); mol (moles); mmol (millimoles); μmol (micromoles); nmol (nanomoles); pmol (picomoles); g (grams); mg (milligrams); μg (micrograms); ng (nanograms); l or L (liters); ml (milliliters); μl (microliters); cm (centimeters); mm (millimeters); μm (micrometers); nm (nanometers); ° C. (degrees Centigrade); i.p. (intraperitoneal); HBSS (Hepes buffered saline solution); FCS (fetal calf serum); FBS (fetal bovine serum).

Example 1

Isolation of Colon Cancer Stem Cells

Recently it has been demonstrated that malignant human breast tumors harbor a small, distinct population of cancer stem cells that are enriched for the ability to form tumors in immunodeficient mice. An ESA+, CD44+, CD24−/low, Lin− cell population was found to be 50-fold enriched for tumorigenic breast tumor cells compared to unfractionated tumor cells (Al-Hajj et al., 2003, PNAS 100:3983-8). This example describes the identification of a cancer stem cell population in colorectal cancers.

To identify colon cancer stem cells, a tumor sample from a patient biopsy of a colorectal carcinoma minimally passaged in immunocompromised mice was examined. Tumor cells were removed under sterile conditions, cut into small pieces, and minced completely using sterile blades. Single cell suspensions were then obtained by enzymatic digestion and mechanical disruption. Specifically, minced tumor pieces were mixed with Collagenase/Hyaluronidase, supplemented with Dispase, in culture medium and incubated at 37° C. for 2 hours with pipetting up and down through a 10-mL pipette every 15-20 min. Digested cells were filtered through a 40 uM nylon mesh, washed with RPMI/10% FBS, and washed twice with HBSS/2% FBS and 25 mM HEPES.

Single cell tumor suspensions were next sorted into tumorigenic and non-tumorigenic cells based on cell surface markers. Cells were counted, washed twice with HBSS containing 2% heat-inactivated calf serum (HICS) and 25 mM HEPES, and resuspended at $10^6$ cells per 100 ul. Tumor cells were incubated with rat anti-mouse $H2K^d$, CD3, CD4, CD8, Ter119, Mac1 and Gr1 antibodies conjugated to magnetic beads and, applied to a strong magnet to remove mouse hematopoietic and stromal cells. In certain embodiments, bulk tumor cells can be depleted of murine cells using biotin-conjugated anti-H2 $K^d$ and murine CD45, followed by conjugation to strepavidin-conjugated magnetic beads and application to a strong magnet. Tumors cells were then incubated with either sheep anti-rat or Strepatividin antibodies conjugated to Cy5.5-PE and the viability dye propidium iodide (PI) to detect and enable exclusion of remaining mouse hematopoietic/stromal cells and dead cells, respectively. Cells were further incubated with fluorescently conjugated antibodies against human ESA (Miltenyi Biotec; Auburn, Calif.) and CD44, (Bioscience, San Diego, Calif.) to positively select human tumor cells expressing ESA and CD44. Flow cytometry was performed on a FACSAria (Becton Dickinson, Franklin Lakes, N.J.) with the use of side and forward scatter profiles to exclude doublets and cell clumps. Cy5.5-PE+ and PI positive cells were first excluded and a fraction of ESA+ 44+ cells was isolated independently of a fraction of non-ESA+44+ tumor cells (FIG. 1).

The tumorigenicity of isolated ESA+44+ colon tumor cells compared to non-ESA+, CD44+ colon tumor cells was next determined. Isolated ESA+44+ tumor cells versus non-ESA+ 44+ tumor cells at approximately 1,000 cells per animal were injected subcutaneously into NOD/SCID mice. Tumors were allowed to grow and tumor volumes were assessed weekly. Only mice injected with ESA+44+ cells developed tumors (FIG. 2), demonstrating a dramatic enrichment for tumorigenic cancer stem cells. Tumors were consistently obtained upon injection of as few as 100 ESA+CD44+ cells (FIG. 2B & Table 2).

TABLE 2

| | Tumors/Injections | | | | | | |
|---|---|---|---|---|---|---|---|
| | 2000 | 1000 | 500 | 250 | 200 | 100 | 40 |
| UM-C4 | | | | | | | |
| ESA+CD44+ | 5/5 | 11/12 | 17/20 | — | 29/33 | 10/10 | 11/32 |
| ESA+CD44− | 0/20 | 2/24 | 0/4 | — | 0/20 | — | — |
| ESA+CD44+ALDH+ | — | — | 5/5 | 5/7 | — | — | — |
| ESA+CD44+ALDH− | — | — | 0/5 | 0/6 | — | — | — |
| ESA+CD44−ALDH+ | — | — | 0/5 | 0/6 | — | — | — |
| UM-C6 | | | | | | | |
| ESA+CD44+ | 4/4 | 5/5 | 10/10 | — | 7/11 | — | — |
| ESA+CD44− | 0/10 | 0/10 | — | — | 0/4 | — | — |
| ESA+CD44+ALDH+ | — | — | 3/13 | 2/9 | — | — | — |
| ESA+CD44+ALDH− | — | — | 2/2 | 2/8 | — | — | — |
| ESA+CD44−ALDH+ | — | — | 0/10 | 0/7 | — | — | — |
| OMP-C5 | | | | | | | |
| ESA+CD44+ | 4/5 | — | 7/10 | — | — | — | — |
| ESA+CD44− | 0/10 | — | — | — | — | — | — |
| ESA+ALDH+ | — | — | 3/9 | — | — | — | — |
| ESA+ALDH− | — | — | 1/11 | — | — | — | — |
| OMP-C8 | | | | | | | |
| ESA+CD44+ | 5/5 | 4/4 | 5/10 | — | — | — | 2/10 |
| ESA+CD44− | 1/15 | — | — | — | — | — | — |
| ESA+CD44+ALDH+ | — | — | 5/11 | — | — | — | — |
| ESA+CD44+ALDH− | — | — | 6/13 | — | — | — | — |
| ESA+CD44−ALDH+ | — | — | 0/2 | — | — | — | — |

Following tumor growth out to over 80 days revealed continuing growth of tumors generated by ESA+44+ tumor cells, but only rarely (3/89) were tumors formed in mice injected with ESA+, CD44− or ESA−CD44− tumor cells at doses of 1000 or more (FIG. 2 and Table 2). These rare tumors from NTG cells, observed only at higher cell doses, likely result from cell sorting impurities (~0.5%). Importantly, the tumors generated by the ESA+CD44+ colon cancer stem cells were phenotypically similar to the tumors from which the colon cancer stem cells were isolated (FIG. 3).

Example 2

Identification of Colon Cancer Stem Cell Markers by Microarray Analysis

Following the successful isolation of colon cancer stem cells, microarray analysis was utilized to identify markers for colon cancer stem cells versus non-tumorigenic tumor cells. Presorted tumor cells, tumorigenic cancer stem cells, and sorted non-tumorigenic solid tumor cells were isolated and separated by FACS as described above in duplicate. Total RNA was isolated from the different cell populations using RNeasy (Qiagen, Valencia, Calif.) according to the manufacturer's protocol. Probes for microarray analysis were prepared and hybridized to Affymetrix HG-U133 gene chips according to Affymetrix protocols (Affymetrix, Santa Clara, Calif.). Arrays were scanned with an argon-ion laser confocal microscope and the intensity for each probe set on the array was assessed with Affymetrix Microarray Suite 4.0 software according to Affymetrix procedures.

Genes identified by microarray analysis as having increased expression in colon cancer stem cells compared with non-tumorigenic tumor cells (FIG. 4A), both of which populations were isolated by FACS, are listed in Table 1. These genes serve as a gene expression profile of colon cancer stem cells and find use in markers of colon cancer stem cells. Included in this list is the Notch pathway target genes HES1 and HES6. HES6, in particular, was found to be expressed in isolated tumorigenic colon stem cells at 6-fold higher levels than in FACS sorted non-tumorigenic tumor cells (FIG. 5A). This suggests that activation of the Notch pathway is important to the biological function of colon cancer stem cells and highlights Hes6 and/or HES1 as a unique marker of Notch activation in this rare cell population.

To validate microarray data, RNA was independently isolated from FACS-purified colon cancer stem cells and non-tumorigenic cells and relative gene expression was assessed using Taqman assay quantitative RT-PCR. Using purified cell populations from UM-C4 colon cancer cells, for example, HES1 was shown to be increased in TG versus NTG cells (FIG. 5B). An additional subset of colon cancer stem cell genes was also assessed in this manner, demonstrating that whereas ATOH1, BMPR1A, CDH1, EPHB2, MYB, MYC, SOX9 and STRAP were verified to be increased in TG versus NTG cells, TCF4 and VIM were consistently lower in colon cancer stem cells versus NTG cells (FIG. 4B).

Example 3

Analysis of HES6 Expression by Colon Cancer Stem Cells

The identification of HES6 expression as upregulated in tumorigenic ESA+44+ colon tumor cells compared to non-tumorigenic colon tumor cells enables the use of HES6 to enrich further for colon cancer stem cells. To examine HES6 expression by ESA+44+ tumorigenic colon stem cells, the HES6 promoter is used to control expression of the marker protein GFP in colon tumor cells and cells are sorted based on cell surface expression of ESA and CD44 as well as GFP expression.

To generate a HES6 regulated GFP reporter construct, the endogenous HES6 promoter is isolated from genomic human DNA and ligated 5' to a GFP expression cassette and then incorporated into the ViraPower™ Lentiviral Expression System (Invitrogen, Carlsbad, Calif.) using standard recombinant DNA techniques. Viral particles are generated according to the manufacturer's protocol and used to infect colon tumor stem cells isolated as described in detail above. Infected tumor stem cells are repassaged into immunocompromised mice to grow tumors that can then be analyzed for ESA, CD44, and GFP expression.

Tumors generated by HES6-GFP infected colon cancer stem cells are isolated and single cell suspensions generated as described above. Single cell tumor suspensions are then sorted into tumorigenic and non-tumorigenic cells based on the cell surface markers ESA and CD44 as described above and further sorted for GFP expression to determine the percentage of ESA+44+ colon cancer stem cells that express HES6 as indicated by GFP+ cells.

If the ESA+44+ cancer stem cell populations contains both GFP− and GFP+ cell populations, the tumorigenicity of these different cell populations will be determined. Specifically, isolated ESA+44+GFP+ versus ESA+44+GFP− cells are injected subcutaneously NOD/SCID mice at approximately 1,000; 500; and 250 cells per animal. Differences in the number of injected cells required for consistent tumor formation in mice will determine if selecting for expression of GFP driven by the HES6 promoter further enriches for tumorigenic tumor cells.

Example 4

HES6-GFP Based Assays to Analyze the Effects of Therapeutic Compounds on Colon Cancer Stem Cells Successful use of the HES6 promoter to drive expression of GFP in colon cancer stem cells enables the use of HES6-GFP based assays to examine the effects of potential therapeutic compounds on the properties of colon cancer stem cells. Colon cancer stem cells can be easily detected based on GFP expression and increases or decreases in the numbers of GFP+ colon cancer stem cells determined following treatment with a potential therapeutic compound.

Colon cancer stem cells are isolated and infected with HES-GFP lentivirus as described in detail above and injected subcutaneously into immunodeficient mice. Animals are then either immediately treated with the potential therapeutic compound such as, for example, an antibody against a colon cancer stem cell marker, or palpable tumors are allowed to grow and treatment with the compound is then initiated. Thus, for example, naked anti-PTGFRN antibodies or control antibodies are injected i.p. twice a week for six weeks. Following antibody treatment, tumors are harvested and dissociated into single cell suspension as described above, and FACS analysis performed to detect GFP+ colon cancer stem cells. The presence and number of colon cancer stem cells in tumors from animals treated with anti-PTGFRN antibodies versus control antibodies is thus determined.

Example 5

HES6-Luciferase Reporter Assays

The endogenous HES6 promoter contains three cbf transcriptional binding domains indicating that like HES1, with a promoter that contains a single cbf binding domain, HES6 expression is directly regulated by activation of the Notch signaling pathway. Identification of HES6 as a colon cancer stem cell marker enables the use of the HES6 promoter as a reporter for Notch activation in, for example, luciferase based reporter assays to characterize the Notch pathway activation of HES6 and to measure the effect of compounds on activating or inhibiting the Notch signaling pathway.

To generate Notch luciferase reporters, the endogenous HES6 promoter is isolated from genomic human DNA and ligated 5' to a firefly luciferase expression cassette in an expression plasmid vector using standard recombinant techniques. In addition the HES6 promoter luciferase polynucleotide is incorporated into the ViraPower™ Lentiviral Expression System (Invitrogen, Carlsbad, Calif.) and viral particles generated according to the manufacturer's protocol. As a control, mutant HES6-luciferase reporter vectors are generated that contain mutations within the three cbf transcription binding domains that disrupt RBP-J binding to the HES6 promoter.

In one embodiment of the invention, an in vitro luciferase assay is used to characterize the Notch pathway activation of HES6 by determining which of the four Notch receptors are involved in HES6 expression. HEK293 cells cultured in DMEM supplemented with antibiotics and 10% FCS are co-transfected with: 1) the wild-type or mutant HES6-luciferase reporter vector to measure levels of Notch signaling; 2) a *Renilla luciferase* reporter (Promega; Madison, Wis.) as an internal control for transfection efficiency; and 3) an expression vector encoding one of the four Notch receptors or a negative control. Forty-eight hours following transfection, luciferase levels are measured using a dual luciferase assay kit (Promega; Madison, Wis.) with firefly luciferase activity normalized to *Renilla luciferase* activity. Levels of enhanced Notch signaling over endogenous levels by heterologous expression of each of the Notch receptors will help determine which of these receptors is involved in HES6 activation in colon cancer stem cells.

In another embodiment of the invention, an in vitro luciferase assay is used to determine the effect of different molecules on Notch signaling. HEK293 cells cultured in DMEM supplemented with antibiotics and 10% FCS are co-transfected with: 1) the wild-type or mutant HES6-luciferase reporter vector to measure levels of Notch signaling and 2) a *Renilla luciferase* reporter (Promega; Madison, Wis.) as an internal control for transfection efficiency. Furthermore, an expression vector encoding a Notch receptor is transfected to boost endogenous Notch signaling in the cultured cells. Twenty-four hours following transfection, the molecule being tested for an effect on Notch signaling such as, for example, an antibody against a Notch receptor, or a negative control molecule are added to the cell culture medium, and after eight hours, luciferase levels are measured using a dual luciferase assay kit (Promega; Madison, Wis.). Three independent experiments are performed in triplicate. The ability of different compounds to activate or inhibit the Notch signaling pathway in vitro is thus determined.

In yet another embodiment, compounds that inhibit the Notch signaling pathway the in vitro assay are used in an in vivo luciferase assay to determine the effect on colon cancer stem cells. Colon cancer stem cells isolated as described above are infected with wild-type or mutant HES6-luciferase lentiviruses, and the infected tumor cells injected into the mammary fat pads of VP-16 and estrogen pre-treated immunodeficient mice. Animals are then either immediately treated with the Notch inhibitory molecule such as, for example, an antibody against a Notch receptor, or palpable tumors are allowed to grow and then treatment of the inhibitory compound is initiated. Primary tumor growth and distal metastases are then monitored over time for luciferase activity in live mice using bioluminescent imaging. The ability of different compound that inhibit Notch signaling to stop or slow cancer stem cell proliferation and metastasis in vivo is thus determined.

Example 6

Quantitative RT-PCR Assays Using HES6 to Detect the Number of Colon Cancer Stem Cells in a Tumor Sample The identification of HES6 as a marker of colon cancer stem cells enables its use in determining the number of cancer stem cells present in a tumor sample by TaqMan analysis. Such an analysis could be undertaken to examine, for example, the effect of experimental compounds on cancer stem cell proliferation or survival. Also contemplated is the analysis of a patient tumor sample in order to diagnosis a tumor and/or provide a prognosis.

TaqMan oligonucleotide primers and probes that specifically hybridize to and amplify a region of HES6 mRNA over an exon-intron junction are designed using Primer Express Software (Applied Biosystems; Foster City, Calif.) and their specificity confirmed using conventional RT-PCR techniques. Colon cancer stem cell are isolated as described above and total RNA extracted using RNasy (Qiagen, Valencia, Calif.) according to the manufacturer's protocol. Using Applied Biosystems 7300 Real-Time PCR System and TaqMan One-Step RT-PCR Master Mix Reagents Kit a standard curve of the average amount of HES6 mRNA expressed in a microgram of RNA from a known number of colon cancer stem cells is determined. Serial 10-fold dilutions of RNA from isolated colon cancer stem cells with RNA from a cell population that does not express detectable levels of HES6 are used to generate the standard curve. Expression levels are normalized to the housekeeping gene GAPDH. Colon cancer samples with an unknown number of cancer stem cells can be compared to a simultaneously generated standard curve to determine the number of cancer stem cells in the sample.

In one embodiment of the present invention, TaqMan analysis can be used to examine the effect of a compound on the proliferation and survival of colon cancer stem cells. Colon cancer stem cells isolated as described above are injected subcutaneously into NOD/SCID mice. Tumor cells are allowed to grow into palpable tumors at which point animals are treated with a potential therapeutic compound such as, for example, an antibody against colon cancer stem cell marker disclosed in Table 1. Thus, for example, naked anti-MET receptor antibodies or control antibodies are injected i.p. twice a week for two to three weeks. Tumors are then harvested from MET antibody and control injected mice and total RNA isolated from tumors using RNasy (Qiagen, Valencia, Calif.) according to the manufacturer's protocol. The number of HES6 positive colon cancer stem cells from each tumor in the different experimental groups is then determined by TaqMan analysis compared to a standard curve of HES6 expression in colon cancer stem cells generated as described above. A decrease in the number of colon cancer stem cells in the anti-MET antibody treated group suggests that the therapeutic compound has a direct effect on the survival and/or proliferation of colon cancer stem cells.

In another embodiment of the invention, TaqMan analysis can be used to determine the number of colon cancer stem cells in a patient sample. RNA is extracted as described above from a fresh or historical tumor biopsy of a colon cancer, and the number of HES6 positive colon cancer stem cells in the sample determined by comparison with a standard curve of HES6 expression in colon cancer stem cells generated as described above. Such an analysis finds use in diagnosing a colon cancer, providing a prognosis of a colon cancer, analyzing the effects of different therapeutics on a colon cancer, and prescribing a therapeutic that targets colon cancer stem cells.

Example 7

Identification of CEACAM6 as a Marker of Colon Cancer Stem Cells

Genes identified by microarray analysis as having increased expression in colon cancer stem cells compared with non-tumorigenic sorted tumor cells are shown in Table 1. These genes serve as a gene expression profile of colon cancer stem cells and find use as markers of colon cancer stem cells. Included in this list is the immunoglobulin superfamily member adhesion molecule CEACAM6 (FIG. 6). Analysis by FACSAria of colon tumor cells as described above showed a definite shift in mean fluorescence intensity associated with addition of a monoclonal CEACAM6 antibody (Alexis Biochemicals; clone GM7G5; FIG. 7A). Furthermore, CEACAM6 was heterogeneously expressed in colon tumor cells (FIG. 7B).

Example 8

Purification of Colon Cancer Stem Cells based on Expression of CEACAM6

The identification of increased expression of CEACAM6 in colon cancer stem cells suggests its use as a marker to further purify stem cells from total tumor cell populations. To determine if CEACAM6 expression identifies a tumorigenic colon cancer stem cell population, colon cells are sorted based on expression of ESA, CD44, and CEACAM6 and the tumorigenicity of different sorted cell populations is assessed in immunodeficient mice.

Tumors are isolated and dissociated into single cell tumor suspensions as described above. These cells are next sorted as described in detail above into ESA+44+ colon cancer stem cells; ESA+44− non-tumorigenic colon tumor cells; ESA+44+CEACAM6+; and ESA+44+CEACAM6− cell populations. The tumorigenicity of these different isolated colon tumor cells is then determined by injected limiting dilutions of tumor cells into NOD/SCID mice. Tumors are allowed to grow and, starting at around day 30, tumor volumes measured.

Example 9

Identification of CD166 as a Marker of Colon Cancer Stem Cells

Genes identified by microarray analysis as having increased expression in colon cancer stem cells compared with non-tumorigenic sorted tumor cells are shown in Table 1. These genes serve as a gene expression profile of colon cancer stem cells and find use as markers of colon cancer stem cells. Included in this list is the immunoglobulin superfamily member adhesion molecule CD166. FACSAria of colon tumor cells as described above showed CD166 expression in 19.8% of colon tumor cells and greater than 92% of ESA+44+ colon cancer stem cells (FIG. 8).

Example 10

Purification of Colon Cancer Stem Cells based on Expression of CD166

The identification of increased expression of CD166 in colon cancer stem cells suggests its use as a marker to further purify stem cells from total tumor cell populations. To determine if CD166 expression identifies a tumorigenic colon cancer stem cell population, colon cells were sorted based on expression of ESA, CD44, and CD166 and the tumorigenicity was assessed in immunodeficient mice.

Tumors were isolated and dissociated into single cell tumor suspensions as described above. These cells were next sorted as described in detail above into ESA+44+166+; ESA+ 44+ 166−; ESA+44−166+; and ESA+44−166− cell populations. Two hundred cells from each isolated colon tumor cell population were injected into NOD/SCID mice.

Example 11

Colon Cancer Stem Cells Display Elevated Levels of ALDH Activity and Gene Expression To determine whether colon tumor cells contain ALDH activity, primary xenograft tumors depleted of murine cells (using antibodies against CD45 and $H2K^d$) were screened using the Aldefluor™ reagent. The majority of $CD44^+$ cells, approximately 85%, contained ALDH activity levels detectably higher than the bulk of colon tumor cells (FIG. 9A). Consistent with this observation, microarray analyses indicated that TG UM-C4, UM-C6, and OMP-C9 TG cells express several ALDH family members (e.g. ALDH1A1, ALDH1B1, ALDH2, ALDH3A2, ALDH5A1, ALDH6 μl, ALDH7A1, ALDH9A1 & ALDH18A1) at higher levels than NTG populations (FIGS. 10A & B). Following isolation of ALDH and CD44 subpopulations from UM-C4 tumors by dissociation and FACS, only the $ESA^+44^+ALDH^+$ subpopulation contained TG ability upon transplantation (FIG. 9B; Table 2). In contrast to ESA+CD44+ALDH+ cells from UM-C4 colon tumors, TG cells from other xenogeneic tumor lines (i.e. UM-C6, OMP-C5, and OMP-C8) did not co-purify with ALDH activity (FIG. 9C; Table 2), a result that may reflect heterogeneity among patients, disease stage, the TG cell of origin, and/or the repertoire of ALDH gene expression. Interestingly, the ALDH3A1 gene product may also mediate resistance to CPA, and its expression was uniquely elevated in microarray studies of UM-C4 TG versus NTG cells, but not differentially expressed in UM-C6 or UM-C9 cells (FIGS. 10A & B). To validate microarray data, RNA was independently isolated from FACS-purified colon cancer stem cells and non-tumorigenic cells, and relative gene expression was assessed using Taqman assay quantitative RT-PCR. ALDH1A1 was validated as being dramatically increased in TG versus NTG cells (FIG. 10C).

Cyclophosphamide (CPA) promotes DNA cross-linking and is a commonly used chemotherapeutic agent, against which patients frequently develop resistance. The elevated levels of ALDH and expression of a number of ALDH family member genes in TG colon tumor cells could contribute to such resistance in the very cells responsible for tumor recurrence post-treatment. To test this, the resistance of TG cells from UM-C4 tumors with high ALDH activity to CPA therapy compared to the majority of NTG tumor cells ($CD44^{neg}$ and/or $ALDH^{neg}$) was determined. Following tumor initiation with 500 $ESA^+CD44^+$ cells, tumors were allowed to reach ~400 mm³, at which point the mice were randomized to receive either 25 mg/kg CPA or vehicle twice weekly. UM-C4 tumor growth in CPA-treated mice was retarded versus mice treated with vehicle (FIG. 11A). Furthermore, $ESA^+CD44^+$ cells were more concentrated in tumors from CPA-treated versus vehicle-treated mice (FIG. 11B) and the frequency of cells with high ALDH activity was increased >70% (FIG. 11C), suggesting that TG cells were truly more refractory to therapy than NTG cells.

To determine whether the increase in $ESA^+CD44^+ALDH^+$ cells in CPA treated tumors compared to control vehicle-treated controls correlated with an increase in TG cell frequency, limiting doses of residual tumor tumor cells were transplanted into naïve NOD/SCID hosts. Specifically, to determine the frequency of cancer stem cells in CPA-treated versus vehicle-treated animals, four sets of eight to more mice received transplantation of 3-fold serial dilutions of bulk tumors cells, starting with 1,500 cells (dilutions: 1500, 500, 167 & 56 cells). Mice were monitored for tumor growth over a period of four months and scored as either positive or negative for tumor growth such that Poisson statistics could be done to assess TG cell frequency among the input population. All eight mice injected with 1,500 cells from either CPA-treated or vehicle-treated tumors developed tumors (Table 2). Input of less cells clearly revealed an increased frequency of TG cells in tumors from CPA-treated mice, as 9/9, 5/8 and 4/8 mice developed tumors with an input of 500, 167 and 56 cell, respectively; whereas 6/8, 3/8 and 2/8 mice grew tumors from serially transplanted vehicle-treated tumors. These frequencies translated into a 1:120 versus 1:315 frequency of TG cells in the bulk population of CPA-treated versus control vehicle-treated tumors, demonstrating a >2.6-fold increase in TG cells in CPA-treated tumors (FIG. 11D; p=0.024). Finally, though the inherent ability of $ESA^+CD44^+$ cells to generate tumors appeared equal among CPA-treated and vehicle-treated tumors, the data show a trend towards more aggressive tumor growth with cells sorted from CPA-treated tumors (FIG. 11E).

Example 12

Identification of Cancer Stem Cell Targets by Assessing In Vivo Tumorigenicity Cancer stem cells were maintained and expanded under in vitro culture conditions as demonstrated by injection of those tumorigenic cancer stem cells into animals after being maintained in culture up to 14 days. To determine whether BMP receptor signaling has an effect on cancer stem cell expansion or maintenance in vitro, UM-C6 colon tumors were processed, depleted of mouse lineage cells (mLin−; $H2K^d$ and murine CD45), and plated on laminin-coated coverslips with media devoid of, or containing, 100 ng/mL of BMP2 and BMP4 for 6 days. Cells were then harvested and injected subcutaneously into mice to determine tumorigenicity. Not only was tumorigenicity reduced (i.e. 83% vs 100%), but in contrast to various other agents (not discussed here), engagement of the BMP receptors in vitro significantly reduced the growth rate of subsequent tumors upon injection of these cells into mice (FIG. 12A). After more than 75 days in vivo, colon tumors derived from cells that had been exposed to BMPs were 42.9±10% (N=5; p<0.002) the size of control tumors (FIG. 12B), demonstrating a detrimental effect on tumorigenicity.

Example 13

Isolation of Head and Neck Cancer Stem Cells

Using methods successfully employed to identify cancer stem cells in breast cancer, head and neck squamous cell carcinoma (HNSCC) was studied. HNSCC contains a distinct population of cancer stem cells, with the exclusive ability to produce tumors in mice and recreate the original tumor heterogeneity. A cell surface marker that can distinguish this cell population from the other cancer cells is present in the tumor. The ability to identify cancer stem cells in HNSCC allows for the development of new treatment strategies targeted against this critical population of cancer cells.

Primary tumor implantation. Female NOD/SCID mice were injected intraperitoneally with ketamine/xylazine anesthetic at 0.02 mL/20-g (300 mg ketamine combined with 20 mg xylazine in 4 mL of PBS). The fresh tumor specimens on ice were received within an hour of extraction from the operating room in Media 199. Small pieces of tumor were chopped into 2-mm size with scissors. Then a 3-mm incision was made in the mid back region of the mice and small pieces of solid tumor were implanted in both sides of the base of the neck with a trocar. Tumors were pinched into their final position in the mouse and the incision was sealed with a liquid adhesive suture.

Tumor Digestion. Primary tumors were cut into small fragments with sterile scissors and then further minced with sterile scalpels. The pieces were then rinsed with HBSS (5 min: 1000 rpm) and placed in a solution of Media 199 and 200 u/mL Collagenase III. The mixture was incubated at 37° C. for up to 3 hours to allow complete digestion. Every 15 minutes, the solution was mixed through a 10-mL pipette to allow shearing of the tumor pieces. The digestion was arrested with the addition of Fetal Bovine Serum and then filtered through a 40-μm-nylon mesh. The suspended cells were washed twice with Hank's Balanced Salt Solution/2% Heat Inactivated Calf Serum and then stained for flow cytometry, frozen, or injected.

Single cell suspension injections. The mice were anesthetized in the same manner as the tumor implantation procedure. Up to 2 million cells were washed in HBSS/2% HICS and then suspended in 100 μL of RPMI 1640. The cells were then mixed in a 1:1 ratio with Matrigel (BD Pharmingen) solution to form a final volume of 200 μL. The mice were then injected subcutaneously at the base of the neck with the suspension and then sealed with a liquid adhesive suture.

Flow Cytometry. The single cell suspensions were washed in HBSS/2% HICS and then the cells were counted. Cells were then resuspended in 100 μL/$10^6$ cells of HBSS and incubated with 1 mg/mL of Sandoglobin for 10 minutes. The cells were then washed twice with HBSS/2% HICS, resuspended in 100 μL/$10^6$ cells of HBSS and stained with corresponding antibodies. Anti-CD44 (Pharred, PE or APC conjugated: BD Pharmingen) was added at the appropriate dilution per antibody and incubated for 20 minutes on ice. Primary tumor cells were also stained with lineage markers anti-CD2, CD3, CD10, CD16, CD18, CD31, CD64, and CD140b. Passaged tumor cells were incubated with anti-H2K$^d$ (BD Pharmingen). Stained cells were then washed 2 times with HBSS/HICS and resuspended at 0.5 mL/$10^6$ cells. 7-AAD (BD Pharmingen) was then added at the appropriate dilution to allow for the removal of non-viable cells from the sort. This suspension was then sorted with a BD FACSVantage flow cytometer. All Lineage+/mouse cells were eliminated during flow cytometry. Dead cells were removed based on positive 7-AAD staining. Forward and side scatter profiles were utilized to remove cell doublets. All cells were reanalyzed and sorted twice to ensure purity of >95%.

HNSCC specimens were obtained from primary tumors in 4 different subjects. All tumors were successfully engrafted into the NOD/SCID mouse model (Table 1). Three of the four experiments were conducted on tumor specimens after they had been implanted and passaged in the mouse. One experiment (UMHN4) was conducted on unpassaged tumor directly after it was obtained from the patient. Contaminating mouse cells were removed from specimens passaged in the mouse by eliminating H2K$^+$ cells (mouse histocompatibility class 1).

Identification of Tumorgenicity Markers. HNSCC specimens were heterogeneous with respect to the cell surface marker CD44. To assess whether CD44 could distinguish between tumorigenic and non-tumorigenic cells, flow cytometry was employed to isolate cells that were CD44 positive or negative (CD44$^+$, CD44$^-$). When greater than 4×$10^4$ CD44$^+$ Lineage$^-$ HNSCC cells were injected into the mice tumors always formed within 12-16 weeks. When 5–25×$10^3$ CD44$^+$ Lineage$^-$ HNSCC cells were injected tumors formed in five out of eleven implantations. When CD44$^-$Lineage$^-$ cells were injected in all cases no detectable tumors formed (Table 3). The one case where a tumor grew from CD44$^-$ cells occurred early in the study and likely resulted from contamination of the sample with CD44+ cells, due to inexperience with the flow cytometry gating required for cell sorting.

Antigens associated with normal cell types (lineage markers CD2, CD3, CD10, CD18, CD31, CD64 and Q140b) were not expressed on the cancer cells. These markers were used to eliminate normal leukocytes, fibroblasts endothelial, mesothelial and epithelial cells from the tumor specimens. The percentage of CD44$^+$Lineage$^-$ cells in the tumors varied from 5.52 to 16.45 (FIG. 5A-D). As few as 5×$10^3$ CD44$^+$ cells gave rise to tumors. In contrast up to 5×$10^5$ CD44$^-$ cells failed to form tumors. Even after greater than 24-32 weeks CD44$^-$ Lineage$^-$ injection sites revealed no detectable tumor growth.

The CD44$^+$Lineage$^-$ cells gave rise to tumors that contained cells that were phenotypically diverse for CD44 expression. Tumors resulting from implanted CD44$^+$ cells reproduced the original tumor heterogeneity on histologic examination (FIG. 6). Tumors grown from only CD44$^+$ cells could be resorted based on CD44 expression. CD44$^+$ Lineage cells from UMHN4 and SUHN2 were serially passaged through two rounds of tumor formation. CD44$^+$Lineage$^-$ cells from UMHN2 have been passaged through three rounds of tumor formation (FIG. 7). In each case only the CD44$^+$ cells produced tumor growth and the CD44$^-$ population of cells did not.

TABLE 3

| Sample | | 500-650K | 200-300K | 100K | 40-50K | 20-25K | 10K | 5K | 2K |
|---|---|---|---|---|---|---|---|---|---|
| UMHN1 | CD44+ | | 1/1 | | | | | | |
| | CD44- | 0/1 | | | | | | | |
| UMHN2 | CD44+ | | | | | 2/2 | 1/1 | | |
| | CD44- | | 0/2 | | | 0/1 | | | |
| UMHN3 | CD44+ | | | | | | | 3/3 | |
| | CD44- | | 0/3 | 0/3 | 0/3 | | | | |
| UMHN4 | CD44+ | | | | 1/1 | | | | |
| | CD44- | | 0/1 | | | | | | |

Example 14

Downstream Targets in Head and Neck Cancer Stem Cells

The methods used in this example provide guidance for the development of Notch-related and other anti-cancer therapies using the cancer stem cells of the invention. Array technology is used to begin to understand the molecular pathways that might be regulated by Notch-signaling induced by specific Notch ligands. Sequence verified human cDNAs from Research Genetics, provided by the University of Michigan Microarray Network, are arrayed by the Cancer and Microarray Facility. Probes are prepared from self-renewing head and neck cancer stem cells or cells from the various populations of cells found in a tumor. Probes are hybridized to the arrays and the hybridization patterns are read by the Cancer and Microarray Facility. The hybridization patterns were then analyzed to identify genes that hybridize to probe from the head and neck cancer stem cells stimulated with various Notch ligands and non-stimulated cells. Such genes can represent those that are involved in the regulation of head and neck cancer cell survival or self-renewal.

Preparation of Microarrays. Microarray Technology was Used to Analyze Gene expression of hematopoietic stem cells. This is now extended to cancer stem cells.

The University of Michigan Microarray Network currently has 32,500 sequence verified human cDNAs from Research Genetics. A "cancer" chip has been assembled in collaboration with the NCI. This chip contains a comprehensive constellation of 1,200 genes involved in proliferation and tumorigenesis. There is also an "apoptosis chip" developed by the University of Michigan that contains all genes known to be involved in programmed cell death. Note that the HES genes, known to be downstream targets of Notch, are included in the arrays.

Preparation of Probe from Head and Neck Cancer Stem Cells. Messenger RNA is isolated either from freshly purified head and neck cancer stem cells or from head and neck cancer stem cells incubated in the presence or absence of various Notch ligands. The RNA is amplified if necessary, such as by PCR or linear RNA amplification Wang et al., *Nature Biotechnology.* 18:457-459 (April 2000). Probe are prepared by reverse transcription from an oligo-dT primer, and labeled by incorporating CY3 or CY5 conjugated nucleotides. Gene expression profiles are examined using probe prepared from freshly isolated, uncultured head and neck cancer cells, as well as from cultured head and neck cancer cells, such as cells that have been exposed to the appropriate Notch ligands (including Fringe family members, either singly or in combination as determined by which ligands are expressed by the different populations of tumor cells. To do these assays, cells are exposed to a soluble form of Delta or Jagged family members in which the transmembrane region has been deleted, or one of the Fringes. The Fringes are secreted proteins. Recombinant proteins are made of each Notch ligand of the Delta, Jagged and Fringe families from insect cells or mammalian cells transfected with a baculovirus or mammalian expression vector, respectively.

Comparisons of gene expression patterns between control head and neck cancer tumorigenic cells and tumorigenic cells exposed to various Notch ligands are made. Probe from head and neck cancer stem cells from each tumor is combined with probe labeled with a different fluor made from cultured head and neck cancer stem cells exposed to various Notch ligands to compare their hybridization patterns. To do this, head and neck cancer stem cells are isolated by FACS. Cells are seeded at single cell density to preclude Notch interactions between cells. Cells are exposed to soluble forms of Delta, Delta-like, Jagged 1, Jagged 2, or each of the Fringes. Cells are exposed to each protein both alone and in combinations suggested by the Notch-ligand expression pattern of individual cell populations. The microarrays hybridized with probe from each test condition are compared and analyzed to gain insights into molecular pathways affected by Notch ligand interactions. For example, if a particular population of cells expresses Delta and Manic Fringe, then one group of head and neck cancer stem cells is exposed to Delta alone, a second to Delta and Manic Fringe and a third to Manic Fringe alone. cDNA is made from each population with Cy5 or Cy3 labeling, and used to probe a microarray chip. In addition, cDNA from each population is used with cDNA made from cells cultured in control medium and freshly isolated head and neck cancer cells to probe a microarray chip. Each group is compared 5 times to assure that any differences in expression profiles of the arrayed genes by each test groups are real.

Preparation of probe from cells treated with the anti-Notch 4 antibody. An antibody against Notch 4 inhibits growth in vitro and tumorigenesis in vivo. This effect can be explained if the antibody acts as either a Notch-4 agonist or antagonist. Since soluble Delta promotes cancer cell growth in vitro, the antibody most likely is a Notch 4 antagonist. To confirm the mechanism by which the anti-Notch 4 antibody inhibits tumor growth, probe is made from cells incubated in the presence or absence of the anti-Notch 4 or control irrelevant antibody and the various combinations of the Notch ligands and used for microarray expression analysis as described above. Another control group includes cells incubated with the antibodies and no Notch ligand. Each comparison is performed in at least six independent tests employing independently prepared batches of probe. By comparing the gene expression patterns of each group, how the anti-Notch 4 antibody affects Notch signaling can be determined.

Making the cDNA probe. 1-2 µg of mRNA is commonly used to synthesize probe for screening gene expression profiles on microarrays (Wang et al., *Nature Biotechnology.* 18:457-459 (April 2000)). 6 µg of mRNA is required per assay (reverse transcription of 6 µg of mRNA should yield around 3 µg of cDNA probe, or 1 µg of probe per slide). Cancer cells tend to have a high RNA content. In past assays, $10^7$ cancer cells yielded around 100 µg of total RNA, which in turn yielded around 3 µg of poly A$^+$ RNA. Thus in order to generate 6 µg of mRNA, around $2\times10^7$ cells would be required. As described in the data, that number of flow-cytometrically purified head and neck cancer stem cells can be isolated from approximately five-ten 1 cm tumors.

The head and neck cancer stem cells represent approximately 5% of the total number of cells within a tumor. It is not practical to isolate more than $10^6$ freshly dissociated (uncultured) head and neck cancer stem cells by flow-cytometry in one day. This would yield less than 0.5 µg of mRNA from one day of sorting. While head and neck cancer stem cells can be combined from multiple days of sorting to pool enough mRNA to prepare probe from freshly isolated cells, it may not be practical to perform all assays in this manner. Some assays require brief periods of tissue culture. Plating efficiency of the sorted cells is approximately 10%. Thus it may be necessary to enzymatically amplify the template prior to synthesizing probe. This can be done either by PCR or by linear amplification of RNA using T7 RNA polymerase. The protocol employs 15-18 rounds of PCR to amplify cDNA from small numbers of stem cells. This protocol was used to construct a high quality hematopoietic stem cell (HSC) cDNA library and to make probe from hematopoietic stem cells. To produce probe from freshly isolated head and neck cancer stem cells, the same approach is tested. Alternately, a number of groups have reported success in using linear RNA amplification to produce probe for microarray hybridization. Thus, the two methods are compared by preparing probe both ways and examining the hybridization patterns that result. cDNA is primed using an oligo-dT primer that contains a T7 RNA polymerase binding site and synthesized by Superscript reverse transcriptase (Gibco) and the Clontech 5's switch oligomer that allows the tagging of the 5' end of the cDNA. Second strand cDNA is synthesized using *E. coli* DNA polymerase. Then amplified RNA (aRNA) is produced using T7 RNA polymerase or PCR. Which of the two that amplification methods are used is determined by comparing probe made with standard cDNA synthesis. After preparing aRNA, cDNA is re-synthesized using random hexamers. This cDNA can then be used for probe, or if necessary, additional rounds of amplification can be performed. Both approaches are used to prepare probe from 40,000 MCF-7 cells (a human breast cancer stem cell line). This probe is hybridized to human cDNA microarrays along with probe from unamplified MCF-7 cells. The amplification approach that most closely reproduces the hybridization pattern of the unamplified probe is selected. Then amplification conditions are modified until the amplified probe reproduces the hybridization pattern of the unamplified probe as closely as possible.

Analysis of the hybridization pattern. Hybridization patterns are analyzed in the Cancer and Microarray Core facility using their laser scanning system. The use of an integrated system for arraying, hybridizing, scanning, and analyzing hybridization patterns in which all components are provided by Genomics Solutions permits a seamless and efficient analysis of hybridization patterns.

A transcript is differentially expressed if there is at least a 3-fold difference in normalized hybridization levels between probes. Hybridization signals from Cy3 and Cy5 labeled probes within a single test are normalized to each other to correct for potential differences in the effective concentration of each probe and replicates of each test are done using the opposite fluor for each group to correct for differences in the amounts or labeling efficiencies of probes.

Verification of differential expression. cDNAs that consistently hybridize to probe from groups of cells but not to probe from the control groups of cells are further characterized. The sequences of these cDNAs are obtained from the Microarray Network. Two approaches are used to confirm the differential expression of candidate genes between cell populations. The first is to prepare in situ hybridization probes against candidate genes, and then perform in situ hybridizations on head and neck cancer stem cells cultured in medium with or without various Notch ligands as described above. In situ hybridizations are then performed on cultured cells. The advantage of this approach would be that expression could be compared at the level of individual cells.

An alternate approach is to design nested PCR primers against candidate genes, and to perform RT-PCR on multiple 1-10-cell aliquots of freshly purified head and neck cancer stem cells (isolated as described above). By performing RT-PCR on small numbers of cells it is possible to observe a difference in the ability to amplify particular transcripts, even if the "non-expressing" population contains rare expressing cells. This approach was used to demonstrate the differential expression of RGS 18 between different subpopulations of multipotent hematopoietic progenitors.

Differential expression can be confirmed by Northern analysis. Poly A$^+$ RNA from $1-2\times10^7$ head and neck cancer stem cells cultured with or without the Notch ligands, are hybridized to probes of the differentially expressed cDNAs. Hybridization signals are quantitatively compared between these samples.

Confirmation that genes are differentially expressed at the protein level is then performed. In cases where immunocytochemical staining is uninformative, western blots on protein from the different cells are performed.

Certain molecular analyses are difficult using the primary head and neck cancer cells that only proliferate for prolonged periods of time in the xenograft model. These analyses can be done in cell lines. Any of a large number of head and neck cancer cell lines can be used. Clarke et al., *Proc. Natl. Acad. Sci. USA.* 92:11024-28 (November 1995); Hernandez-Alcoceba et al., *Human Gene Therapy.* 11:20 (September 2000). These cell lines are plated at single-cell density with and without various Notch ligands, as well as the anti-Notch 4 or control antibodies as described in the assays with the primary head and neck cancer cells. If clonogenicity is affected by Notch signaling, then probe for the microarray analysis is made using cDNA made form the cell line incubated in medium with or without the various Notch ligands or anti Notch 4 or control antibodies. Since a virtually unlimited number of cells can be analyzed, a probe can be made that has not been amplified.

Finally, cell lines are useful for confirming whether the anti-Notch 4 antibody is an agonist or antagonist. If a cell line is identified that clonogenicity is enhanced by soluble Delta and inhibited by the anti-Notch 4 antibody, then it is used in these assays. The cells are stably transfected with a luciferase minigene under the control of the Notch-inducible HES-1 promoter. Jarriault et al., *Molecular & Cellular Biology* 18:7423-31 (1998). The cells are plated at single cell density to prevent cell-cell Notch-Notch ligand interactions. They are treated with the various combinations of Notch ligands and either the anti-Notch 4 antibody or a control antibody. The cells are harvested and a luciferase assay is done to determine how each condition affects Notch signal transduction as reflected by transactivation of the HET1 promoter.

A comprehensive functional analysis of candidate genes that emerge from the microarray analysis can be performed. Full-length cDNAs are isolated and cloned into a retroviral expression vector. Head and neck cancer cell lines and head and neck cancer stem cells isolated from the five xenograft tumors are infected in vitro and the effect of the retroviral transgene on self-renewal and tumorigenicity is assayed relative to clones infected with a control vector. The transgene is expressed as a bicistronic message that contains IRES-GFP. This allows identification of transduced cells via FACS or fluorescent microscopy. The effect of the transgene on Notch signaling is examined in vitro and in vivo. To do this, transduced cells are tested for response to the various combinations of Notch ligands found to affect colony formation in tissue culture and tumorigenicity in mice.

The expression patterns of candidate genes are examined in detail in vivo to determine how widely the genes are expressed beyond the xenograft. In addition to performing more extensive in situ hybridizations of tissue sections from slices of primary head and neck cancer, antibodies against selected gene products being studied can be made. The Hybridoma Core facility at the University of Michigan has extensive experience preparing monoclonal antibodies using both peptides, and expressed recombinant proteins.

Ultimately, the functions of unknown genes are tested in vivo, using gene targeting to make knockout mice. The University of Michigan Transgenic Core has established murine ES cell technology, they provide ES cells that "go germline" at a high rate and assist with the generation of homologous recombinant ES clones.

The ability of microarray analysis to simultaneously compare the expression of many genes provides unparalleled power to screen for changes in gene expression patterns. Combined with the ability to purify stem cells and to regulate their self-renewal and differentiation in vitro, microarray analyses can be applied with great precision to screen for specific types of regulatory genes.

Example 15

Cancer Stem Cells as a Side Population

Certain stem cell populations, including hematopoietic stem cells (HSC), have the ability to efflux a fluorescent dye (e.g. Hoechst 33342) and correspond to a "side population" of cells (Goodell M A, Brose K, Paradis G, Conner A S, Mulligan R C. *J Exp Med.* (1996) 183:1797-1806; Kim M, Turnquist H, Jackson J, et al. Clin Cancer Res. (2002) 8:22-28; Scharenberg C W, Harkey M A, Torok-Storb B., Blood (2002) 99:507-512; Zhou S, Morris J J, Barnes Y, Lan L, Schuetz J D, Sorrentino B P. Proc Natl Acad Sci USA. (2002) 99:12339-44). To determine whether tumorigenic stem cells are enriched in a side population (SP) of cells, PE13 and UMC4 tumor cells were labeled with Hoechst 33342 for 30 minutes at 37° C., followed by incubation, wherein cells can actively efflux the dye if they have high efflux activity. Following Hoechst 33342 labeling and efflux incubations, cells were labeled with ESA-FITC and CD44-APC so the phenotype of SP cells might be identified. In both breast PE13 and colon UMC4 tumors, SP cells were highly enriched for ESA$^+$CD44$^+$ cells (FIG. 14A).

To determine whether tumorigenicity was also maintained, or even enriched in SP versus non-SP ESA$^+$CD44$^+$ cells, various populations were isolated by FACS and injected into mice. While the SP population was enriched for tumorigenic cells, SP did not exclusively parse tumorigenic, and ESA$^+$CD44$^+$ cells from SP or non-SP were equally tumorigenic, demonstrating the greatest association of tumorigenicity with the ESA$^+$CD44$^+$ phenotype. Thus, isolation of SP provides a mechanism for the partial enrichment of cancer stem cells. Of note, tumors from cells sorted using the SP protocol arose with longer latency and less frequency, thus it is likely that some toxicity was associated with SP cell procurement, possibly due to the Hoechst staining protocol or the brief violet laser exposure during FACS.

Microarray studies using mRNA from tumorigenic versus non-tumorigenic colon tumor populations isolated by FACS showed differential expression by a number of ABC family transporters (FIG. 14B), believed to be responsible for the efflux ability of the SP (Alison M R. J. Pathol. (2003) 200:547-550; Glavinas H, Krajcsi P, Cserepes J, Sarkadi B., Curr Drug Deliv. (2004) 1:27-42. Some, such as ABCD3 and ABCE1, were significantly higher in the tumorigenic population, whereas others (e.g. ABCC3) were more highly expressed in non-tumorigenic tumor cells. Differential expression of ABC family transporters on cancer stem cells or non-tumorigenic tumor cells can be utilized in prognostic or therapeutic applications.

Example 16

CD59 Enriches for Colon Cancer Stem Cells

CD59 mRNA was identified as being significantly overexpressed in tumorigenic versus nontumorigenic cells from colon tumors UMC4 and UM-C6 by microarray analysis (FIG. 15A). Flow cytometry also demonstrated that the TG ESA$^+$CD44$^+$ population expressed higher levels of surface CD59 protein than the remaining non-tumorigenic tumor populations (FIG. 15B). This was most pronounced in UM-C6 tumor cells, where CD59 cleanly distinguished CD44$^+$ cells from non-tumorigenic CD44$^-$ cells, thereby suggesting its value as a marker for enriching cancer stem cells in some tumor samples. In an attempt to determine whether CD59 expression might identify a NTG population among ESA$^+$CD44$^+$ cells of colon tumors, thereby also allowing further enrichment of TG colon cancer stem cells, primary xenograft tumors were depleted of murine cells (Lineage-depleted), and subpopulations of ESA$^+$CD44$^+$ cells were isolated by FACS based on CD59 expression (FIG. 15B). In UMC4 cells, CD59$^{hi}$ cells generally also have higher surface expression of CD29 (β1-integrin), another molecule discovered to be more highly expressed at mRNA level in TG colon cancer stem cells by microarray studies and confirmed at the protein level with FACS analysis.

An experiment with UMC4, demonstrated a correlation between CD59 and xenogeneic tumor engraftment/growth in the ESA$^+$CD44$^+$ population (FIG. 15C & Table 4).

TABLE 4

|  | Tumors/Injections | |
|---|---|---|
| UMC4 | 200 | 100 |
| ESA$^+$CD44$^+$CD49f$^+$ | 5/5 | 5/10 |
| ESA$^+$CD44$^+$CD49f$^-$ | 2/5 | 2/10 |
| ESA$^+$CD44$^-$ | 0/5 | — |
| UMC4 | 500 | |
| ESA$^+$CD44$^+$GD59$^+$ | 13/14 | — |
| ESA$^+$CD44$^+$CD59$^-$ | 5/7 | — |
| ESA$^+$CD44$^-$ | 0/4 | — |

13/14 mice injected with CD59$^{int/high}$ ESA$^+$CD44$^+$ cells developed tumors that rapidly grew to over 2,000 cm$^2$. Only 4/7 tumors with CD59$^{low}$ ESA$^+$CD44$^+$ cells developed, and those that did grow, grew more slowly than those tumors that developed with CD59$^{int/hi}$ cells. 0/4 tumors grew larger than 200 cm$^2$ (only 1 had any growth, but regressed after 5 weeks) with ESA$^+$CD44$^-$ cells. The correlation between CD59 and engraftment/growth can reflect a couple of possibilities: a) CD59 protects cells from death or host immunosurveillence and thus tumors have a better chance of developing, and/or b) CD59 demarcates the tumorigenic subset of ESA+CD44+ cells in UMC4 tumors. It should be noted that the "spread" of CD59 expression was not wide, but could nevertheless prove useful. All resulting tumor phenotypes in this study looked normal (~9-15% ESA+CD44+).

Example 17

CD49 Enriches for Colon Cancer Stem Cells

CD49 mRNA was identified as being significantly overexpressed in tumorigenic versus nontumorigenic cells from colon tumors UMC4 and UM-C6 by microarray analysis. In an attempt to determine whether CD59 expression might identify a NTG population among ESA$^+$CD44$^+$ cells of colon tumors, thereby also allowing further enrichment of TG colon cancer stem cells, primary xenograft tumors were depleted of murine cells (Lineage-depleted), and subpopulations of ESA$^+$CD44$^+$ cells were isolated by FACS based on CD49 expression (FIG. 16A). An experiment with UMC4, demonstrated a correlation between CD49 and xenogeneic tumor engraftment/growth in the ESA$^+$CD44$^+$ population (FIG. 16B & Table 4).

All publications and patents cited herein are incorporated by reference herein in entirety. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

What is claimed is:

1. A method for obtaining from a colon tumor a cellular composition comprising colon cancer stem cells and non-tumorigenic colon tumor cells, wherein at least 75% of the tumor cells in the composition are tumorigenic colon cancer stem cells and 25% or less of the tumor cells in the composition are non-tumorigenic colon tumor cells, said method comprising:
    (a) obtaining a dissociated mixture of colon tumor cells; and
    (b) separating the mixture of colon tumor cells into a first fraction comprising at least 75% colon cancer stem cells and 25% or less non-tumorigenic colon tumor cells and a second fraction of colon tumor cells depleted of colon cancer stem cells wherein the separating comprises contacting the mixture with reagents against CD44 and epithelial-specific antigen (ESA); and
    (c) collecting said first fraction, wherein said colon cancer stem cells in said first fraction are CD44$^+$ and ESA$^+$.

2. The method of claim 1, wherein the separating is performed by flow cytometry, fluorescence activated cell sorting (FACS), panning, affinity chromatography or magnetic selection.

3. The method of claim 1, wherein the separating is performed by fluorescence activated cell sorters (FACS) analysis.

4. The method of claim 1, wherein the separating further comprises contacting the mixture with reagents against at least one additional reagent against a protein selected from the group consisting of: HES6, CD166, CEACAM6, CD59, and CD49f.

5. A method for preparing a population of colon tumor cells enriched for colon cancer stem cells, wherein the enriched population comprises 75% or more colon cancer stem cells and 25% or less non-tumorigenic colon tumor cells, said method comprising:
    (a) obtaining a dissociated mixture of colon tumor cells;
    (b) contacting the mixture of colon tumor cells with reagents against CD44, CD166, and ESA;
    (c) selecting a first fraction enriched for colon cancer stem cells by their binding to the reagents and a second fraction of colon tumor cells depleted of colon cancer stem cells; and
    (d) collecting said first fraction, wherein said colon cancer stem cells in said first fraction are CD44$^+$ and ESA$^+$.

6. The method of claim 5, wherein the selecting is performed by flow cytometry, fluorescence activated cell sorting (FACS), panning, affinity chromatography, or magnetic selection.

7. The method of claim 5, wherein the selecting is performed by fluorescence activated cell sorters (FACS) analysis.

8. The method of claim 5, wherein the reagents with which the mixture of colon tumor cells are contacted further comprise a reagent against HES6.

9. The method of claim 5, wherein the mixture of colon tumor cells are further contacted with a reagent against CD59.

10. The method of claim 5, wherein the mixture of colon tumor cells are further contacted with a reagent against CD49f.

11. The method of claim 5, wherein the mixture of colon tumor cells are further contacted with a reagent against CEACAM6.

12. A method for obtaining from a colon tumor a cellular composition comprising colon cancer stem cells and non-tumorigenic colon tumor cells, wherein at least 75% of the tumor cells in the composition are tumorigenic colon cancer stem cells and 25% or less of the tumor cells in the composition are non-tumorigenic colon tumor cells, said method comprising:
    (a) obtaining a dissociated mixture of colon tumor cells;
    (b) separating the mixture of colon cancer tumor cells into a first fraction comprising at least 75% colon cancer stem cells and 25% or less non-tumorigenic colon tumor cells and a second fraction of colon tumor cells depleted of colon cancer stem cells, wherein the separating comprises contacting the mixture with reagents against CD44, ESA, and CD49f; and
    (c) collecting said first fraction, wherein said colon cancer stem cells in said first fraction are CD44$^+$, ESA$^+$, and CD49f$^{hi}$.

13. The method of claim 12, wherein the separating is performed by flow cytometry, fluorescence activated cell sorting (FACS), panning, affinity chromatography or magnetic selection.

14. The method of claim 12, wherein the separating is performed by fluorescence activated cell sorters (FACS) analysis.

15. The method of claim 12, wherein the separating further comprises contacting the mixture with reagents against HES6.

16. The method of claim 12, wherein the separating further comprises contacting the mixture with reagents against CD166.

17. The method of claim 12, wherein the separating further comprises contacting the mixture with reagents against CEACAM6.

18. The method of claim 12, wherein the separating further comprises contacting the mixture with reagents against CD59.

* * * * *

UNITED STATES PATENT AND TRADEMARK OFFICE
CERTIFICATE OF CORRECTION

PATENT NO. : 7,723,112 B2
APPLICATION NO. : 11/591019
DATED : May 25, 2010
INVENTOR(S) : Michael F. Clarke et al.

It is certified that error appears in the above-identified patent and that said Letters Patent is hereby corrected as shown below:

Col. 1 lines 9-12 should read
This invention was made with government support under CA104987 awarded by the National Institutes of Health. The Government has certain rights in the invention.

Signed and Sealed this

Sixth Day of July, 2010

David J. Kappos
*Director of the United States Patent and Trademark Office*